United States Patent [19]
Sanka et al.

[11] Patent Number: 5,696,686
[45] Date of Patent: *Dec. 9, 1997

[54] COMPUTER SYSTEM FOR QUALITY CONTROL CORRELATIONS

[75] Inventors: Ravi Sankar Sanka; Daniel Tsu-Fang Wang; Richard Wayne Abrams; John Mark Lepper, all of Jacksonville; Wallace Anthony Martin, Orange Park; Craig William Walker; Kenneth Kurt Pricer, both of Jacksonville; Lars William Johnson, Indialantic; Leonard Ross Reinhart, Melbourne Beach; James K. Miars, Palm Bay, all of Fla.

[73] Assignee: Johnson & Johnson Vision Products, Inc., Jacksonville, Fla.

[*] Notice: The term of this patent shall not extend beyond the expiration date of Pat. No. 5,461,570.

[21] Appl. No.: 431,632

[22] Filed: May 1, 1995

Related U.S. Application Data

[63] Continuation-in-part of Ser. No. 257,800, Jun. 10, 1994, Pat. No. 5,461,570.

[51] Int. Cl.⁶ ............................................. G06F 19/00
[52] U.S. Cl. ............................... 364/468.17; 364/552
[58] Field of Search ................ 364/468.01, 468.02, 364/468.15, 468.16, 468.17, 468.24, 550, 551.01, 552; 264/1.1, 1.6, 2.6, 40.1; 425/808, 162, 169

[56] References Cited

U.S. PATENT DOCUMENTS

| | | | |
|---|---|---|---|
| 4,495,313 | 1/1985 | Larsen | 523/106 |
| 4,565,348 | 1/1986 | Larsen | 249/122 |
| 4,640,489 | 2/1987 | Larsen | 249/122 |
| 4,680,336 | 7/1987 | Larsen et al. | 264/1.4 |
| 4,691,820 | 9/1987 | Martinez | 206/205 |
| 4,761,069 | 8/1988 | Troung et al. | 351/160 |
| 4,889,664 | 12/1989 | Kindt-Larsen et al. | 264/2.6 |
| 4,980,993 | 1/1991 | Umezaki | 451/5 |
| 5,039,459 | 8/1991 | Kindt-Larsen et al. | 264/2.6 |
| 5,080,839 | 1/1992 | Kindt-Larsen | 264/2.6 |
| 5,094,609 | 3/1992 | Kindt-Larsen | 425/445 |
| 5,122,976 | 6/1992 | Bellows et al. | 364/550 |
| 5,461,570 | 10/1995 | Wang et al. | 364/468.17 |
| 5,469,361 | 11/1995 | Moyne | 364/468.01 |

FOREIGN PATENT DOCUMENTS 629 410 A1  12/1994  European Pat. Off. .......... A61L 2/24

Primary Examiner—Joseph Ruggiero

[57] ABSTRACT

A sterilizer data processing system for an automated contact lens manufacturing line that manufactures a plurality of contact lenses defining a lens lot, the manufacturing line including an automated sterilization station for sterilizing the lens lot after their manufacture, the automated sterilization station including a sterilizer process controller for controlling one or more phases of a sterilization process and periodically generating sterilization process data during each sterilization phase includes a device for receiving the sterilization process data from the sterilizer process controller and a device for automatically parsing the sterilization data into text information and sterilizer parameter information and further processing the text information and sterilizer parameter information to automatically generate a sterilization run report associated with a lot number for the sterilized lens lot.

25 Claims, 42 Drawing Sheets

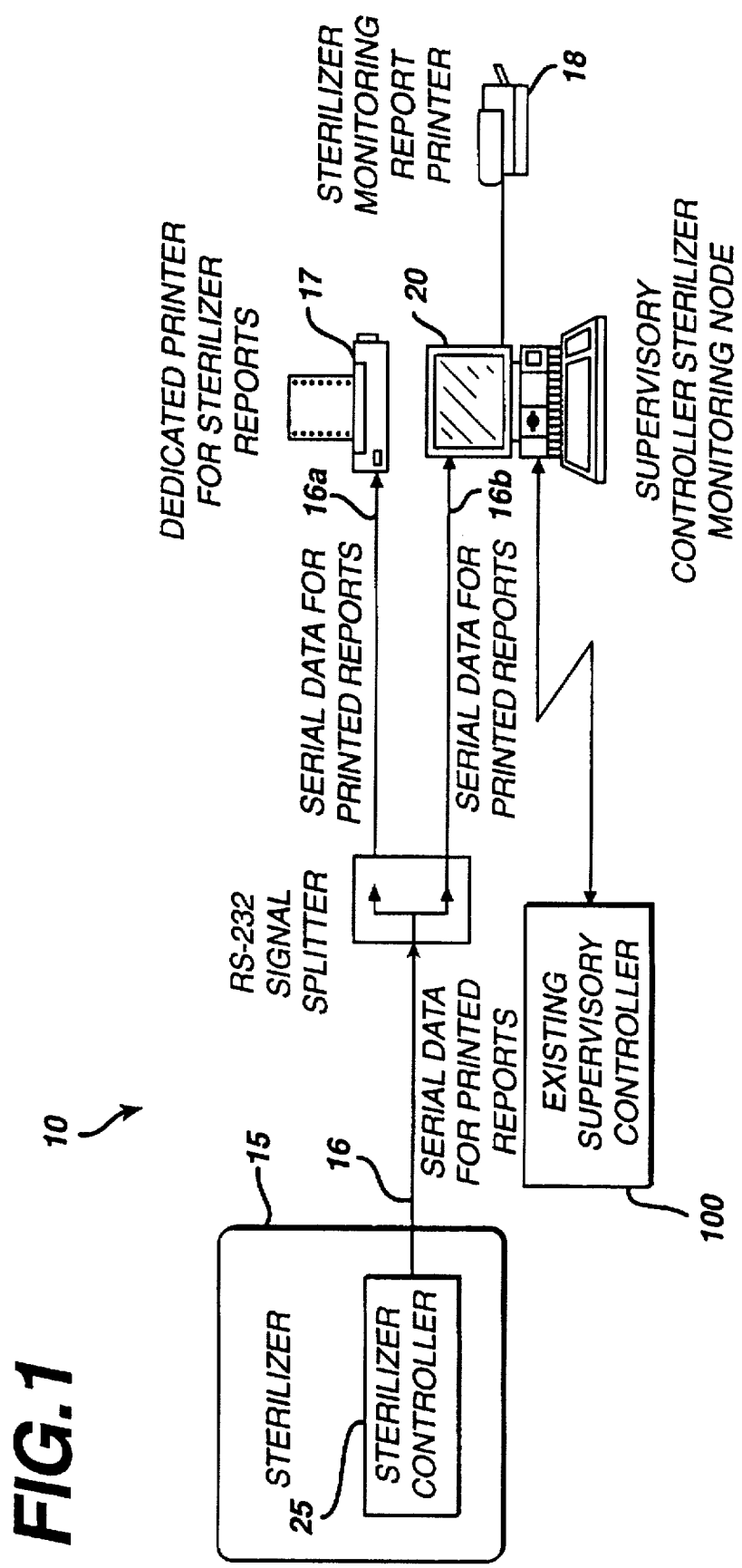

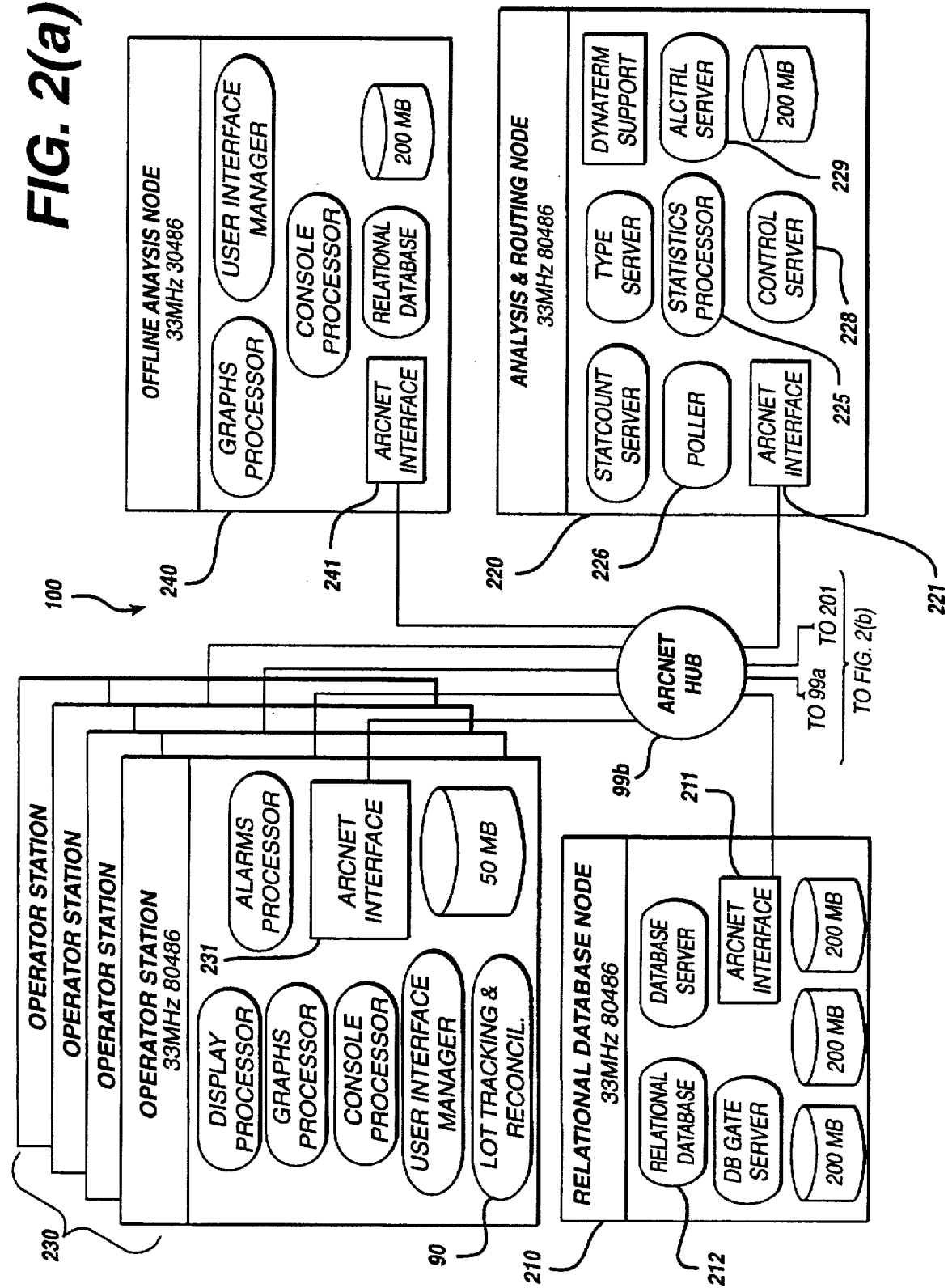

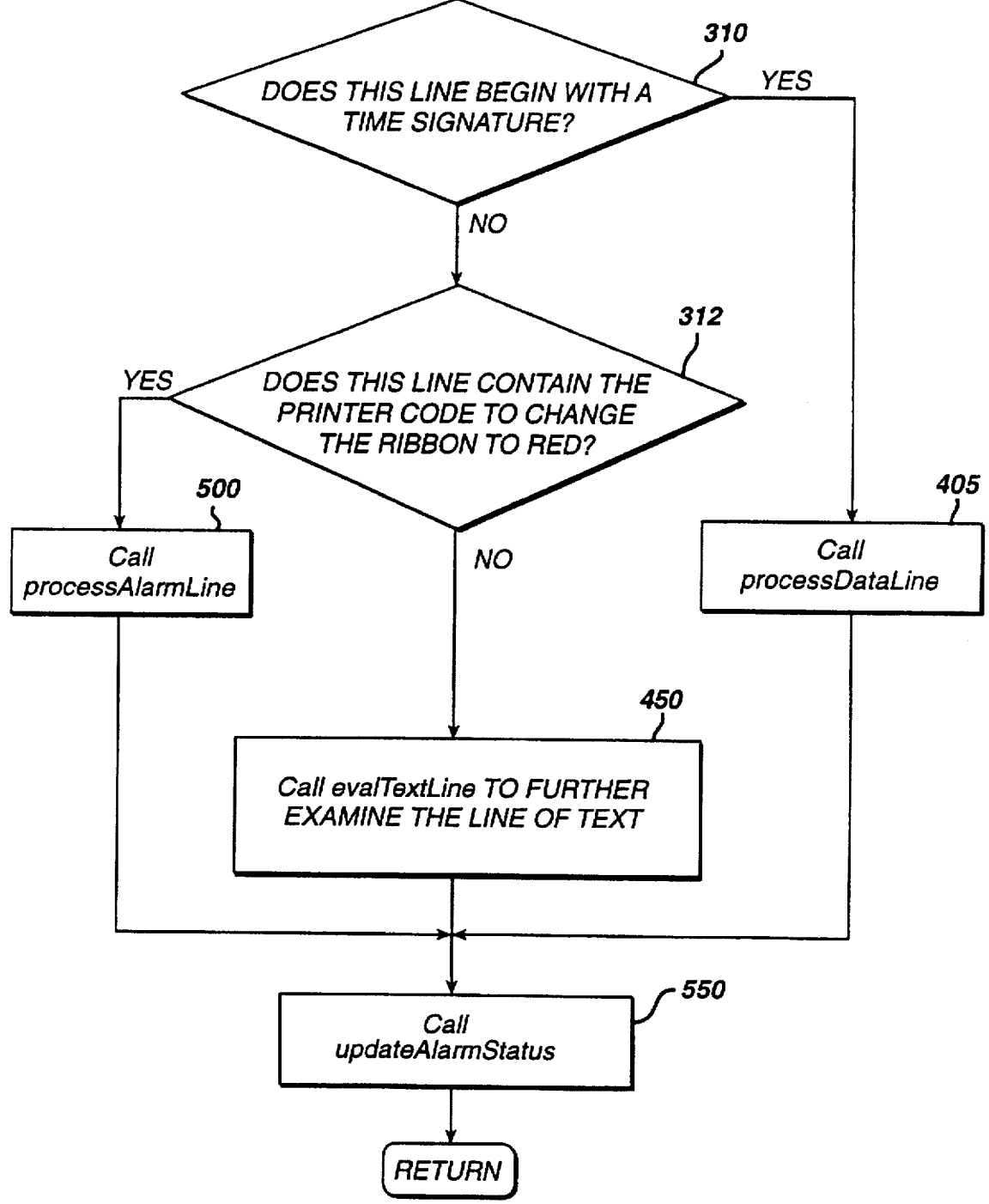

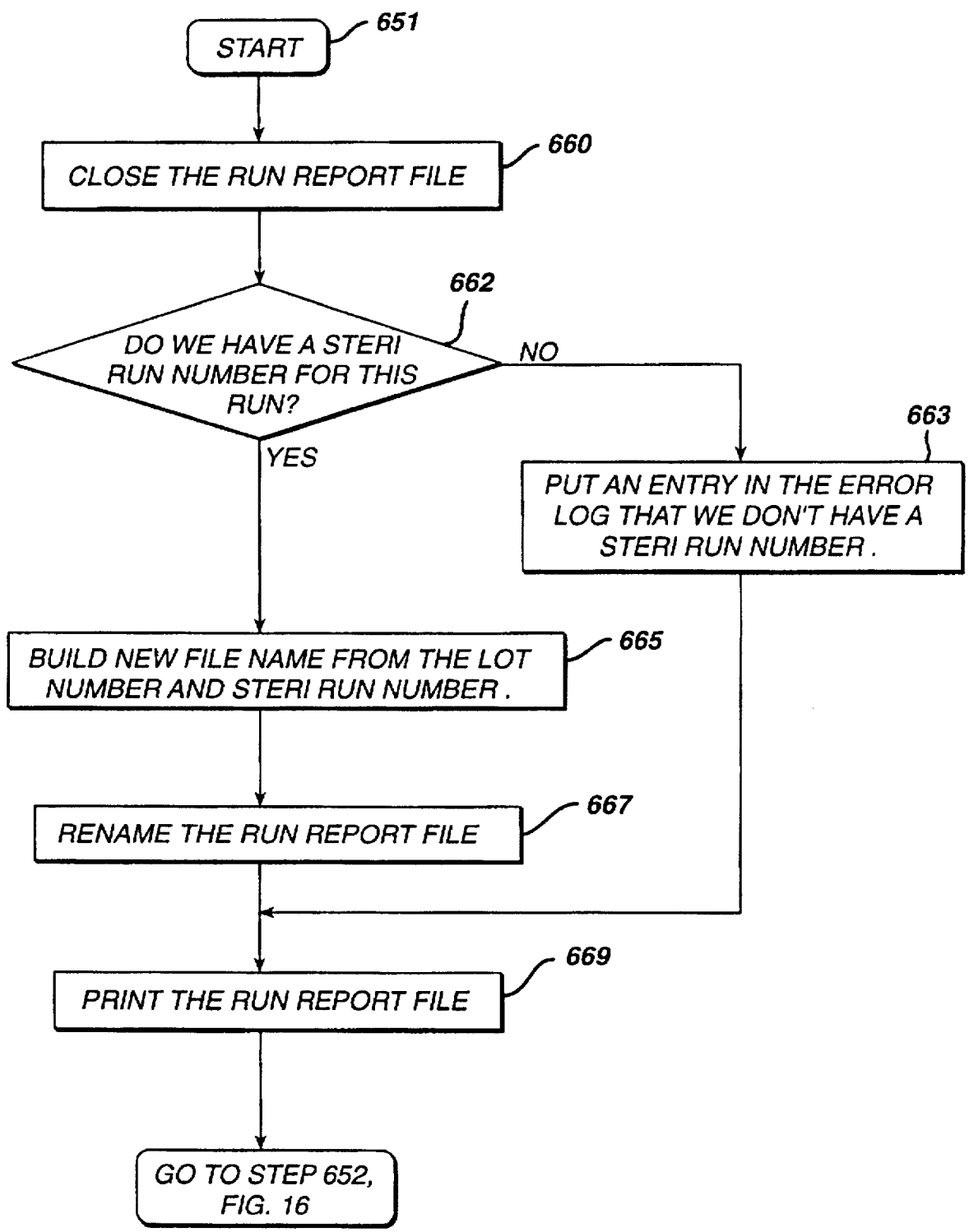

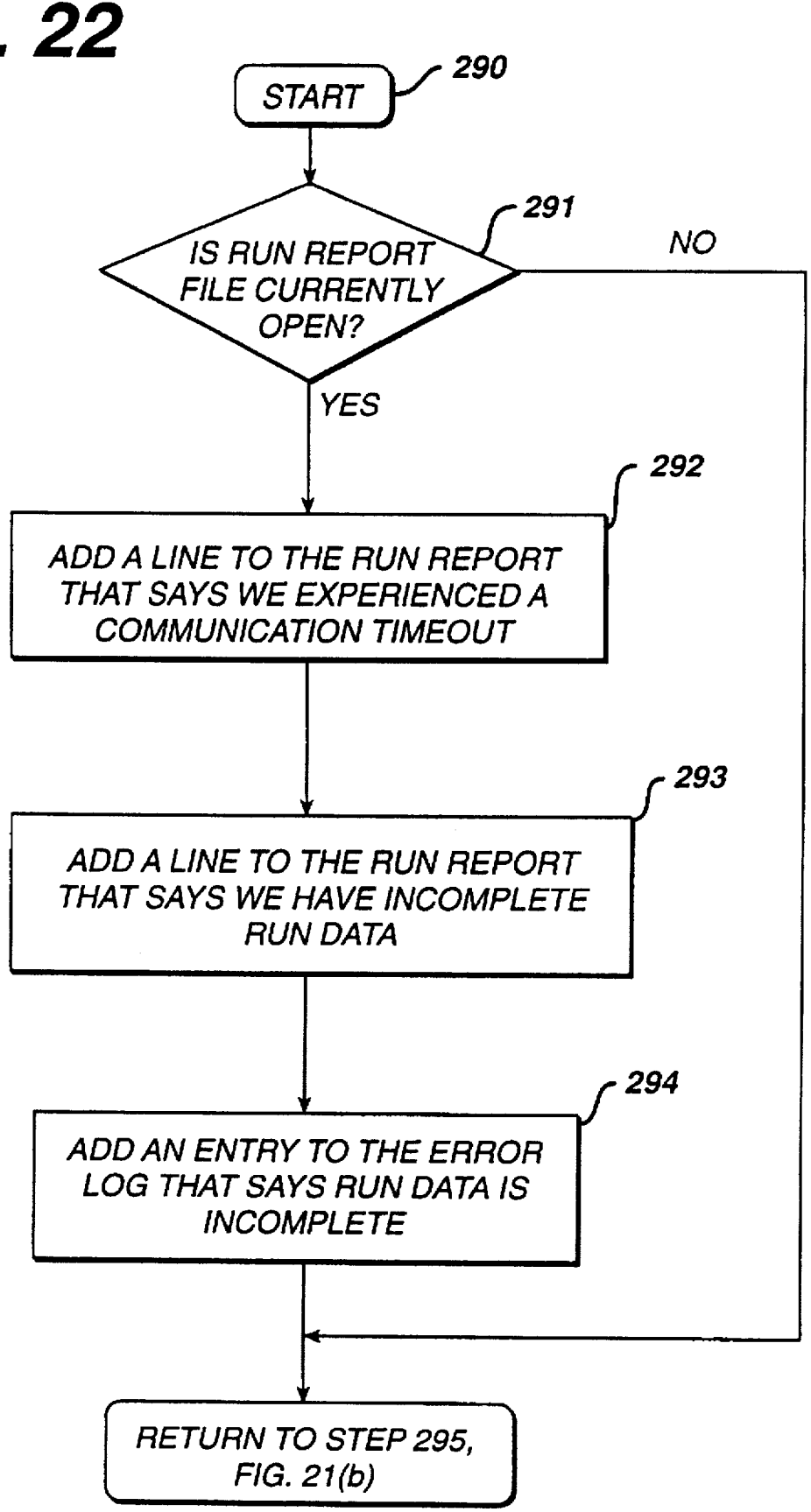

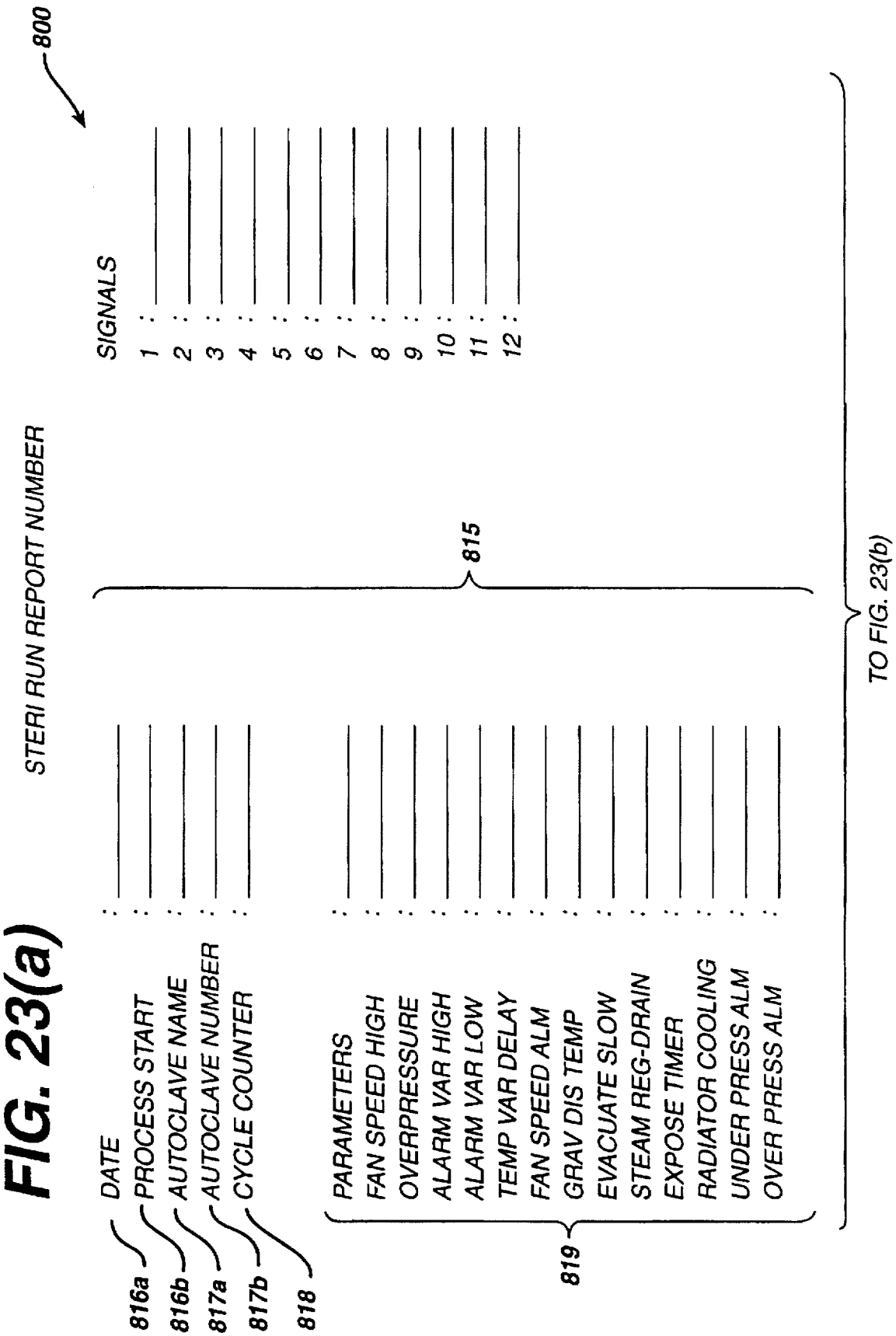

FIG. 23(b)

FROM FIG. 23(a) — TO FIG. 23(c)

PROGRAM: 800

| PROGTIME | V1 | V2 | V3 | V4 | V5 | V6 | V7 | V8 | V9 | V10 | V11 | V12 |
|---|---|---|---|---|---|---|---|---|---|---|---|---|
| START | | | | | | | | | | | | |
| 00:00:00 | x | | | | | x | x | x | x | x | x | x |
| HEAT LOAD | | | | | | | | | | | | |
| 00:00:00 | x | x | x | | | • | • | • | • | | | |
| 00:00:49 | x | x | x | x | x | • • • | • | • | • | | | |
| 00:01:22 | x | x | x | x | x | • | • | • | • | | | |
| EXPOSURE | | | | | | | | | | | | |
| 00:05: | x | x | x | x | x | • • • | • | • | • | | | |
| 00:05:49 | x | x | x | x | x | | | | | | | |
| 00:06:49 | x | x | x | x | x | | | | | | | |
| COOL LOAD | | | | | | | | | | | | |
| 00:36:27 | x | x | x | x | x | • • • | • | • | • | | | |
| 00:36:49 | x | x | x | x | x | | | | | | | |
| 00:37:49 | x | x | x | x | | | | | | | | |
| CYCLE COMPLETE | | | | | | | | | | | | |
| 00:46:04 | x | x | x | x | x | • | • | • | • | | | |
| VALID CYCLE | x | | | | | | | | | | | |

{ 825 } (bracket over V6–V12 columns)

FIG. 23(c)

FROM FIG. 23(b)

— 800

805

SIGNATURE : ..................
STERILIZER RUN NUMBER : — 812
A COMPLETE SET OF DATA WAS OBTAINED FROM THE STERILIZER CONTROLLER. — 855
THE STERILIZER CONTROLLER REPORTED A VALID CYCYCLE. — 850

- - - - PHASE DURATIONS (M:MM:SS) - - - - 830

835 { 845 {

| | HEAT LOAD qq.rr | EXPOSURE ss.tt | COOL LOAD uu.vv | CYCLE COMPLETE ww.xx — 840 |
|---|---|---|---|---|
| | 1 2 | 3 4 5 | 6 7 8 9 10 | 11 12 |
| | — MINIMUM AND MAXIMUM VALUES — | | | |
| HEAT MIN | x — | — — — | — — — — — | — — |
| HEAT MAX | x — | — — — | — — — — — | — — |
| EXPS MIN | x — | — — — | — — — — — | — — |
| EXPS MAX | x — | — — — | — — — — — | — — |
| COOL MIN | x — | — — — | — — — — — | — — |
| COOL MAX | x — | — — — | — — — — — | — — |
| COMP MIN | x — | — — — | — — — — — | — — |
| COMP MAX | x — | — — — | — — — — — | — — |

FIG. 25(a)

| LOT NUMBER | UPC | R/T | POWER | THICKNESS | EXPIRATION |

FIG. 25(b)

| LOT NUMBER | UPC | R/T | POWER | THICKNESS | EXPIRATION | INPUT QTY | LOSS QUANTITY |

FIG. 31

| LOT NUMBER | DATE | TIME | MODE | VARIABLE #1 READING | VARIABLE #2 READING | ... | VARIABLE #12 READING |
|---|---|---|---|---|---|---|---|
| | | | | | | | |
| LOT NUMBER | DATE | TIME | MODE | VARIABLE #1 READING | VARIABLE #2 READING | ... | VARIABLE #12 READING |
| ... | ... | ... | ... | ... | ... | ... | ... |
| LOT NUMBER | DATE | TIME | MODE | VARIABLE #1 READING | VARIABLE #2 READING | ... | VARIABLE #12 READING |

STERILIZATION / SECONDARY PACKAGING LOT RECONCILIATION SHEET    890

STERILIZATION RUN # (s)

MASTER LOT # _____
LENS POWER + - _____
MASTER    SPLIT        (CIRCLE)
REVENUE   TRIAL        (CIRCLE)

891
— # OF LENSES ENTERING ZONE #1                    -A- _____
     (STERI TRAY LOAD)
892  SIGNATURE _____ DATE _____
— # OF LENSES REMOVED AT ZONE #1                  -B- _____
     (STERI TRAY LOAD)
893  SIGNATURE _____ DATE _____
— # OF LENSES REMOVED AT ZONE # & #               -C- _____
     (STERI TRAY UNLOAD / CARTONING
     & CARTON CHECKWEIGH/ LABELING)
894  SIGNATURE _____ DATE _____
— # OF LENSES REMOVED BY QUALITY ASSURANCE        -D- _____
895  SIGNATURE _____ DATE _____
— # OF LENSES EXITING ZONE # 4                    -E- _____
     (CARTON CHECK WEIGH/LABELING)
     SIGNATURE _____ DATE _____

899  TOTAL OF ALL LENSES LEAVING THE CELL         -F- _____
     B + C + D + E

LOT RECONCILIATION                           -G- _____
     A - F

VERIFIED BY _____ DATE _____
                 QA TECHNICIAN

LOT TRANSFER DATE _____

COMPUTER SYSTEM FOR QUALITY CONTROL CORRELATIONS

CROSS REFERENCE TO RELATED APPLICATION

This application is a continuation-in-part of U.S. Ser. No. 08/257,800 entitled COMPUTER SYTEM FOR QUALITY CONTROL CORRELATIONS and filed Jun. 10, 1994, now U.S. Pat. No. 5,461,570.

FIELD OF THE INVENTION

This invention relates generally to a computer system for a manufacturing facility for the production of ophthalmic contact lenses, and, in particular to a supervisory system for monitoring the production line processes used in the manufacture of contact lenses in a contact lens fabrication facility, specifically, with the goal of investigating and optimizing the process of contact lens sterilization.

DESCRIPTION OF THE PRIOR ART

The direct molding of hydrogel contact lenses is disclosed in U.S. Pat. No. 4,495,313 to Larsen, U.S. Pat. No. 4,680,336 to Larsen et al., U.S. Pat. No. 4,565,348 to Larsen, and U.S. Pat. No. 4,640,489 to Larsen et al., the entire disclosures of which are hereby incorporated by reference in this patent application. Essentially, these references disclose an automated contact lens production process wherein each lens is formed by sandwiching a monomer between back curve (upper) and front curve (lower) mold sections. The monomer is polymerized, thus forming a lens, which is then removed from the mold sections and further treated and packaged for consumer use.

The manufacturing of contact lenses requires tightly controlled conditions and processes, many of which are monitored by computers and other control devices. Much information, in the form of process conditions and control data, for e.g., that occur during contact lens manufacturing, may be gathered for quality control and regulatory approval purposes. However, this entails the acquisition of a tremendous amount of data for each contact lens that is produced, and, additionally, requires a means for processing the data acquired in a way that is suitable for use by operators, engineers, and supervisors, etc., so that they may properly perform their functions.

There is therefore the need to provide a quality control system that can automatically acquire process control data from a plurality of manufacturing process controllers that control various aspects of contact lens production at process stations in a contact lens manufacturing facility, and, that can automatically process the data for real-time display and archiving purposes. More particularly, there is a need for a quality control system that can automatically acquire data generated from a sterilization controller that controls a sterilization process performed to contact lenses that are individually packaged but not cartoned, and that is performed prior to their cartoning.

It would additionally be highly desirable to provide a quality control system that can automatically gather sterilization process control data for contact lenses for subsequent generation of sterilizer cycle condition records that includes: sterilization run success/failure indication, lot number, and sterilization run number from the sterilizer controller. These files may be stored in an off-line database storage area and be retrieved to analyze the trend of sterilizer performance over a long period of time. Furthermore, in accordance with the inventive processes described herein, these files may be processed to automatically generate reports that are suitable for compliance with Federal Food and Drug Administration ("FDA") record-keeping requirements, and are also useful for re-certifying the sterilizer.

SUMMARY OF THE INVENTION

An object of the instant invention is to provide a quality control system for a contact lens manufacturing facility that automatically acquires process control data from a plurality of manufacturing process controllers that control contact lens production, and, that can automatically process the data for real-time display and off-line analysis purposes.

Another object of the invention is to provide a quality control system for a contact lens manufacturing facility that implements a sterilization process for sterilizing individual contact lens packages after their primary packaging in blister packages and prior to their cartoning.

Still another object of the invention is to provide a quality control system for a contact lens manufacturing facility that includes a sterilization apparatus controlled by a sterilization controller for sterilizing individual contact lens packages prior to their cartoning. Additionally, another object of the invention is to provide a quality control system that gathers sterilization process control data from the sterilization controller and subsequently generates sterilizer cycle condition records that includes: sterilization run success/failure indication, lot number, and sterilization run number from the sterilizer controller.

Yet still another object of the invention is to provide a quality control system for a contact lens manufacturing facility that includes an apparatus for secondary packaging of sterilized blister packages containing individual contact lenses in cartons.

A further object of the invention is to provide a quality control system that incorporates means for automatically printing and correlating labelling information including lot number identification for all contact lens packages produced.

The above objects are achieved in a quality control system for an automated production line producing contact lenses, the production line having a plurality of contact lens process stations, including an automated sterilization station for sterilizing a plurality of contact lenses after their manufacture, and a packaging station for packaging said lenses after sterilization, wherein the system comprises:

(a) a first means for receiving contact lens data including an associated lot number and lens power for a lens lot prior to their manufacture; the lens lot defining at least one batch of contact lenses;

(b) a plurality of process controllers for controlling one or more process stations, each of the controllers regulating a plurality of process control devices at the process stations;

(c) means for tracking movement of the plurality of lenses defined by the lens lot from the plurality of processing stations to the automatic sterilization station and the packaging station;

(d) second means for receiving data representing the number of lenses that are input to the sterilization station and recording sterilization data for each batch of the lens lot together with reason codes for contact lenses lost at the sterilization station;

(e) means for generating a summary report of the total number of lenses input to the sterilization chamber for a predetermined lens lot and the actual number of lenses sterilized and packaged from the lot, the summary report including lot number, expiration date, power and sterilization data for each batch of contact lenses.

Further benefits and advantages of the invention will become apparent from a consideration of the following detailed description given with reference to the accompanying drawings, which specify and show preferred embodiments of the invention.

BRIEF DESCRIPTION OF THE DRAWINGS

The foregoing objects and advantages of a quality control system for an automated production line for producing contact lenses of the present invention, may be more readily understood by one skilled in the art with reference being had to the following detailed description of several preferred embodiments thereof, taken in conjunction with the accompanying drawings wherein like elements are designated by identical reference numerals throughout the several views, and in which:

FIG. 1 is an organizational overview of the sterilization monitoring system of the instant invention.

FIGS. 2(a) and 2(b) illustrate the hardware configuration of the existing supervisory control system 100 shown interfaced with the sterilizer monitoring node 20 and sterilizer controller 25 of the instant invention.

FIGS. 7(a) and 7(b) illustrate the characterizeLine algorithm 300 for determining the nature of the data line sent by the sterilization controller.

FIG. 20 illustrates the closeAndPrintRunReport procedure for closing the steri run report file.

FIG. 22 illustrates in detail the endRunReportForTimeout process 290 that is called to update the steri run report file.

FIGS. 23(a), 23(b) and 23(c) illustrate in detail the sterilization run report automatically generated for a complete sterilization cycle.

FIGS. 25(a) and 25(b) illustrate the respective data structures stored in the statistics server for the lot information before primary packaging (FIG. 25(a)) and after primary packaging (FIG. 25(b)).

FIG. 31 illustrates a table depicting phase file data entries in the four sterilizer phase files.

FIG. 32 illustrates the sterilization/secondary packaging lot reconciliation sheet.

DESCRIPTION OF THE PREFERRED EMBODIMENT

Figure 2B:
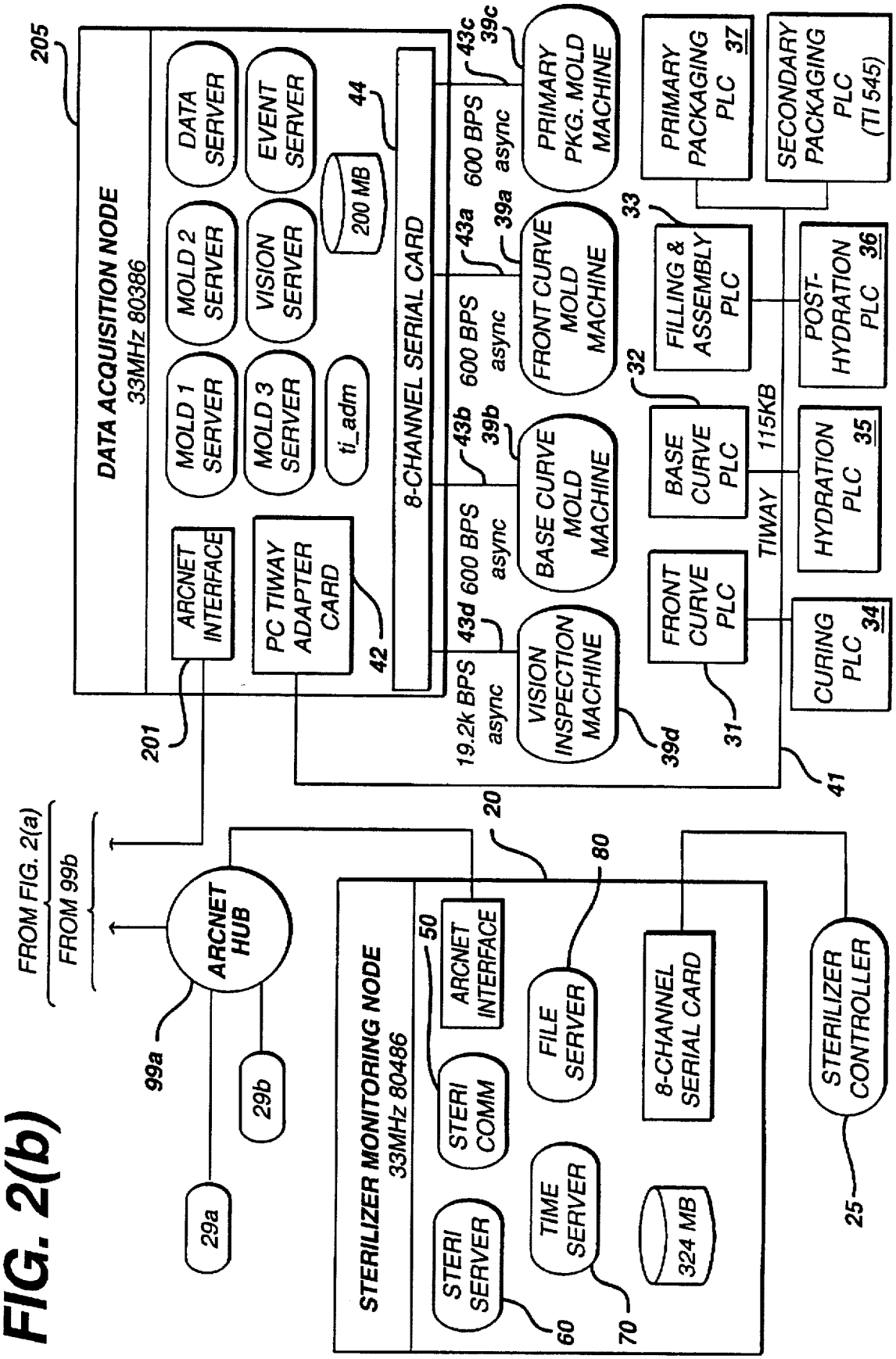

Illustrated in FIG. 1 is a general schematic diagram illustrating the sterilization monitoring system 10 for passively monitoring the sterilization and secondary packaging of contact lens packages. As will be explained in greater detail below, the sterilization monitoring system 10 of the invention is configured specifically to process sterilizer serial data and generate sterilization run reports.

As shown in FIG. 1, the sterilization monitoring system 10 comprises a sterilization chamber 15 having a sterilizer control device 25, which, in the preferred embodiment, is a PLC or dedicated process controller that controls the sterilization process and serially broadcasts the sterilization process data 16 and alarm data (when an alarm condition exists) as formatted ASCII characters to a dedicated printer 17, via data line 16a, as well as an intercepting sterilization monitoring node 20, via data line 16b, that is interfaced with an existing contact lens production line supervisor quality control system 100 ("existing supervisor system"). As will be explained in detail below, the sterilization node 20 will process the ASCII sterilizer data and automatically generates a sterilization run report, a portion of which is shown in FIG. 22, and explained in detail below, at a second printer 18. The operational details of the existing contact lens production line supervisor quality control system 100 are disclosed in the above-identified co-pending patent application U.S. Ser.

No. 08/257,800 now U.S. Pat. No. 5,461,570 entitled "Computer System for Quality Control Correlations", assigned to the same assignee as the instant invention, the specification and disclosure of which is incorporated herein by reference thereto. As described in the above-identified co-pending patent application U.S. Ser. No. 08/257,800, now U.S. Pat. No. 5,461,570, the existing supervisor system automatically acquires process control data from a plurality of programmable and non-programmable control devices that control and monitor various manufacturing processes, and, automatically processes the data for real-time display and off-line engineering analysis and quality assurance purposes.

FIGS. 2(a and 2(b) illustrate the hardware configuration of the existing Supervisor system 100 interfaced with the sterilizer monitoring node 20 and sterilizer controller 25 via ARCNET HUB network devices 99a and 99b that support communication between the sterilizer monitoring node, two operator terminals 29a,29b (preferably manufactured by Dynaterm), and, the existing supervisor system 100. Preferably, the sterilizer monitoring node 20 includes a 33 MHz Intel '486 computer having the following modules for performing the sterilization monitoring process: sterilization communication module and process 50, sterilization server module and process 60, a time server 70, and a file server 80. Each of these modules will be described in greater detail hereinbelow.

Briefly, the supervisor system 100 interfaces with and obtains control parameter data from the sterilization monitoring node, and, at least seven programmable logic controllers that control various contact lens manufacturing processes such as disclosed in co-pending patent application U.S. Ser. No. 08/257,654 entitled "Consolidated Contact Lens Molding", assigned to the same assignee as the instant invention, the specification and disclosure of which is incorporated herein by reference. These manufacturing processes include: transferring of injection molded front curve lens molds to carrier pallets as controlled by PLC 31; transferring of injection molded back curve lens molds to carrier pallets as controlled by PLC 32; monomer filling and contact lens mold assembly operations as controlled by PLC 33; the precure, UV curing, and lens de-mold operations as controlled by PLC 34; transfer of the front curve mold halves containing molded contact lenses to a hydration chamber for contact lens hydration as controlled by PLC 35; post hydration operations including the generation of contact lens inspection data consisting of pass/fail results as determined by an automatic vision system incorporated in an automatic lens inspection station as controlled by PLC 36; and, the primary contact lens packaging and lens package consolidation aspect of the lens packaging processes including such processes as solution exchange, saline fill, package foil heat seal, etc., which occur about a rotary index (packaging) dial (not shown) as controlled by PLC 37. An eighth PLC, may be provided for controlling various aspects of the secondary packaging including transfer of packages from the sterilization chamber to a secondary packaging area where the blister packs are labelled and sealed in secondary packaging cartons as described in co-pending patent application U.S. Ser. No. 08/257,788, now U.S. Pat. No. 5,488,815 entitled "Apparatus and Method for Sterilization and Secondary Packaging" assigned to the same assignee as the instant invention and, the disclosure of which is incorporated by reference herein. Secondary packaging briefly includes the steps of printing/applying bar-coded lot-number on the carton, printing the power and expiration date on the carton, inserting the blister packages into the carton and gluing carton flaps closed, verification of the lot number, verification of the power and expiration date, weighing the carton, loading and closing the case and applying the case label, and, loading and completing the pallet and applying the pallet label.

In the preferred embodiments, each PLC 31-38 is a TI system 545 (Texas Instruments) and may include a TI 386/ATM coprocessor module for communicating with the respective PLC across the backplane or by serial link (not shown). It is understood that each PLC has its own memory and addressing capabilities for storing and updating blocks of data.

As shown in FIGS. 2(a) and 2(b), other programmable device controllers, for example, those manufactured by Yushin Corp., are provided in a contact lens production line for controlling, respectively, the front curve mold machine 39a which produces the front curve lens molds at a rate of eight every six seconds, back curve mold machine 39b which produces the back curve lens molds, the primary packaging machine 39c for producing the contact lens packages in which the manufactured contact lens is inspected and packaged. Another device controller 39d controls a vision system (not shown) that automatically inspects the contact lenses prior to their primary packaging.

Furthermore, in FIGS. 2(a) and 2(b), the existing supervisory control system (control system) 100 includes five (5) types of processing nodes: a Data Acquisition Node 205 for communicating with each of the eight (8) programmable logic controllers (PLCs), discussed above, by means of communication lines 41 and TIWAY adapter card 42, and also, for communicating with the device controllers of the three mold machines, and the vision inspection machine by means of an 8-channel serial card 44, shown connecting the machines by dedicated asynchronous serial lines 43a,b,c, and d; a Relational Database Node 210 which runs relational database software 212 and includes at least three 200 megabyte hard disks provide for off-line data storage consisting of production records and long-term data histories; an Analysis and Routing Node 220 that contains most of the software that is used to initiate data gathering and processing of raw data from the eight PLCs, and, that maintains "real-time databases". The analysis and routing node 220 comprises modules such as: the Statistics Server 225 that stores data within logical user defined groups or datasets, is capable of generating statistics and (optional) alarms on data sets, and, that support statistical control charts and other displays; a poller 226 which coordinates the acquisition of all data from the PLCs, Mold Machines, and the Vision Inspection Machine; a C-language Control Server 228 which is a companion module to the Statistics server and directs the Statistics Server to perform statistical functions needed to support active displays; and, an alarm control server 229 which handles and maintains workcell alarms, warnings, and exceptions that are activated according to defined conditions.

The supervisor system 100 further includes four or more identically-configured Operator Stations 230 that handle the presentation of graphs and displays for the operators of the production line including a module 90 to support lot information entry and lot changes, and for performing contact lens lot tracking and reconciliation as will be described below; and, an Offline Analysis Node 240 that provides for analysis of data collected into the Relational Database Node after the data is no longer on-line, i.e., after a given run of the line. As shown in FIG. 2, ARCNET interface cards 201,211,221, 231, and, 241 are provided for each respective nodes 205,210,220,230,and 240 to support communication between the various nodes via the ARCNET hub 99a. In the preferred embodiment, all of the above-mentioned servers are standard CELLworks software that are commercially available software modules manufactured by FASTech Integration located in Lincoln, Mass.

As mentioned above in view of FIGS. 2(a) and 2(b), there are three types of input sources for the existing Supervisor Controller 100: the eight PLCs, the controllers 39a–d for the Injection Molding, Vision Inspection and primary packaging machines, and, data from the sterilization monitoring node 20. The structures of event blocks and data blocks that the supervisory control system 100 reads from each of the eight PLCs and the Vision Inspection and primary packaging machines are described in detail in the above-mentioned co-pending patent application U.S. Ser. No. 08/257,800, now U.S. Pat. No. 5,461,570. Additionally, as described in detail in the above-identified, co-pending application, a relational database is created that is used to store production records and long-term data histories. The existing supervisory controller system 100 provides for on-line and off-line access to this database and includes the mechanism for generating informative graphs including, but not limited to: scattergrams of process parameters vs. contact lens inspection results, histograms of defects by position on pallet, parieto chart of alarm count and duration by machine, time plot of cumulative inspection results, measured and calculated parameters plotted vs. time as a single trend, wherein trend fixed time scales are available to show data over minutes, hours, days, and weeks.

Sterilization Monitoring Node

Figure 3:
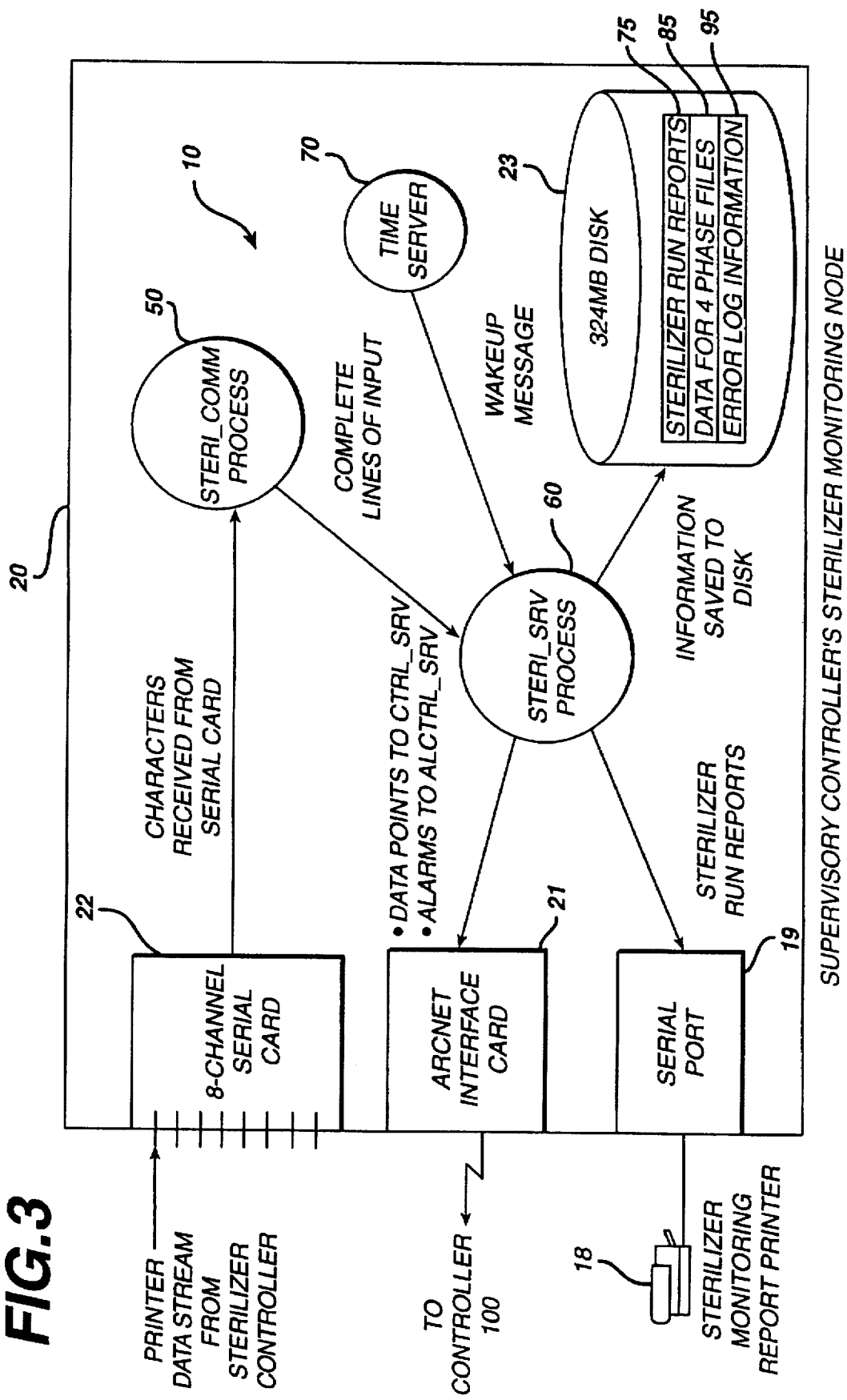
FIG. 3 illustrates a detailed hardware overview of the supervisory controller's sterilizer monitoring node 20 and data flow therein.

As shown in the detailed hardware configuration of FIG. 3, the sterilizer monitoring node 20 interfaces with the existing supervisory system 100 by means of an ARCNET interface card 21 to provide communication with the existing supervisor system. An 8-channel serial card 22, receives serial data from the sterilizer controller 25 from a dedicated asynchronous serial line 16b that is split from the main sterilizer data line output 16 (FIG. 1). A serial port 19 is provided in the node 20 for communication of completed lines of sterilization process data for complete or incomplete sterilizer runs, messages indicating that data is complete or incomplete, or, that a sterilizer run was or was not successful, and error log information and phase file information to the report printer 18 for sterilizer run, error log, and phase file report generation.

The sterilization monitoring process 10 to be described in greater detail hereinbelow comprises two functional modules: the sterilization communications module 50 ("steri comm server") and the sterilization server module 60 ("steri server"). Briefly, the sterilizer communication server 50 functions to receive characters generated by the sterilizer controller via the 8-channel serial card 22. The sterilizer server module 60 processes all of the inputs and produces reports for a variety of users. For instance, as shown in FIG. 3, the sterilizer server 60 processes the information to form sterilizer run reports for printing via serial port 19, and, additionally, generates the sterilization run report file, sterilizer phase report file containing sterilizer phase information of the four major sterilizer phases (heat load, exposure, cool load, and cycle complete), and, error log file for error information all for long term disk storage 23. Preferably, the disk storage capacity is at least 324 MB but this is easily modifiable to any capacity and may constitute any data storage media. Any alarm or process data point that needs to be immediately acted upon, processed, or stored for later off-line analysis is routed to the existing supervisory controller 100 via ARCNET interface card 21 and ARCNET hub 99a (FIG. 1). Details of the sterilization monitoring process 10 and the sterilizer process modules 50, 60 therein will be described in greater detail below.

Sterilizer Controller

Figure 4:
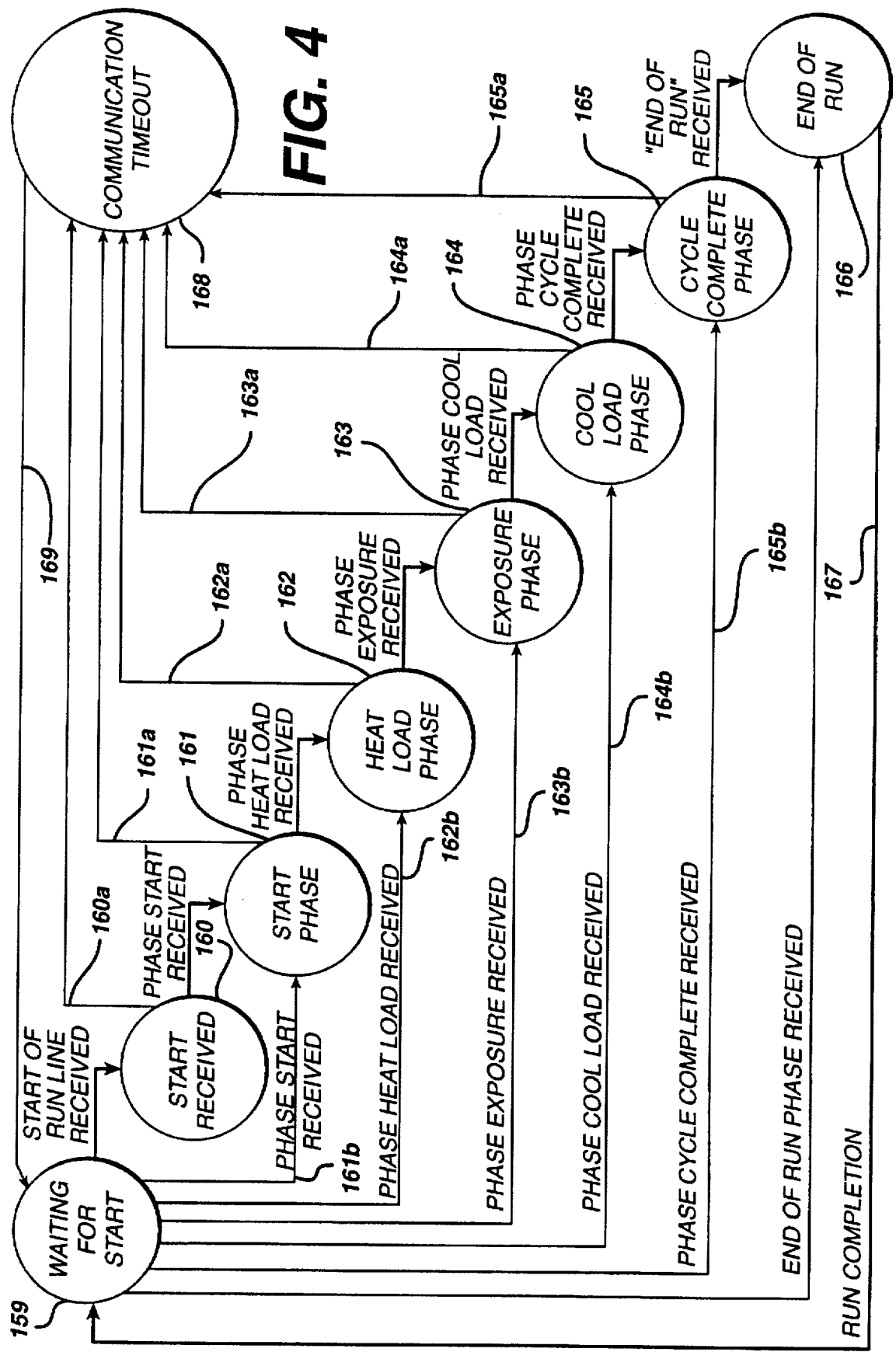
FIG. 4 is a state data flow diagram showing the internal states of the sterilizer monitoring node while receiving data from the sterilizer controller 25.

FIG. 4 illustrates a schematic state diagram showing the internal states of the sterilizer monitor node 20. Barring any alarm errors or communication timeout errors, a normal sterilization run will begin after a batch comprising a quantity ranging from about 1–14,000 individually primary (blister) packaged contact lenses are loaded in the sterilization chamber, in the manner as described in the above-mentioned co-pending patent application U.S. Ser. No. 08/257,788, now U.S. Pat. NO. 5,488,815 entitled "Apparatus and Method for Sterilization and Secondary Packaging". As shown in FIG. 4, a normal sterilization run comprises five consecutive states or phases: A START phase 161, a HEAT LOAD phase 162, an EXPOSURE phase 163, a COOL LOAD phase 164, and, a CYCLE COMPLETE phase 165.

After the node is in a start of run state 160, which is initiated at the start of a run when the sterilizer process hardware including the controller, sterilization chamber, and process devices therein are initialized, the START PHASE state 161, is entered for very short duration while the sterilizer chamber temperature is brought up to the process setpoints. During the HEAT LOAD phase 162 the sterilization chamber attains its maximum operating temperature of approximately 122.5° C., under optimal pressure conditions. In preferred operating conditions, the HEAT LOAD phase is for a duration of approximately five and one-half minutes (5.5 min.). During the EXPOSURE phase 163, as shown in FIG. 4, the batch of lenses are maximally exposed to sterilization conditions for a duration of approximately thirty-one (31) minutes. During the COOL LOAD phase 164, as shown in FIG. 4, a drop of both temperature and pressure conditions in the chamber is effected to enable the batch of lenses to cool for a duration of approximately ten (10) minutes. After the COOL LOAD phase, the sterilizer enters the CYCLE COMPLETE phase 165, where the sterilization process terminates for a time duration of under one minute under normal conditions, and a signal 167 is initiated to put the sterilizer node in a standby or wait state 159. After this phase, the trays containing the now sterilized lenses are positioned for output from the sterilization chamber and the sterilization chamber is either put in an idle or rest state 159 before the next batch of contact lenses is to be sterilized.

As shown in FIG. 4, and, as explained in greater detail below, if an abnormal event (Communication timeout 168) occurs during any of the START CYCLE, HEAT LOAD, EXPOSURE, COOL LOAD, and CYCLE COMPLETE phases, the phase may be interrupted as shown by respective lines 160a, 162a, 163a, 164a, and, 165a as shown in FIG. 4 to indicate that a communication timeout has occurred, i.e., the sterilizer node has not obtained any data for a specified time period, which, in the preferred embodiment, is approximately one line of data every 60 seconds. If the event that caused the timeout is rectified, signal 169 is generated to enable the sterilization monitor node 20 to again process data from the sterilizer controller 25. Since the sterilizer controller 25 was still communicating data during the timeout condition, logic built in to the algorithms explained below will direct the sterilizer node 20, via signals 161b, 162b, 163b, 164b, and 165b, to resume the sterilization monitoring process at the appropriate sterilizer phase.

Sterilization Monitor Processes

As shown in FIGS. 1 and 3, the sterilizer controller 25 provides one way communication with the sterilizer monitoring node 20 through an ASCII data stream on an RS-232 serial interface, and, the sterilizer monitoring node 20 is in two-way communication with the existing supervisory system 100 through the ARCNET hub 99a. In the preferred embodiment, during each of the above-described sterilization phases, the sterilizer controller 25 sends out one line of sterilization process readings at a frequency of preferably once per minute. If an alarm condition exists, as will be explained in further detail below, the sterilization controller 25 will produce and broadcast a line of data at a frequency of once every two seconds.

With regard to FIGS. 1 and 3, there generally illustrates the flow of data to and from the sterilizer monitoring node 20 system for controlling the sterilizer monitoring process. As mentioned above, algorithms are implemented by each of the sterilization monitoring node 20 processing modules, i.e., the sterilization communications server 50 and the sterilization server 60 to enable passive monitoring of all the data information output from the sterilizer and, to communicate the data to the data acquisition and analysis nodes of the existing supervisor system 100. All information generated from the sterilizer controller 25 is serially input to the sterilization communication server 50 of the sterilizer monitor node 20 for data acquisition. Specifically, the sterilization controller 25 broadcasts complete lines of serial data during each phase of the sterilization process to the steri comm server 50. Each line of data will comprise a number of characters, in the form of twelve sterilizer process variable data, alarm information data describing an alarm condition, or, textual information. The steri server 60 incorporates data processing capabilities for processing the input data acquired by the steri comm server 50 to produce sterilizer run files and reports 75, phase files and reports 85, error log files 95, etc., as will be described in greater detail below.

Additionally, as will be explained in greater detail below, the following additional information is input to the sterilizer server module 60: lot number information which is input from the Statistics Server 225 of the existing supervisor system 100; and, time interval wakeup data which is generated on a periodic basis by the time server 70 of the sterilization node 20 for detecting serial communication timeouts. The steri server processor 60 particularly processes this data as well as the real-time raw sterilizer process measurement data, to generate the following: a sterilization run number for storage and subsequent reporting by the statistics server 225 (FIG. 1); alarm messages, for input to the alarm control server 229 (FIG. 1); sterilizer phase file data containing information for each specific phase of the sterilization process for storage in hard disk file 23 (FIG. 3); Sterilization Run Report file information, which is input to the hard disk storage 23 for subsequent generation of sterilizer run reports to be described in detail below; and, sterilizer parameter value information which is input to the control server 228 of the existing supervisor control system 100 (FIG. 1). Each of the above-mentioned sterilizer data processing functions will be described in greater detail below.

Sterilizer Comm Process

Figure 5A:
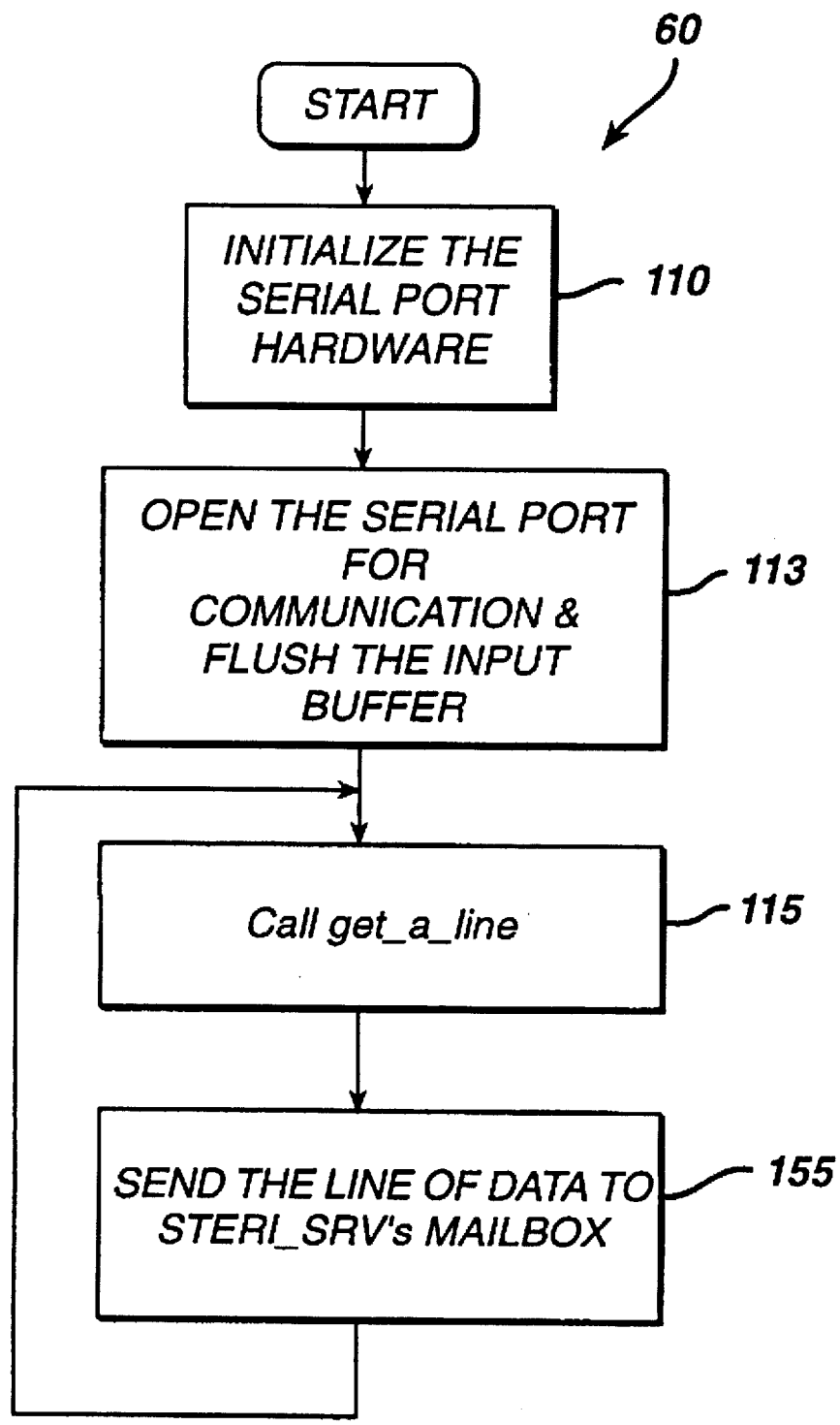
FIGS. 5(a) and 5(b) illustrate, in detail, the steri comm data acquisition process 50.
Figure 5B:
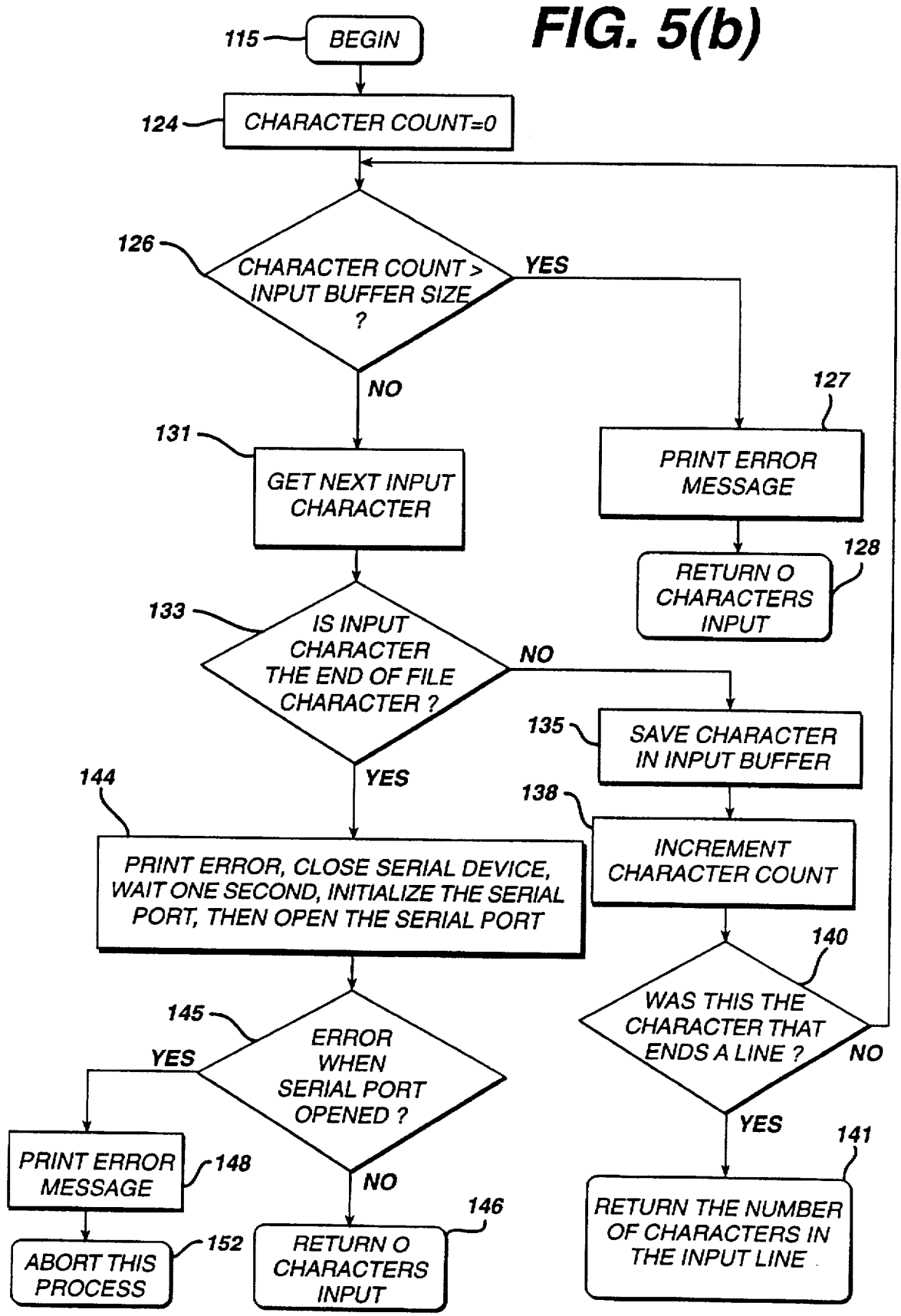

CELLworks system is configured to execute the steri comm server 50 when data is to be received. FIGS. 5(a) and 5(b) illustrate the steri comm data acquisition process 50. The first step of calling the Cellworks steri comm server 50 is to initialize the serial port hardware as indicated as step 110. Next, at step 113 the serial port is opened for communication and the input data buffer (not shown) is flushed. Next, at step 115, the get_a_line function is called by an infinite loop for acquiring a line of serial data from the sterilization controller one character at a time. Specifically, as illustrated in FIG. 5(b), at the first step 124, the character count is initialized to zero. Next, at step 126 the current character count is compared with the size of the input buffer (not shown). If the character count is greater than the input buffer size, then an error message is printed at step 127 and no characters are returned for processing (step 128). As long as the character count is less than the input buffer size, steps 131 and 133 are performed for retrieving each successive character (step 131) and comparing the character to determine if it is an end of file character (step 133). If the character is not the end of file character, then the character is saved in the input buffer at step 135, the character count is incremented at step 138, and a determination is made as to whether the character was an end of line character at step 140. If the character was not the end of line character, then the process returns to step 126 to acquire the next character. If the character was the end of line character, then the process returns the number of characters in the input line (step 141) and the line of data is sent to the steri server's mailbox, i.e., buffer location, at step 155 as shown in FIG. 5(a). When the current character is determined to be the end of file character, this indicates that a serious error has occurred. This may be occur when the serial line is disconnected then reconnected. Therefor, if the current character is determined to be the end of file character at step 133, then, at step 144 of FIG. 5(b), the serial device is closed, reopened, and initialized. At step 145, a determination is made as to whether an error occurred when the serial port was opened. If no error has occurred, then no characters are returned for processing (step 146). If an error has occurred, then an error message is printed at step 149 and the steri comm process 60 is aborted at step 152.

Sterilizer Server Process

Figure 6:
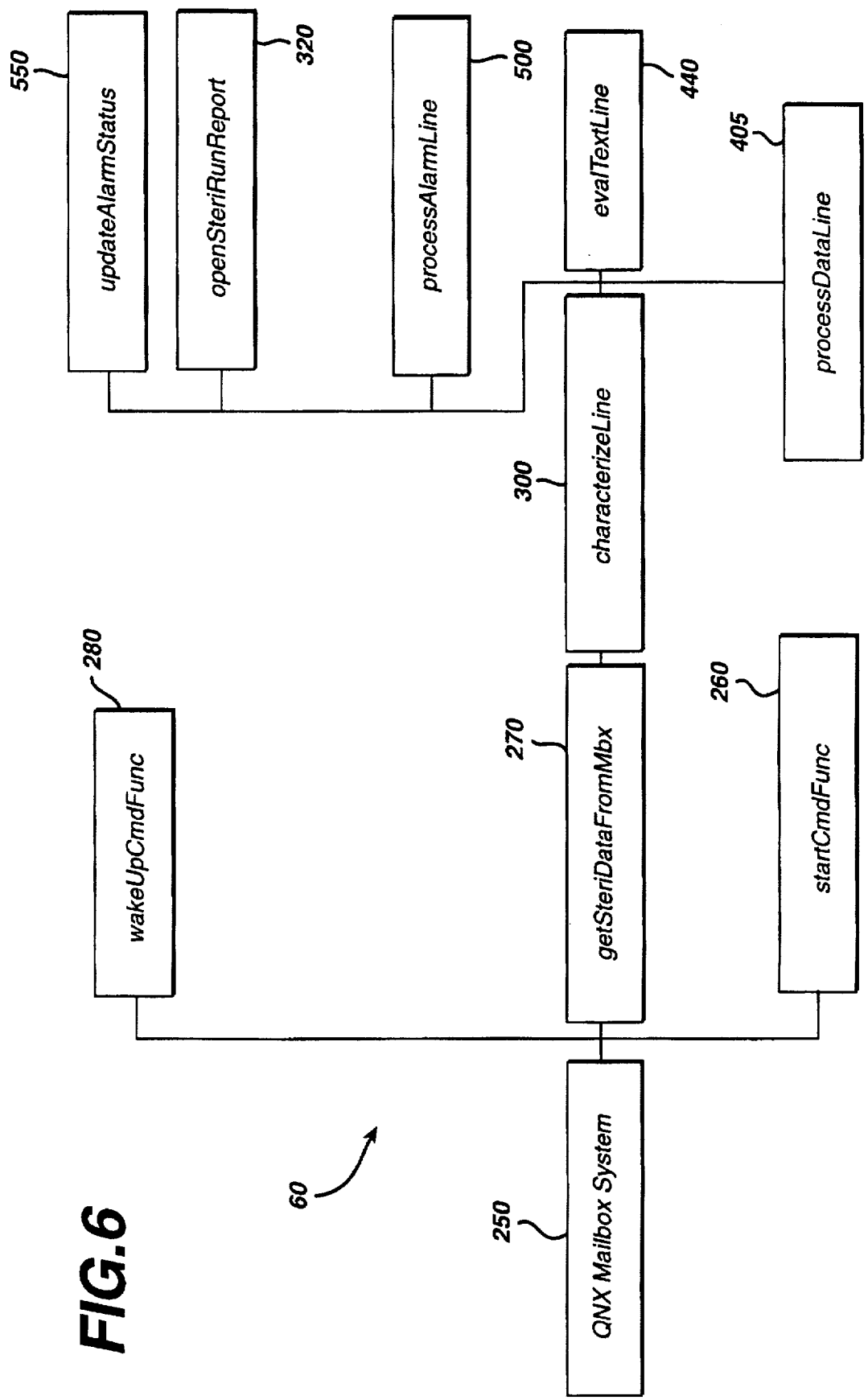
FIG. 6 illustrates the major functional blocks of the steri server process 50.

FIG. 6 illustrates the major functional blocks of the steri server process 60 which comprises a steri server QNX Mailbox System, indicated as element 250. The QNX Mailbox System is the primary message routing engine for the node, and, each server in the sterilizer node 20 is provided with a mailbox that accepts and sends command or data messages. Depending upon the source of the message, the steri server process 60 will implement either of three functions: startCmdFunc 260; getSteriDataFromMbx 270; and, wakeUpCmdFunc 280, as illustrated in FIG. 6 and explained in further detail below.

The CELLworks system is configured upon startup to execute the startCmdFunc 260 when the command to start steri server process 60 is received. This function ensures that the steri server 60 and internal variables therein are initialized and that all the QNX communication mailboxes (not shown) are setup. Additionally, an entry is placed in the error log file 95 (FIG. 3) to indicate that the system has started up, and, a request is made for a future wake-up message from the Time Server 70 at a prespecified time.

CELLworks is configured to implement the calling of the getSteriDataFromMbx functional block 270 whenever a message comprising the complete line of data from the sterilizer comm process 50 appears in the Steri Server mailbox. The getSteriDataFromMbx process 270 functions to copy the message from the mailbox into local steri server input buffer (not shown) and initiate the processing of the message. Additionally, a check is made to determine if the proper message line ending is present. The getSteriData-FromMbx functional block 270 calls the characterizeLine algorithm 300 for determining the nature of the line of sterilizer data information sent from the sterilization monitor only if the proper message line ending is present. As will be explained below, determining the nature of the line of sterilizer data information and the processing of this data will involve one or more of the following functions: evalTextline indicated as block 440; precessDataLine indicated as block 405; processAlarmLine indicated as block 500; openSteriRunReport indicated as block 320; and, updateAlarmStatus indicated as block 550.

As shown in FIGS. 7(*a*) and 7(*b*), the first step 302 of the characterizeLine algorithm 300 is to record the current time to aid in the detection of a possible communication timeout. The next step 304 is to massage the line of data to remove spurious printer control characters sent by the sterilization monitor that could interfere with characterization of the line as a line of data. Next, at step 306, a determination is made as to if there are any printable characters in the line and whether a sterilizer run report file 85 has not been opened. If there are printable characters in the line and a sterilizer run report file has not been opened, then the openSteriRunReport ("steri run report") file algorithm is implemented at step 320.

Figure 7A:
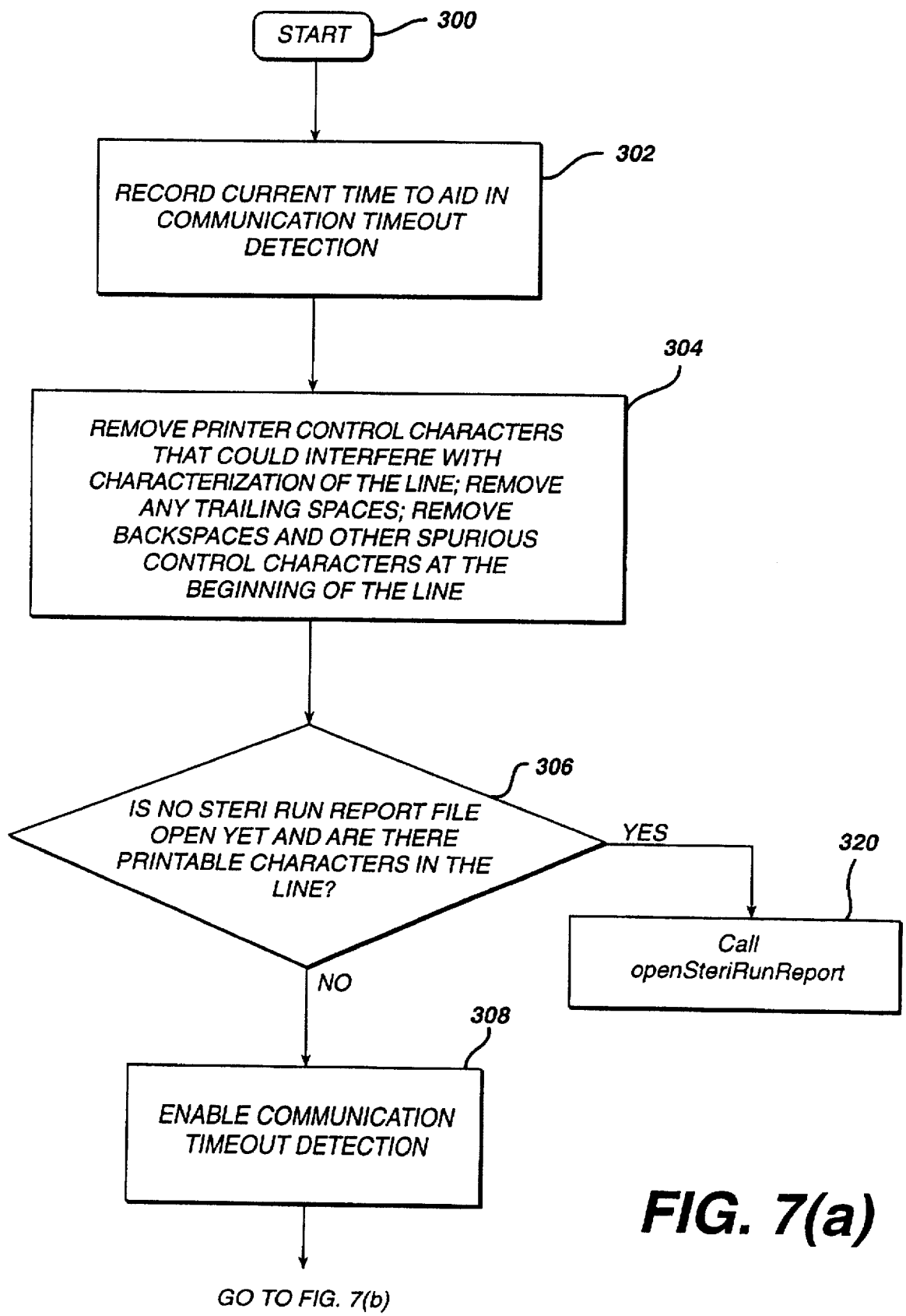
Figure 19:
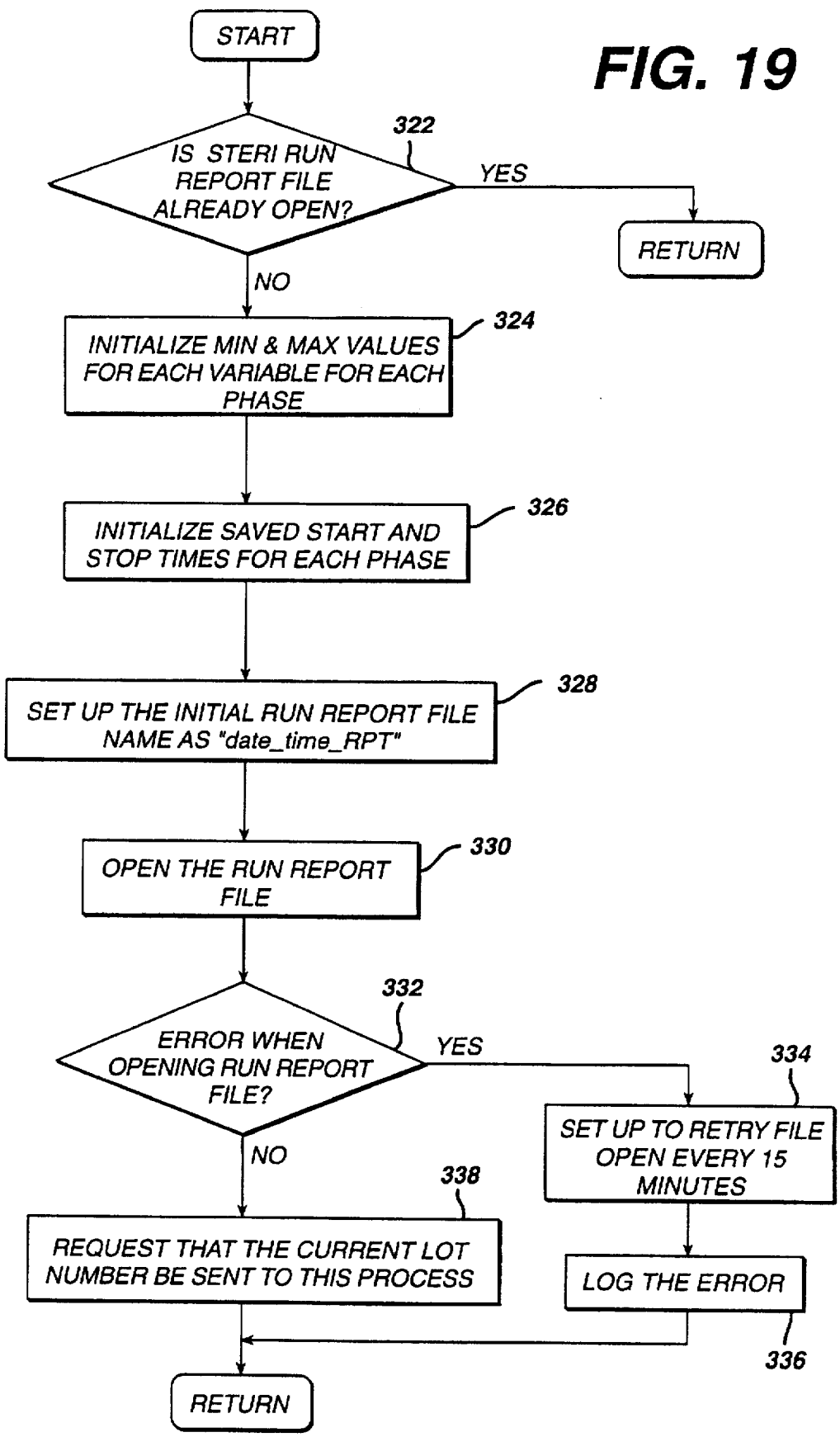
FIG. 19 illustrates the openSteriRunReport procedure for opening the steri run report file.

The procedure for opening the steri run report is illustrated in FIG. 19, and as a redundant check the first step 322 is to determine if the steri run report file is already opened. If the steri run report file is open the process will return to step 308 of the characterizeLine process (FIG. 7*a*). If the file is not open, then the following steps are performed prior to opening up the steri run report file at step 330: First, at step 324, the minimum and maximum values for each variable of each phase of the sterilizer is initialized. Then, at step 326, the saved start and stop times for each phase are initialized for later calculation of phase duration explained in detail below. Next, at step 328, the initial run report file is set up with a default name comprising the current date and time, "date_time_RPT", as indicated. At step 330, the run report file is opened. If it is determined at step 332 that an error has occurred when opening up the report file, then, at step 334, a retry file is set up to open every 15 minutes in the preferred embodiment, and, at step 336, the error is logged in the log report file. If it is determined at step 332 that an error has not occurred when opening up the report file, then, at step 338, a request is made for the previously entered lot number to be sent to this process from the statistics server, and the process returns to the line characterization algorithm (FIGS. 7*a* and 7*b*).

If a steri run report file has already been opened in FIG. 7*a*, then communication timeout detection is enabled at step 308. The algorithm then proceeds by determining at step 310 if the line begins with a time signature of the form:

hh:mm:ss (hours,minutes, seconds)

If the line does begin with such a time signature, then the processDataLine algorithm is invoked at step 405 indicating that the data line contains process variable data including twelve (12) variables of sterilizer phase data. Else, at step 312, a determination is made as to whether an alarm condition exists. If an alarm condition exists, then the processAlarmLine algorithm is invoked at step 500 for processing the alarm data and updating the alarm control server of the existing supervisor system 100. If the line of data is determined to be textual in nature, then the evalTextLine algorithm is invoked at step 450, for processing the text data. Whenever the processing of an incoming line has been completed, the updateAlarmStatus process is called at step 550 to the check whether the alarm status has changed.

Figure 8:
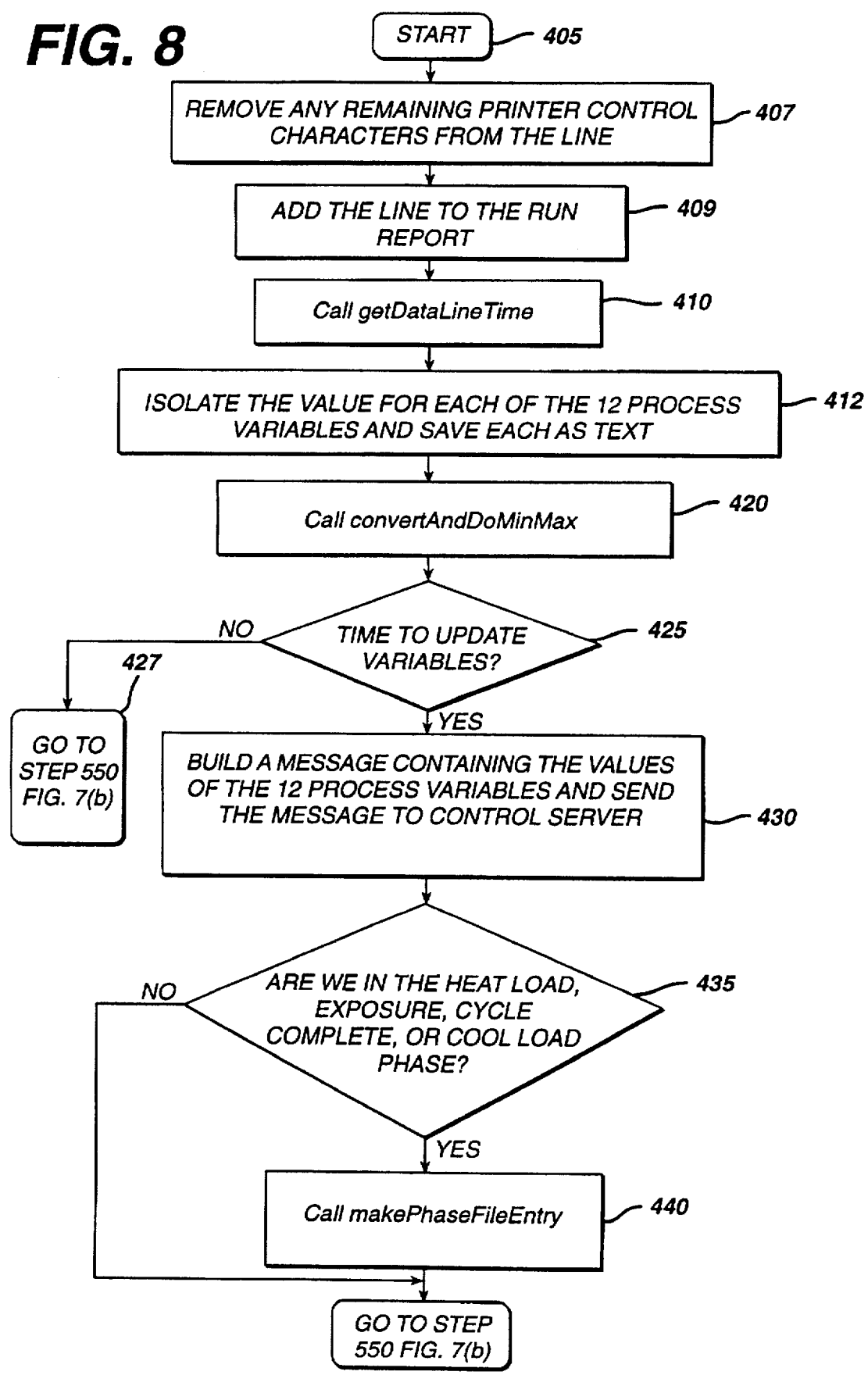
FIG. 8 illustrates the processDataLine algorithm 405 for processing the twelve (12) variables of sterilizer phase data from the data line.

FIG. 8 illustrates the processDataLine algorithm 405 for processing the twelve (12) variables of sterilizer phase data from the data line. After removing any other remaining printer control characters from the line at step 407, the line of data is added to the steri run report at step 409. Next, the getDataLinetime algorithm is invoked at step 410 to ensure that, for each of the five sterilizer phases, the start time of the current operating phase in addition to the phase stop time of the previous sterilizer phase has been recorded in the appropriate phase file. Next at step 412, the 12 process variable values of the current data line are isolated and saved as text. Then, the convertAndDoMinMax algorithm is called at step 420 for converting each of the sterilizer process readings from text format to floating point format, and, updating the maximum and minimum values for each of the twelve variables for the current sterilizer phase. At step 425, it is determined if it is time to update the variables in the phase files. If not, the process returns to the characterizeLine algorithm as indicated at step 427. If it is time to update the variables, then at step 430, a message will be formulated and sent to the control server 228 of the existing supervisor control system 100 to make the twelve floating process variables available for display, trending, and inclusion in the engineering database (not shown) in the manner as explained in detail in the above-mentioned copending patent application U.S. Ser. No. 08/257,800. A determination is then made at step 435 whether the current sterilizer phase is in the heat load, exposure, cycle complete or cool load phase. If the sterilizer is in one of these phases, then the makePhaseFileEntry process is called at step 440. If the sterilizer is not in one of these phases, then a return is made to the calling characterizeLine algorithm 280.

Figure 9:
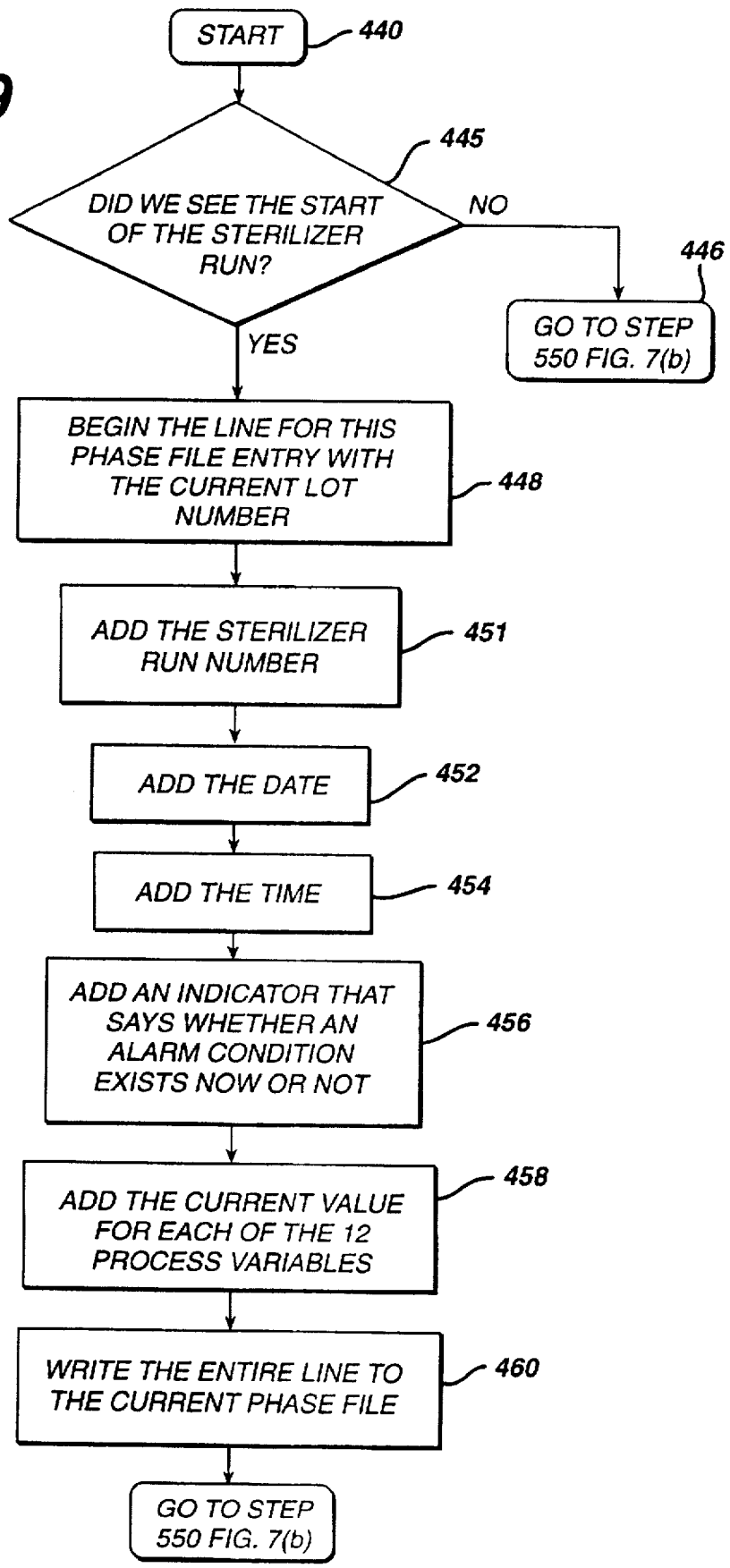
FIG. 9 illustrates the makePhaseFileEntry algorithm 440 to format the process variable information for entry as a line in the corresponding phase file.

As shown in FIG. 9, the makePhaseFileEntry process 440 is called from the Process Data line algorithm 405 to format the process variable information for entry as a line in the corresponding phase file. In the preferred embodiment, there is a separate phase file on disk for each of the four major sterilizer phases. When a new entry is made, it is added to the end of the appropriate phase file as follows: First, at step 445, it is determined if process data has been obtained from the start of the sterilizer run. If not, then the process will return to the processDataLine algorithm at step 446. If the current phase has started from the start cycle, then the following information is gathered in line format: the current lot number at step 448; the sterilizer run number at step 451; the date at step 452; the time at step 454; an indicator to convey whether an alarm condition currently exists or not at step 456; and, the current twelve process values for the current sterilizer run at step 458. Finally, at step 460, the entire line is written to the current phase file.

FIG. 31 illustrates the format of the above described entries of a phase file 876 for storing sterilizer phase information. Each row in the table of FIG. 31 illustrates represents one entry in the phase file. The lot numbers are entered by the operators on the operator stations 230 (FIG. 1) of the supervisory controller, and, the "mode" entry is a single character designation of whether the sterilizer controller indicated an alarm at that time or not.

Returning to the characterizeLine algorithm 300 as shown in FIG. 7(*a*) and 7(*b*), if the data obtained from the sterilizer controller is not alarm data or process variable data, then the evalTextline is called at step 450 to process the line of text.

FIGS. 10(*a*) and 10(*b*) and 10(*c*) illustrate the evaluateTextline process 450 for processing textual data from the input data line. The first step 461 of the evaluate text line process is to remove any remaining printer control characters from the line, and, at step 462, adding the line to the steri run report. A determination is made at step 463 if the text indicates the start of a sterilizer run. If so, then a StartOfRunEvent procedure is called at step 465 to perform the following steps as shown in FIG. 11: First, at step 467, an entry into the error log 95 (FIG. 3) is made indicating that the sterilizer run has started. Then, at step 468, a flag is set to indicate that the current run has started from the beginning (start of sterilizer run) and, at step 469, that the current state is the start of run state. Next, at step 470 of FIG. 11, a message is sent to the control server of the existing supervisor system that the current state of the sterilizer is the start of run state and the process returns to characterize the next line of data (FIGS. 7(a) and 7(b)).

Figure 10A:
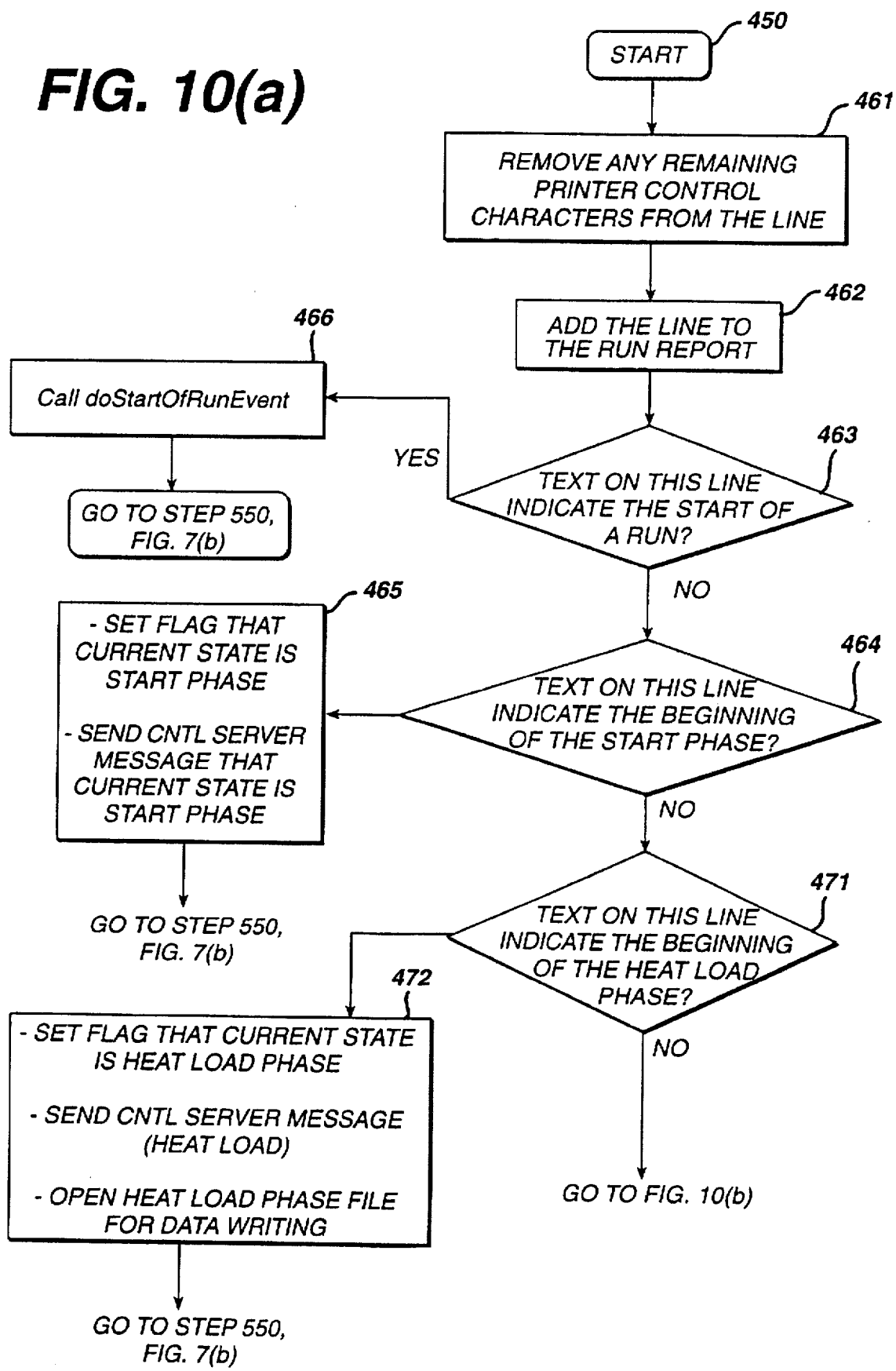
FIGS. 10(a) and 10(b) and 10(c) illustrate the evaluateTextline process 450 for processing textual data from the input data line.
Figure 10B:
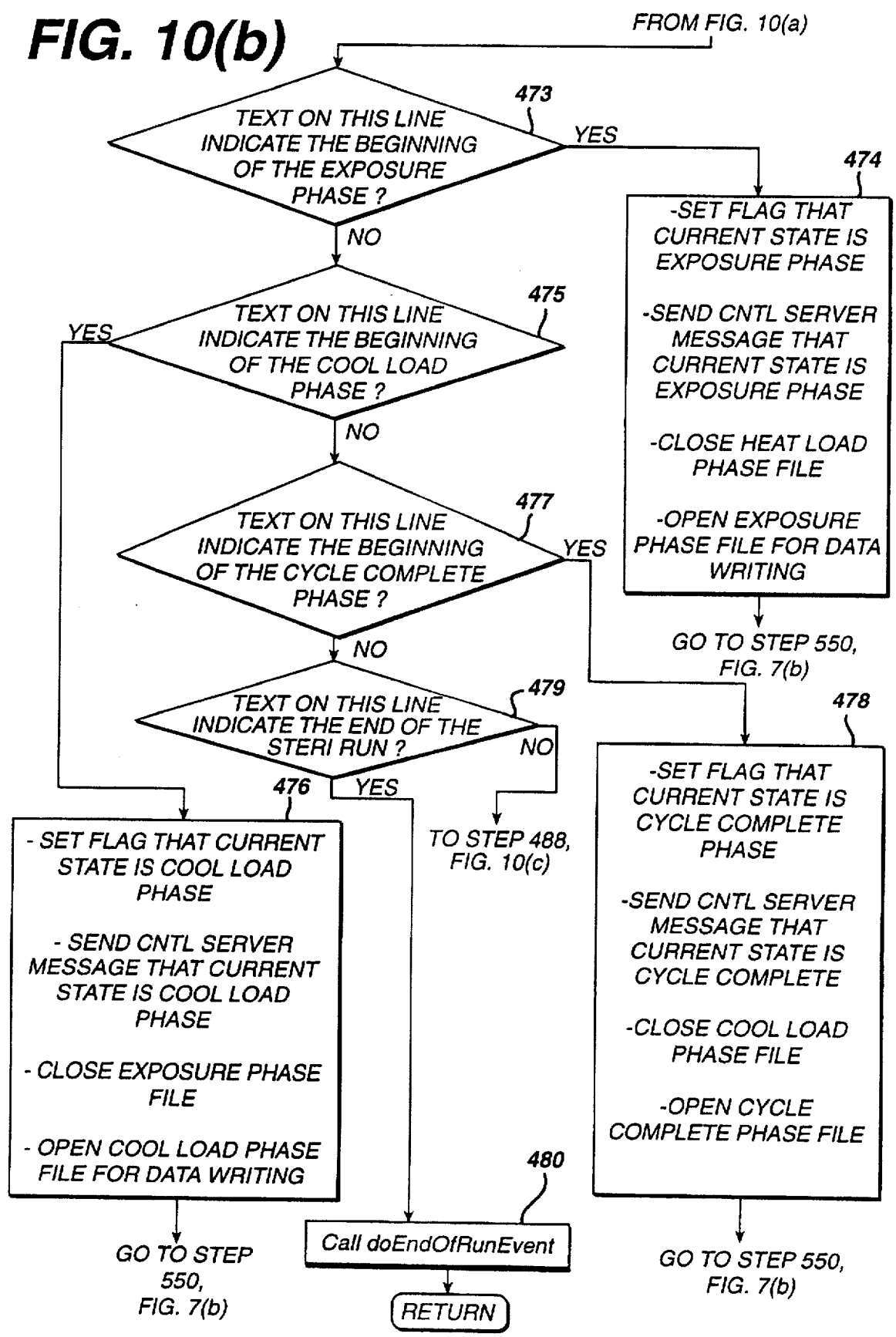
Figure 11:
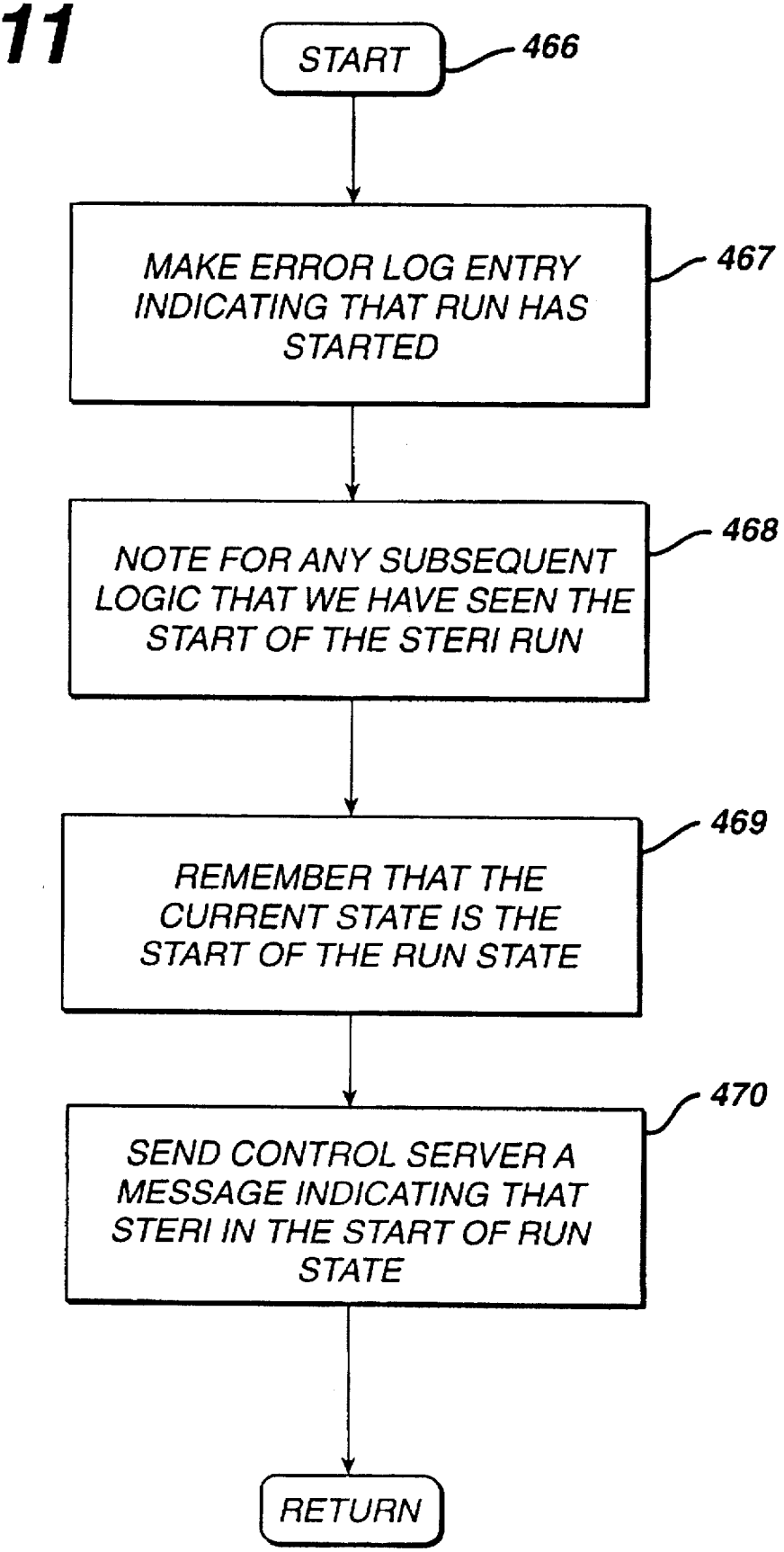
FIG. 11 illustrates the StartOfRunEvent procedure 466 invoked when a sterilizer run has started from the beginning.

In FIG. 10(a), if the text did not indicate the start of a sterilizer run at step 463, then, at step 464, a determination is made if the text indicates the beginning of the start phase. If the text indicates the beginning of the sterilizer start phase, then the doStartPhaseEvent procedure is called at step 465 to set a flag that the current state is the sterilizer start phase, and, to send a message to the control server of the existing supervisor system that the current state is the sterilizer start phase state before returning to characterize the next line of data (step 550, FIG. 7(b)).

If the text did not indicate the beginning of the sterilizer start phase at step 464, then, at step 471, a determination is made if the text indicates the beginning of the sterilizer heat load phase. If the text indicates the beginning of the sterilizer heat load phase, then the doHeatLoadPhaseEvent procedure is called at step 472 to set a flag that the current state is the sterilizer heat load phase, and, to send a message to the control server of the existing supervisor system that the current sterilizer state is the heat load phase. Additionally, the HeatLoad phase file is opened for writing data thereto and the procedure returns to characterize the next line of data.

If the text did not indicate the beginning of the heat load phase at step 471, then, at step 473, a determination is made if the text indicates the beginning of the sterilizer exposure phase. If the text indicates the beginning of the sterilizer exposure phase, then the doExposurePhaseEvent procedure is called at step 474 to set a flag that the current state is the sterilizer exposure phase, and, to send a message to the control server of the existing supervisor system that the current state is the sterilizer exposure phase. Additionally, before returning to characterize the next line of data, the Heat load phase file is closed and the Exposure phase file is opened for writing the data thereto.

If the text did not indicate the beginning of the sterilizer exposure phase at step 473, then, at step 475, a determination is made if the text indicates the beginning of the sterilizer cool load phase. If the text indicates the beginning of the sterilizer cool load phase, then the doCoolLoadPhaseEvent procedure is called at step 476 to set a flag that the current state is the sterilizer cool load phase, and, to send a message to the control server of the existing supervisor system that the current state is the sterilizer cool load phase. Additionally, before returning to characterize the next line of data, the Exposure phase file is closed and the Cool load phase file is opened for writing the data thereto.

If the text did not indicate the beginning of the sterilizer cool load phase at step 475, then, at step 477, a determination is made if the text indicates the beginning of the sterilizer cycle complete phase. If the text indicates the beginning of the sterilizer cycle complete phase, then the doCycComplPhaseEvent procedure is called at step 478 to set a flag that the current state is the sterilizer cycle complete phase, and, to send a message to the control server of the existing supervisor system that the current state is the sterilizer cycle complete phase. Additionally, before returning to characterize the next line of data, the Cool load phase file is closed and the Cycle Complete phase file is opened for writing the data thereto. Then, the process returns to step 550, FIG. 7(b) to characterize the next line of data.

Figure 12:
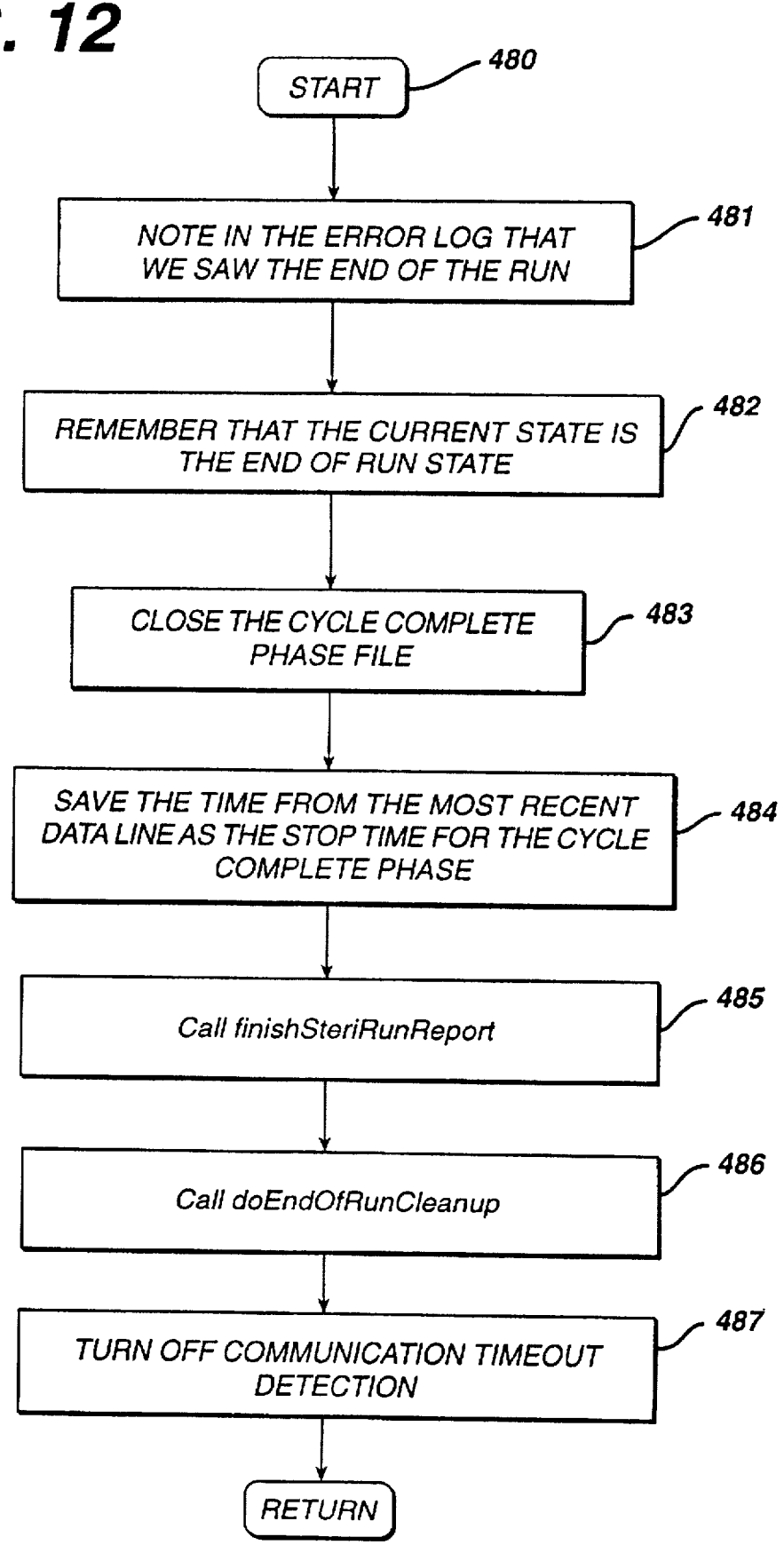
FIG. 12 illustrates the doEndOfRunEvent procedure 480 invoked when the end of a sterilizer run has been detected.

If the text did not indicate the beginning of the sterilizer cycle complete phase at step 477, then, at step 479, a determination is made if the text indicates the end of the sterilizer run. If it is the end of a sterilizer run, then a doEndOfRunEvent procedure is called at step 480 to perform the following steps as shown in FIG. 12. First, at step 481 of FIG. 12, an entry is made in the error log that the sterilizer run has ended. Then, at step 482, a flag is set to indicate that the current state is the end of run state. Next, at step 483 of FIG. 12, the Cycle Complete phase file is closed. At step 484, the time of the most recent data line is saved as the stop time for the Cycle Complete phase. Then, at step 485, the finishSteriRunReport procedure is called to generate the sterilizer run report as will be explained in greater detail below. Another procedure indicated as the doEndOfRunCleanup is performed at step 486 to finish the text line processing and print the steri run report as explained in greater detail below. Finally, at step 487, since it is not known when the next sterilizer run will begin, the communication timeout detection is disabled.

Figure 10C:
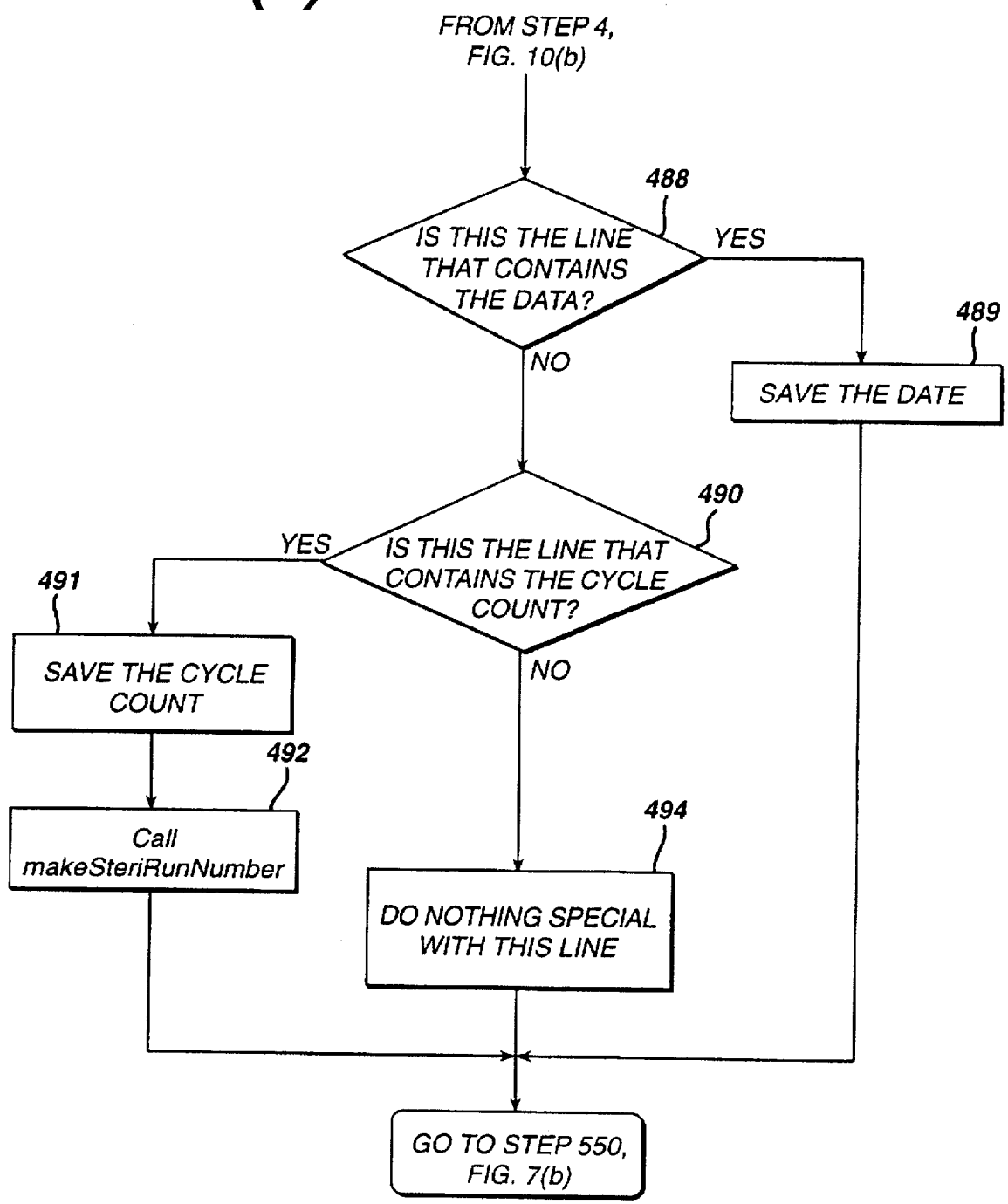

Referring back to FIG. 10(b), if the text did not indicate the end of the sterilizer run at step 479, then, at step 488, FIG. 10(c), a determination is made if the current text line indicates the date. If the current line does indicate the date, then the date is saved at step 489 and the process returns to the evaluate text line procedure. If the current line does not indicate the date, then, at step 490, a determination is made if the current text line contains the cycle count. If the current line does contain the cycle count, then the count is saved at step 491 and the makeSteriRunNumber procedure is called at step 492 for building the sterilization run number and sending the sterilization number to the control server of the existing supervisor system. In the preferred embodiment, the sterilization run number is put together as a combination of the date, sterilizer number, and the sterilizer cycle count and is of the form:

YP1NNNN where Y is the last digit of the year, P1 is the sterilizer number of the production line, and, the NNNN is the sterilizer cycle count. After the sterilization run number is obtained, the process returns to the line characterization algorithm.

If the current line does not contain the cycle count, then nothing is done with the line as indicated as step 494, and the process returns to the calling characterizeLine algorithm (step 550, FIG. 7(b)).

Figure 13:
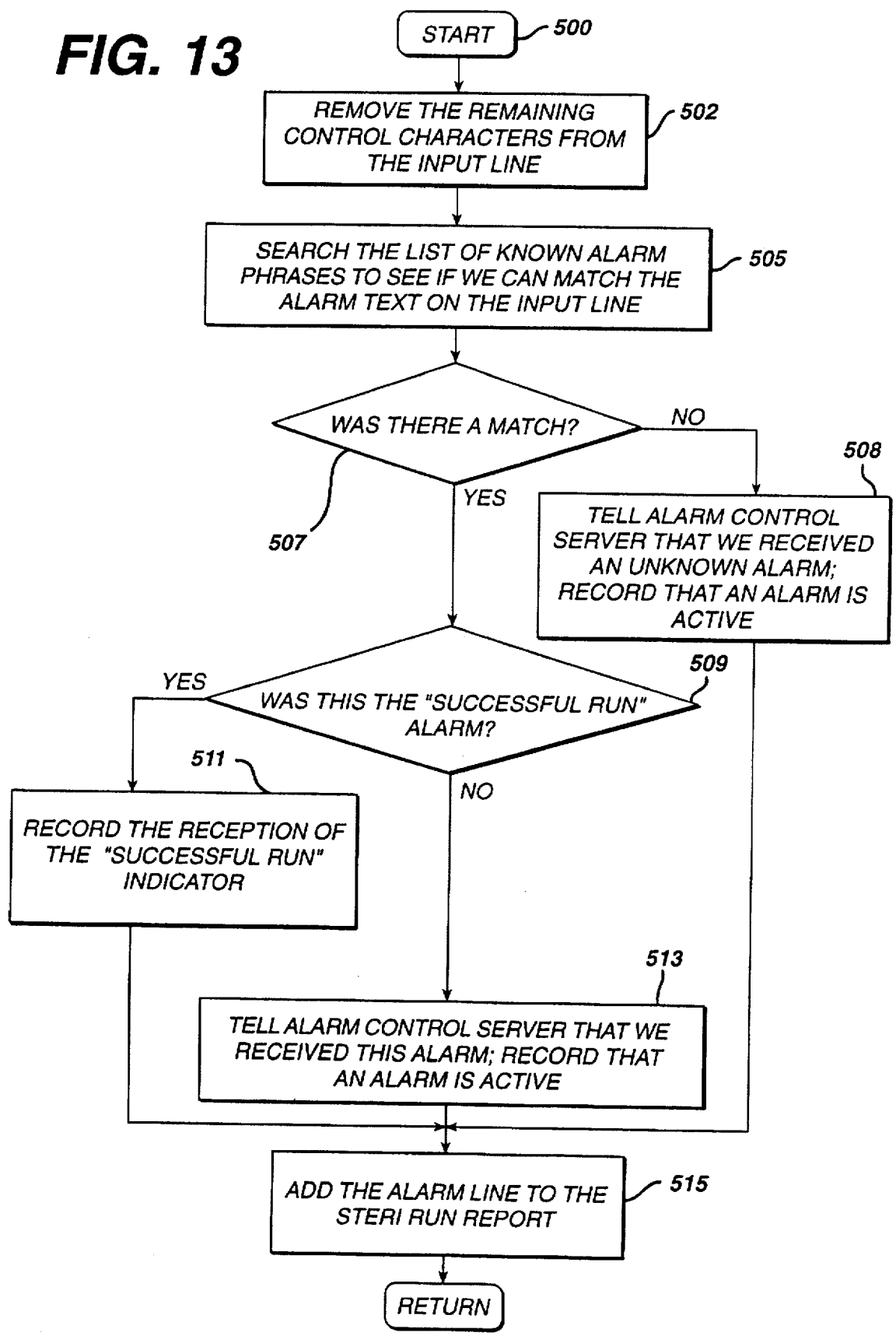
FIG. 13 illustrates the precessAlarmLine algorithm 500 for processing alarm data from the input data line.

FIG. 13 illustrates the processAlarmLine algorithm 500 for processing alarm data from the serial data line. After removing any other remaining printer control characters from the line at step 502, a list of known alarm phrases is searched at step 505 to indicate if a known alarm condition exists. Table 1 and Table 2 below indicates various alarm phrases and alarm code data:

TABLE 1

| Alarm Text from Sterilizer Controller | Alarm Code |
| --- | --- |
| CLEAN STEAM LOW | 1 |
| COLD WATER LOW | 2 |
| COMP. AIR LOW | 3 |
| CYCLE ABORT | 4 |
| DOORS NOT CLSD | 5 |

TABLE 1-continued

| Alarm Text from Sterilizer Controller | Alarm Code |
|---|---|
| DOORS NOT SEALED | 6 |
| FAN FAILURE | 7 |
| HIGH TEMPERATURE | 8 |
| HIGH WATER | 9 |
| LOW TEMPERATURE | 10 |
| OVER PRESSURE | 11 |
| PLANT STEAM LOW | 12 |
| POWER FAIL | 13 |
| PRES SENS. ERROR | 14 |
| PT ISOLATED | 15 |
| SAM FAILURE | 16 |
| STEAM FAILURE | 17 |
| TEMP SENS. ERROR | 18 |
| UNDER PRESSURE | 19 |
| unknown alarm: this code used when there is alarm text that is not recognized | 999 |

TABLE 2

| Condition Detected by Sterilizer Monitor Server | Alarm Code |
|---|---|
| Communication timeout with sterilizer controller | 01 |

If the alarm condition is unknown, i.e., a match is not found between the alarm data phrase and the alarm phrase table at step 507, then, at step 508, a communication is made to the alarm control server of the existing supervisor system that an unknown alarm has been received and an active alarm condition is recorded. The process then proceeds to step 515 to add the alarm line to the steri run report. If a known alarm condition exists, i.e., a match is found between the alarm data phrase and the alarm phrase table at step 507, a determination is made at step 509 if the alarm indicates a successful run. If the indicator is a successful run alarm, it is recorded at step 511 and the alarm line is added to the steri run report at step 515. If the indicator is not a successful run alarm, then, at step 513, a communication is made to the alarm control server of the existing supervisor system which alarm condition has occurred and it is recorded that an active alarm condition exists. Finally, at step 515 the alarm line is added to the steri run report and the process returns to the calling characterizeLine algorithm.

Figure 14:
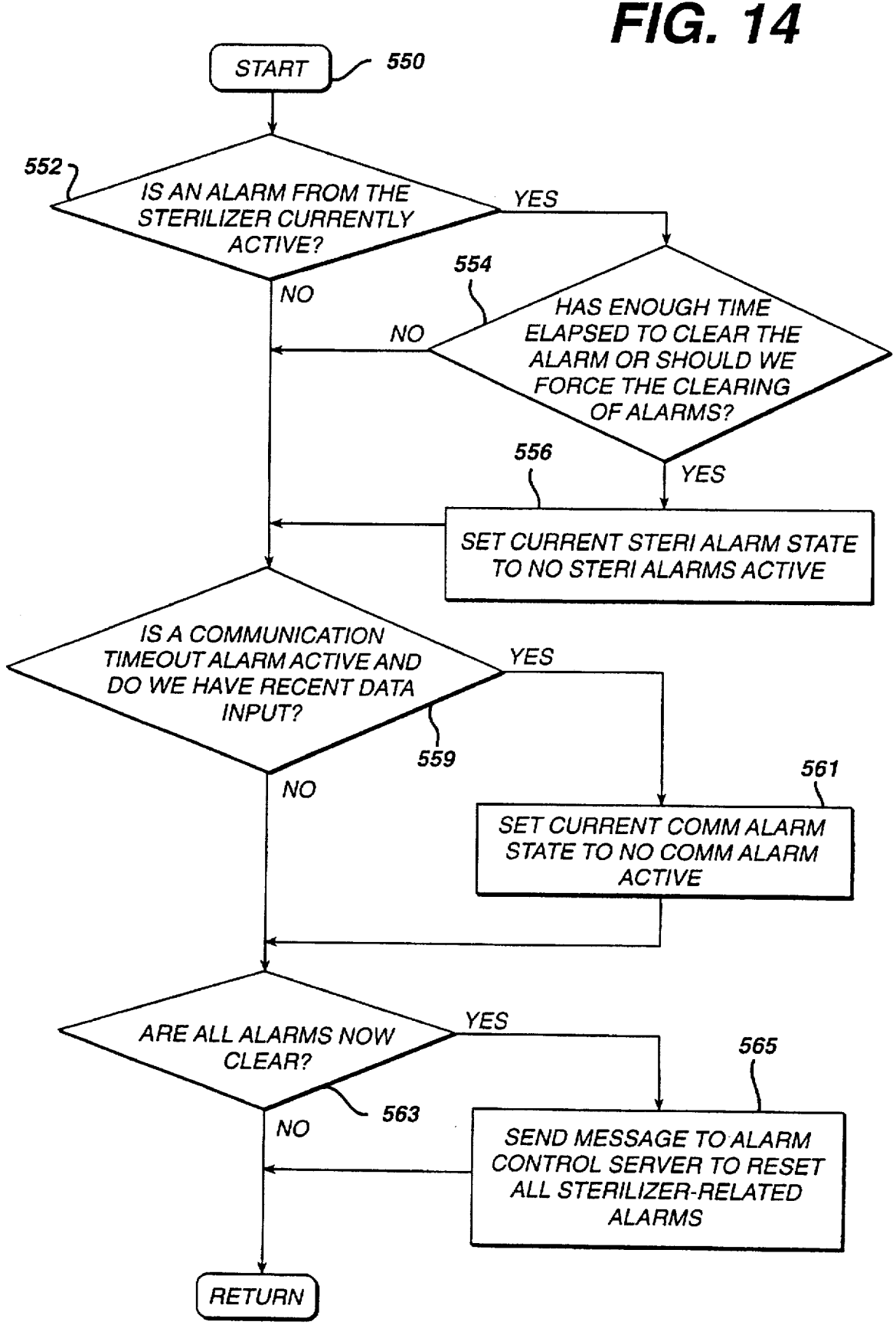
FIG. 14 illustrates the updateAlarmStatus algorithm 550 for updating alarm status after every line evaluation.

As mentioned above in view of FIGS. 7(a) and 7(b) illustrating the characterizeLine algorithm, after a line is characterized and process variable data, alarm data, or textual data information is processed, the alarm status is updated by invoking the updateAlarmStatus process at step 550. FIG. 14 illustrates the updateAlarmStatus function in detail. The first step, indicated as step 552, is to determine the status of a parameter (not shown) that is supplied indicating if any alarm from the sterilizer controller is currently active, and, sending data lines every two seconds as described above. If so, then at step 554, a determination is made whether there is enough time to clear the alarm or whether the currently active alarm should be cleared by force. If not enough time has elapsed to clear the alarm, i.e., if the time between the last sterilizer data entry and the previous data entry is two (2) seconds indicating that the alarm condition should be cleared by force, then, at step 556, the current sterilizer alarm state is set to indicate that no steri alarms are active. If there is enough time to clear the alarm, i.e., the time between the last sterilizer data entry and the previous data entry is greater than two (2) seconds indicating that the alarm condition data is not to be cleared by force, then a determination is made at step 559 if a communication timeout alarm is active and if recent data has been input. As mentioned above, a communication timeout alarm occurs when data is received at an interval greater than one minute, for e.g., when the serial data line is temporarily disconnected. If a communication timeout alarm is active and recent data has been input, then at step 561, the current communication alarm state forced to indicate that no communication alarms are active and is set to provide such indication. If a communication timeout alarm is not active or, recent data has not been input, for e.g., end of a run, a determination is made at step 563 if all alarms are cleared. If all alarms are currently cleared, then at step 565, a message is sent to the alarm control server of the existing supervisor system to reset all sterilizer related alarms. Else, if all alarms are not clear the program returns to the calling characterize line process.

Figure 15:
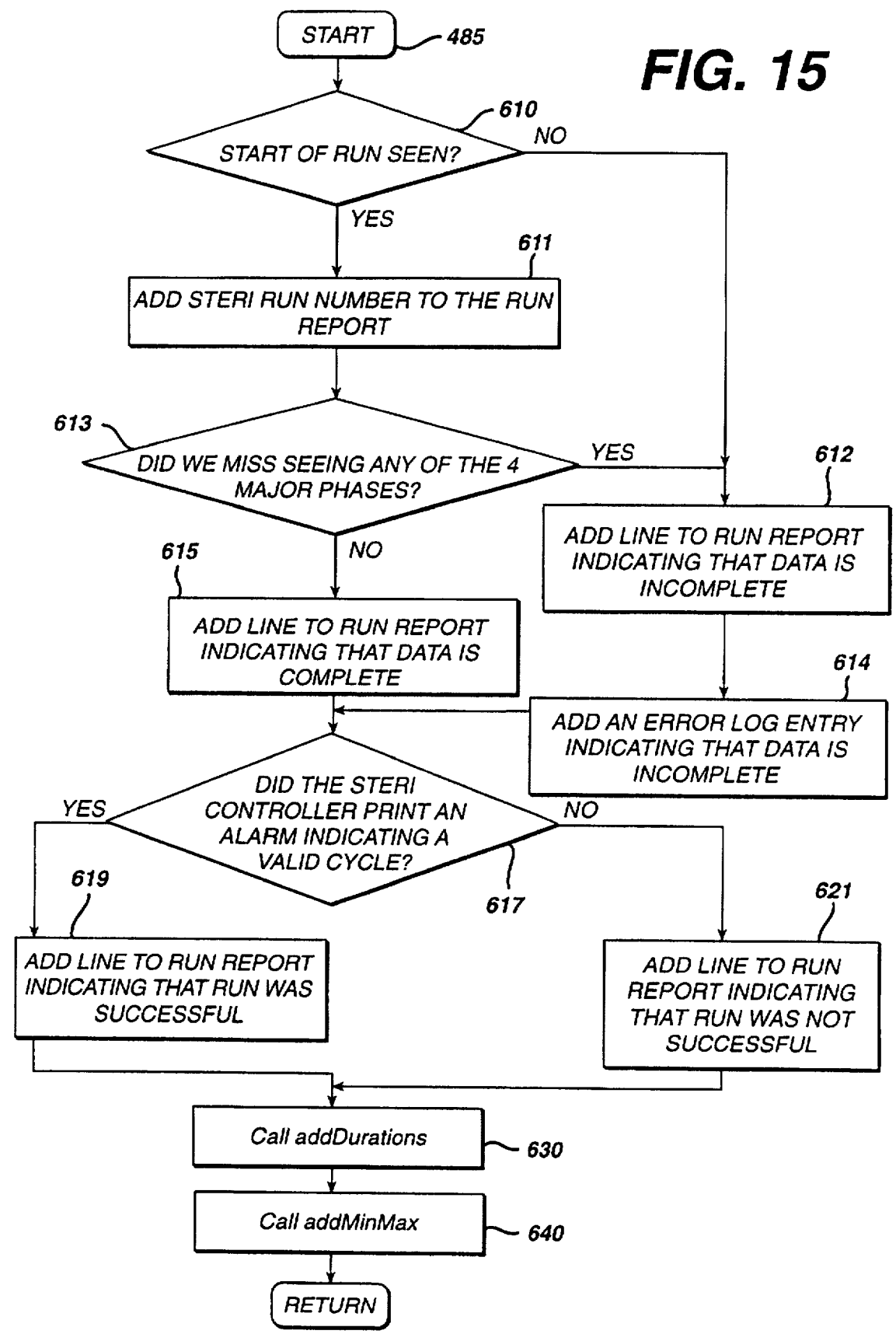
FIG. 15 illustrates the finishSteriRunReport procedure 485 to generate the sterilizer run report.

Referring back to FIG. 12, at step 485, the finishSteriRunReport procedure 485 is invoked when the end of a sterilizer run is detected. As shown in FIG. 15, the first step 610 of the finishSteriRunReport procedure is to determine if the flag to indicate that the current run has started from the beginning (start of sterilizer run) had been set as indicated above with respect to step 468, FIG. 11. If the flag indicating that the cycle has started from the beginning of the sterilization run is not set, then, at step 612, a line is added to the sterilization run report indicating that the data is incomplete, and, at step 614, an entry is made to the error log indicating that the data is incomplete. The process then resumes to step 617. If the flag indicating that the cycle has started from the beginning of the sterilization run is set, then, at step 611, the sterilization run number is added to the steri run report. Next, at step 613, a determination is made as to whether any of the four major sterilization phases has been missed. If any of the four sterilization phases has been missed in the current run, then a line is added to the sterilization run report indicating that the data is incomplete (step 612), and, an entry is made to the error log indicating that the data is incomplete (step 614). If none of the four sterilization phases has been missed in the current run, then, at step 615, a line is added to the sterilization run report indicating that the data is complete. The next step, indicated as step 617 in FIG. 15, is to determine if the sterilization controller issued a successful run alarm indicating a valid cycle as described above at step 511, FIG. 13. If a successful run alarm indicating a valid cycle has been generated by the sterilization controller, then, at step 619, a line is added to the sterilization run report indicating that the run was successful. If a successful run alarm indicating a valid cycle has not been generated by the sterilization controller, then, at step 621, a line is added to the sterilization run report file indicating that the run was NOT successful. Finally, at step 630, a procedure is called to add the time durations for each of the major sterilization phases to the steri run report file, and, at step 640, a procedure is called to add the minimum and maximum values of the process variables for each of the major sterilization phases to the steri run report file.

Figure 17:
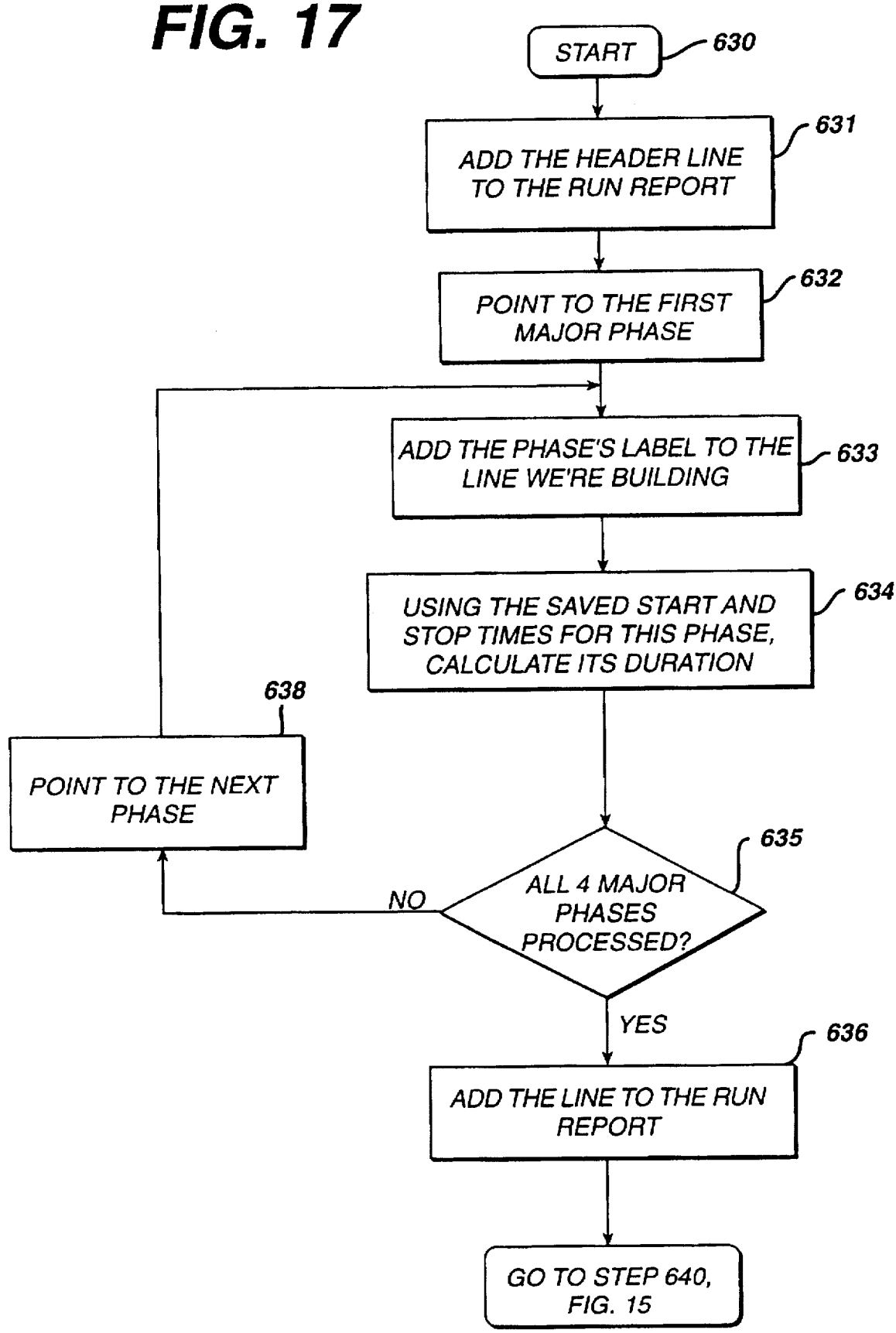
FIG. 17 illustrates the addDurations procedure 630 for adding the phase time durations to the sterilizer run report.

The addDurations procedure 630 of the finishSteriRunReport procedure begins by adding the Phase Duration header line of the sterilization run report as indicated as step 631 of FIG. 17. Next, a pointer is set to the first of the four major phases, as indicated at step 632. The following steps indicate the printing of phase durations: At step 633, a label for the phase duration is obtained; then, at step 634, the phase duration is calculated using the saved phase start and stop times obtained at step 326 of the openSteriRunReport algorithm (FIG. 19). Next, a determination is made at step 635 as to whether the phase duration values for all four major sterilizer phases have been processed. If the phase duration values for all four major sterilizer phases have been processed, then, at step 636, the resulting line having the calculated phase durations for each of the four major sterilizer phases is added to the steri run report file and the program returns to step 640 of the finishSteriRunReport procedure (FIG. 15). If the phase duration values for all four major sterilizer phases have not been processed, then steps 633 and 634 will be repeated for each successive phase pointed by the pointer as indicated at step 638 of FIG. 17.

Figure 18:
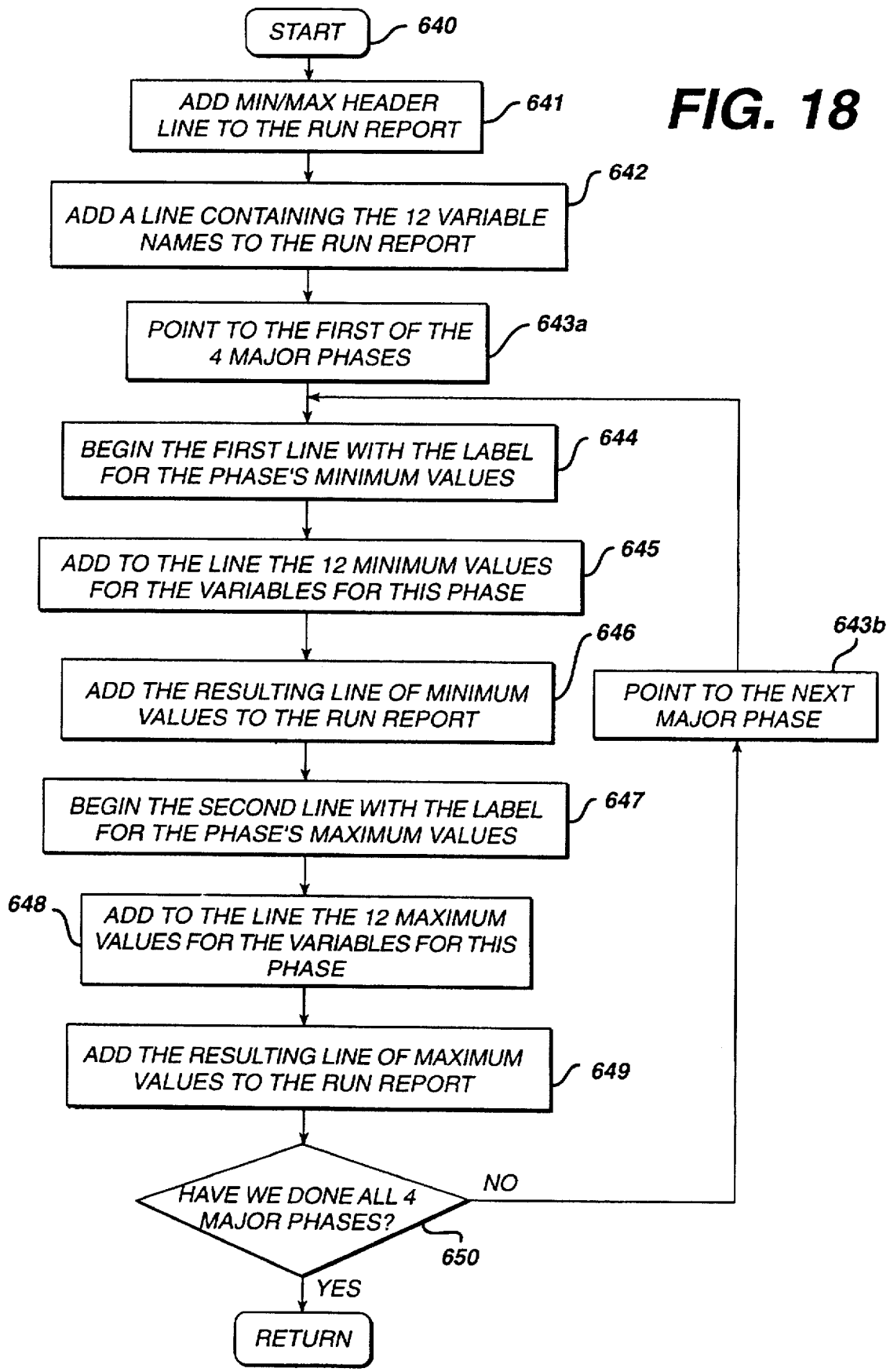
FIG. 18 illustrates the addMinMax procedure 640 for adding the minimum and maximum phase variable data to the sterilizer run report.

The addMinMax procedure 640 called by the finishSteriRunReport procedure begins by adding the Min/Max header line to the sterilization run report file as indicated as step 641 of FIG. 18. Next, as indicated at step 642, a line containing the twelve variable names are added to the run report file. Then, a pointer is set to the first of the four major phases, as indicated at step 643a. For each phase, a line for the minimum readings and a line for the maximum readings are to be added to the file. The following steps indicate the printing of minimum and maximum readings: at step 644, a label for the phase's minimum values is added at the beginning of a first line of the file; then, at step 645, a line containing the twelve minimum values for the variables for this phase are added; at step 646, the resulting line of minimum values is added to the steri run report file; at step 647, a label for the phase's maximum values is added at the beginning of a second line of the file; then, at step 648, a line containing the twelve maximum values for the variables for this phase are added; and, at step 649, the resulting line of maximum values is added to the steri run report file. Next, a determination is made at step 650 as to whether the Min/max values for all four major sterilizer phases have been added to the steri run report file. If the Min/max values for all four major sterilizer phases have been printed, then the process returns to step 486 of the doEndofRunEvent procedure for printing of the sterilizer phase durations. Until the Min/max values for all four major sterilizer phases have been printed, step 644 through step 649 will be repeated for each phase pointed to by the pointer as indicated at step 643b of FIG. 18.

Finally, after performing the addDurations and addMinMax values, a return is made to the doEndofRunEvent procedure 480 where the doEndOfRunCleanup procedure is performed at step 486, as indicated in FIG. 12.

Figure 16:
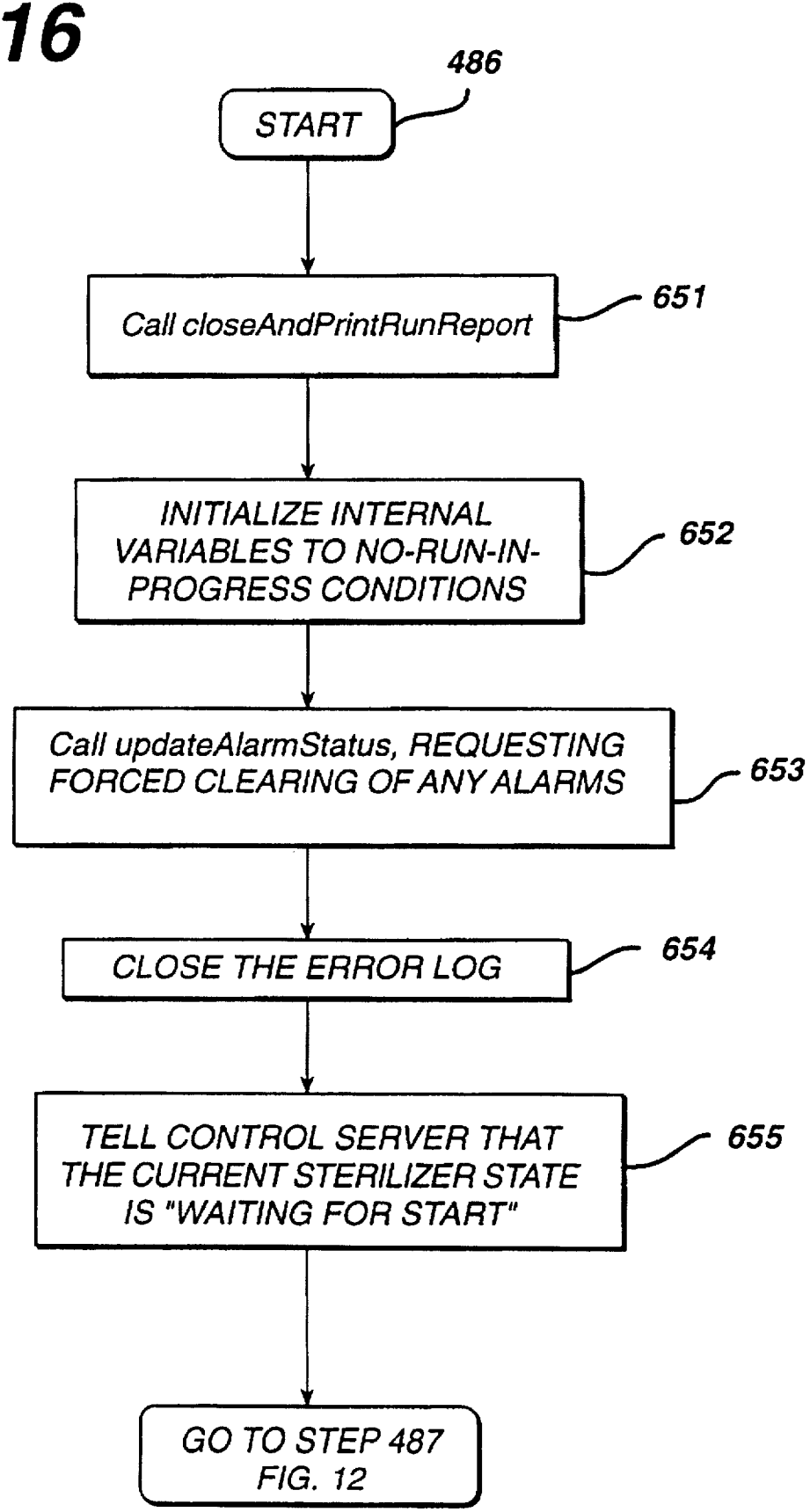
FIG. 16 illustrates the doEndOfRunCleanup procedure 486 to finish the text line processing and print the steri run report.

FIG. 16 illustrates the doEndOfRunCleanup procedure 486. As shown at step 651, this procedure implements the closeAndPrintRunReport procedure for closing and printing the sterilization run report, as described in further detail below with respect to FIG. 20 steps 660 through 669. Furthermore, the doEndOfRunCleanup procedure of FIG. 16 will: initialize all internal variables to no-run-in-progress conditions at step 652; invoke the update alarm status procedure at step 653 and as described above with respect to FIG. 14 steps 552 through 565; close the error log at step 654; and, at step 655, communicate to the control server that the sterilizer is currently in a standby or waiting state. Finally, a return is made to step 487 of the doEndofRunEvent procedure of FIG. 12.

As illustrated in FIG. 20, to close and print the sterilization run report, the first step 660 is to close the run report file. As mentioned above, if a sterilizer cycle was determined to be incomplete, a sterilizer run number may not have been obtained for the incomplete run. Therefore, at step 662, a determination is made if a sterilization run number has been obtained for this run. If a sterilization run number has been obtained for this run, then, at step 665, a new run report name is configured that will preferably comprise the sterilization run number followed by an underscore and the lot number. At step 667, the run report file is renamed to the new configuration. Finally, the run report file is printed at step 669. If a sterilization run number had not been obtained for this run, then, at step 663, an entry is placed in the error log indicating that there is no steri run number and the run report file is printed at step 669 with the default file name which is initially assigned as comprising the date and time as described above with respect to step 328, FIG. 19. After the run report file is printed at step 669, the process returns to step 652 of the doEndOfRunCleanup procedure 486 (FIG. 16).

The printed sterilizer run report 800 for a valid and complete run, as shown in FIGS. 23(a), 23(b) and 23(c), and printed by the printer 18 connected to the node 20, consists of: the updated steri run report file name comprising the sterilization run number followed by an underscore and the lot number, as indicated as line 810; heading data, indicated as lines 815, that includes: the date and time a sterilizer run begins, lines 816a, 816b, respectively; the name and number uniquely identifying the sterilizer, lines 817a,817b, respectively; a cycle counter number to uniquely identify the sterilizer run, line 818; twelve sterilizer process parameters, indicated as lines 819, of which the Expose Timer therein indicates the target value for the duration of the Exposure Phase; the program 822 which indicates the control program in the sterilizer controller; and, the progtime, 824, indicating the column headings for the output data lines, indicated as lines 825, that are sent to the existing supervisory controller 100 and sterilizer monitoring node 20 by the sterilizer controller 25. Each of the data lines 825 additionally include the time relative to the start of the run, followed by a reading for each of the twelve signals described in the header. Also provided are: the sterilization run number indicated as line 812; the lines of variable data for twelve process variable data labelled V1-V12 and generated once every minute; the durations for the four major sterilization phases, indicated as line 835 with label header line 830; the minimum and maximum readings observed for each sterilizer variable during each of the four major sterilization phases, as indicated as lines 845, with a header line 840; the sterilization run success failure assessment, indicated as line 850; and, if all data has been received for the four sterilization phases, i.e., for the current run, then the line 855 indicating that the data is complete. Additionally, a line 805 for placing the signature of an operator or engineer is provided in the steri run report. Alarm information (for e.g., fan failure) may also be printed by the sterilizer controller and any alarm text is printed on a line by itself. The sterilizer controller will surround the alarm text with printer control codes that cause the text to be printed in red.

Although not shown, the dedicated printer 17 (FIG. 1) will print out a sterilization run report similar to the report shown in FIGS. 23(a), 23(b) and 23(c) directly from the sterilizer controller via serial data line 16a. However, the report printed by dedicated printer 17 will not have the phase duration and minimum/maximum value summaries, and success/failure indications as provided in the sterilizer run report generated by the sterilizer monitoring node.

Figure 21A:
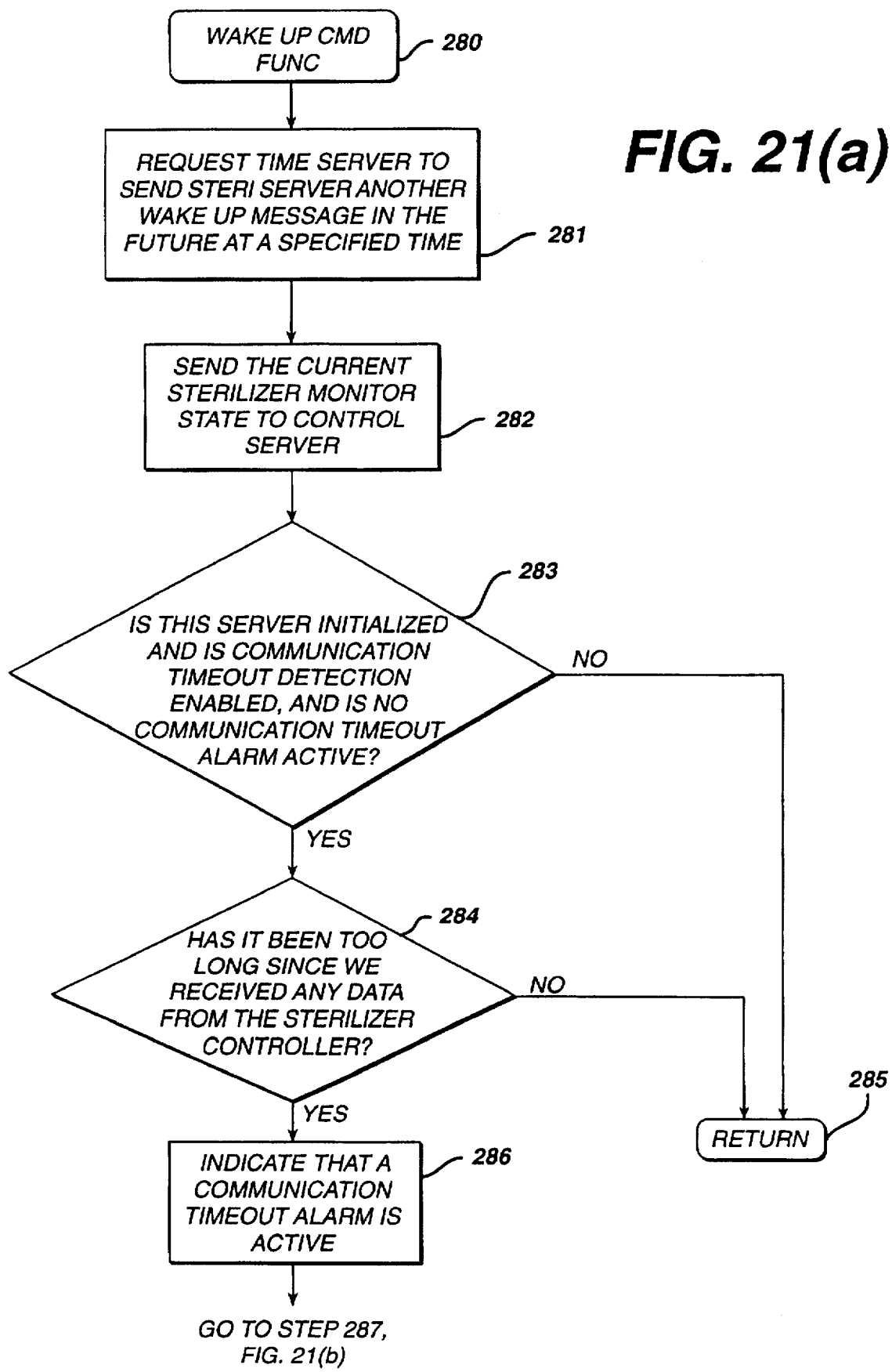
FIGS. 21(a) and 21(b) illustrate in detail the wakeUpCmdFunc process 280 invoked by the CELLworks system.
Figure 21B:
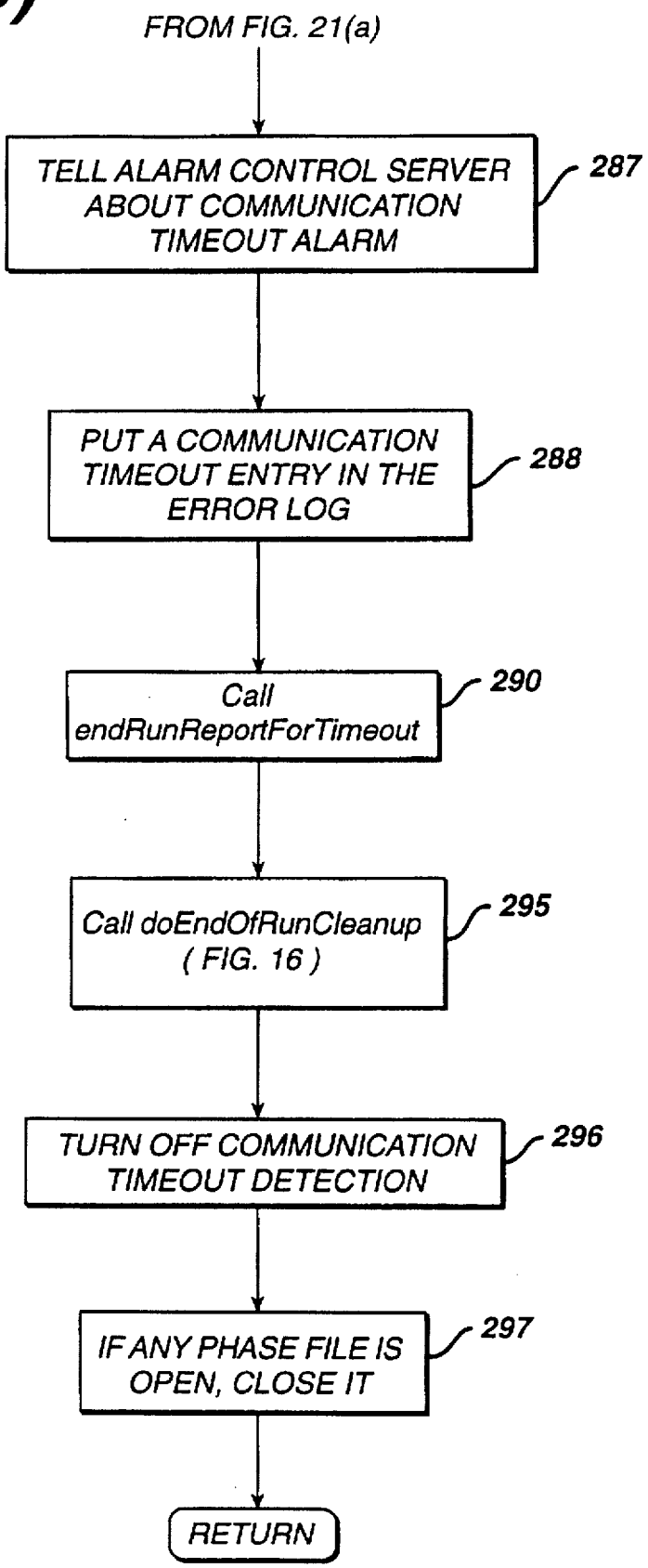

FIGS. 21(a) and 21(b) illustrates in detail the wakeUpCmdFunc process 280, which is a software function that is executable whenever the Time Server 70 (FIG. 3) sends a wakeup message to the Steri server process 60. As illustrated in FIG. 21(a), the first step 281 of the wakeUpCmdFunc process is to request the time server to send to the steri server 60 another wakeup message at a specified time in the future. It is understood that this is not a continuous process and that the time server 70 must be requested to send a wakeup message to the steri server. The next two steps, indicated as steps 283 and 284 are to indicate if a communication timeout has occurred. Specifically, at step 283, a determination is made as to whether the steri server is initialized, the timeout detection function is enabled, and that there is currently no communication timeout alarm that is active. If any of these conditions do not exist, then the process will return to the CELLworks system as indicated at step 285. If all these conditions exist, then at step 284, a determination is made as to if an undue amount of time, for e.g., greater than one (1) minute, has elapsed since the last receipt of data. A condition such as this would occur if the serial data line has been temporarily disconnected. If the amount of time since the last data receipt is not excessive (not greater than 1 minute), the process will return to the CELLworks system as indicated at step 285. If the amount of time since the last data receipt is excessive, then, at step 286, a communication timeout alarm is indicated as active. Then, at step 287, a communication timeout alarm message is sent to the alarm control server of the existing supervisor system. Additionally, at step 288, a communication timeout alarm entry is made in the error log. Next, at step 290, an endRunReportForTimeout process is called as illustrated in FIG. 22 and described in detail as follows: First, at step 291, a determination is made as to whether a sterilizer run report file is currently open. If a sterilizer run report file is not currently open, then the process returns to step 295 of the wakeUpCmdFunc process. If a sterilizer run report file is currently open, then, at step 292, a line is added to the run report file indicating that a communication timeout has occurred, and, at step 293, that there is incomplete run data for the current sterilizer run. At step 294, an entry is made in the error log that the run data is incomplete and the process returns to step 295 of the wakeUpCmdFunc process of FIG. 21(b). At step 295, the doEndOfRunCleanup procedure is called as described above with respect to FIG. 16. Finally, the communication timeout enable function is disabled at step 296 and, at step 297, any phase file that is currently open, is closed before returning to the wakeUpCmdFunc process.

Lot Tracking and Reconciliation

As shown in FIG. 2(a), lot number and power for the lenses to be produced will be input by operators at any of the four operator stations 230 located along the production line. Then, the lot reconciliation and tracking algorithms 90 that are resident at the stations are implemented for calculating and recommending the expiration date, lens center thickness, and other variables for lot information storage. In the preferred embodiment, the expiration date is sixteen months from the entered system date, but the number of months may change and the algorithm is easily modifiable by skilled artisans.

Figure 24:
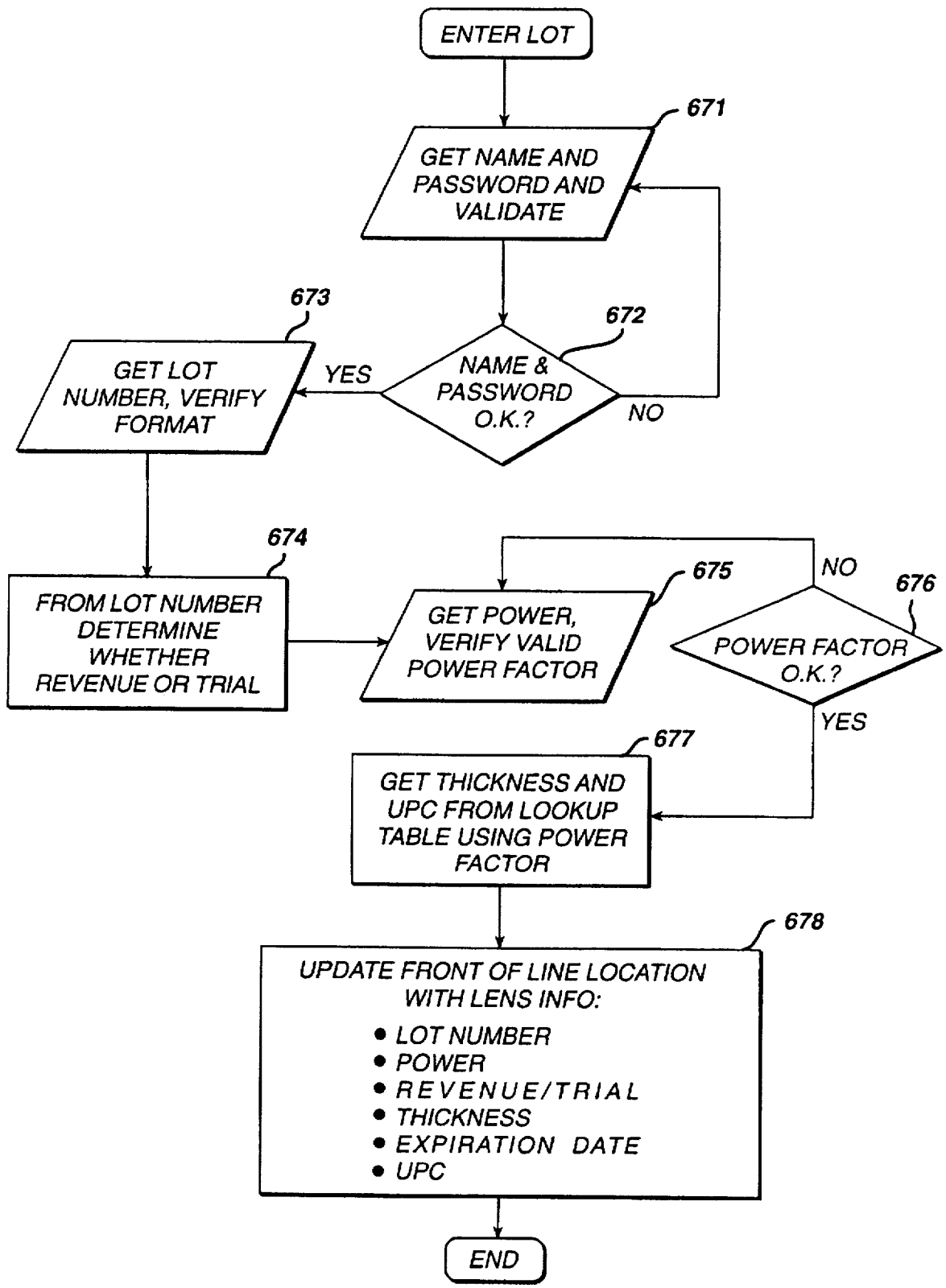
FIG. 24 illustrates the algorithm for contact lens lot number information entry.

As indicated in process flow diagram of FIG. 24, an operator will first be queried to enter his/her name and password as shown as step 671 which are then verified at step 672 by the password files of authorized individual names and passwords residing in the data analysis node (not shown). Using the operator entry of lens lot number, power value information and the current date information at the operator stations, the lot tracking and reconciliation algorithm 90 is implemented. Specifically, at step 673, the entered lens lot number is retrieved and the format of the lens lot number is verified. From the verified lot number which contains a digit that signifies whether the lot is for revenue or trial ("R/T"), a determination is made at step 674 as to whether the lot will be for revenue or trial. Next, at step 675, the entered lens power value is retrieved and the validity of the power factor is verified. A determination as to whether the power factor is valid is made at step 676. If not a valid power factor, the operator is prompted to enter a new power factor for validation (step 675). If the power factor is valid, the algorithm will use look-up tables (not shown) to determine the product code ("UPC") and lens center thickness information for the lot at step 677. It should be understood that the lot number, power value information, lot expiration date, product code and other entries may be displayed at the front of the production line, as shown at step 678, and, at any of the operating stations until the product reaches primary packaging. Additionally, the lot number, power value information and other entries may be changed until the lots product reaches primary packaging.

To aid in tracking lot movement, lot reconciliation, and lot changeover procedures, a display is available at either an operator station or a DynaTerm display station 29a,b at the sterilizer node to enable an operator to request for display in formatted fields, the stored or previously entered lot number data including lot number, product code, lens power, lens center thickness, expiration date, whether the product is for revenue or trial, as well as the current location of the lot on the line. As will be explained in further detail below, besides displaying the previous-entered information, the sterilization run number, as provided by the Sterilization server 60 of the sterilization node 20, may also be displayed. It is understood that the each operator station shown in FIG. 2(a) has a specialized CELLworks program for obtaining operator requests and displaying information to the operator in formatted fields.

Lot Tracking

As mentioned above, an operator is capable of sequencing the lot to the next part of the line. When the lot enters production, six variables representing lot number information are stored in the Statistics Server of the existing Supervisory control system 100. These variables are lotnumber, UPC, R/T, Power, Thickness, and Expiration and is shown having the data structure as shown in FIG. 25(a). Depending upon the manufacturing zone where the lot is located, each data structure for the lot is tagged with an "O" or "F" to respectively signify whether the lot is prior to line, or, is at the front of the line (injection molding, lens fab, cure, demold, etc.) prior to packaging. When a lot starts into primary packaging, the data structure of FIG. 25(a) is tagged with a "P" to signify that it is in packaging. When the lot of lenses are in the tray loading area, sterilization, or secondary packaging areas, the Statistics server 225 will store two additional variables onto the data structure of FIG. 25(a) to form new data structure as shown in FIG. 25(b). These variables are the input quantity and loss quantity and are supplied to the system during lot reconciliation. When a lot starts into the sterilizer tray loader area, the variables are tagged with an "L", and when the lot enters the sterilizer they are tagged with an "S". When a lot enters secondary packaging, the six lot information variables are tagged with a "C" to signify cartoning. Thus, the feature of the present invention is the ability for an operator to track movement of a particular lot.

Figure 26:
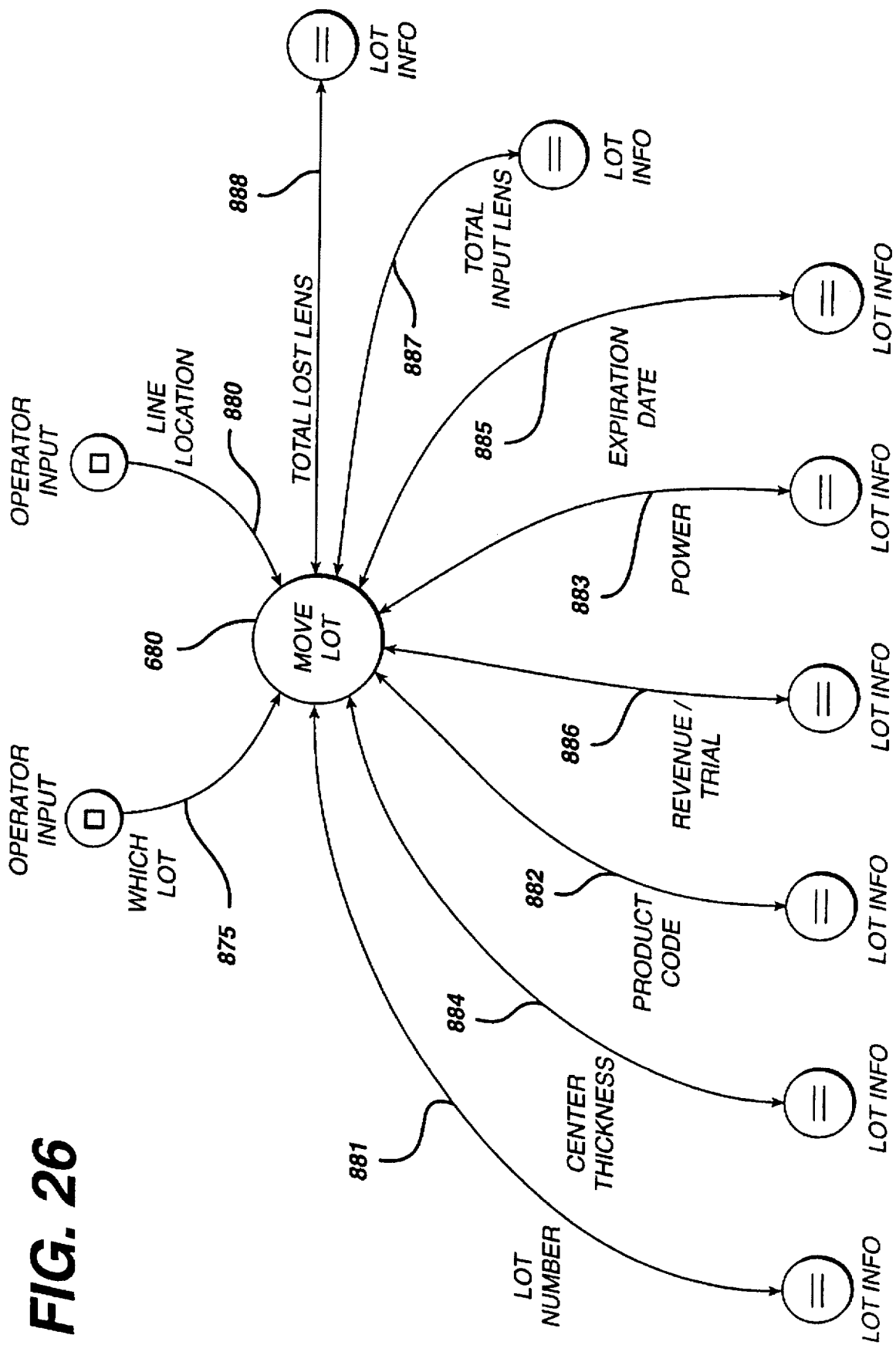
FIG. 26 illustrates a data flow diagram for moving a lot by operator request.

As shown in the data flow diagram of FIG. 26, an operator may request movement of a lot by inputting data such as the requested lot 875 being processed on the line, and, to which location 880 on the production line to which the lot is to be moved. A moveLot algorithm 680 is implemented which will process the operator entered data, as well as lot information data such as: lot number 881, product code 882, power 883, lens center thickness 884, expiration date 885, whether the product is for revenue or trial 886, and, total lens input to the particular location of the line 887 and the total lenses lost 888 (as will be explained below).

Figure 27:
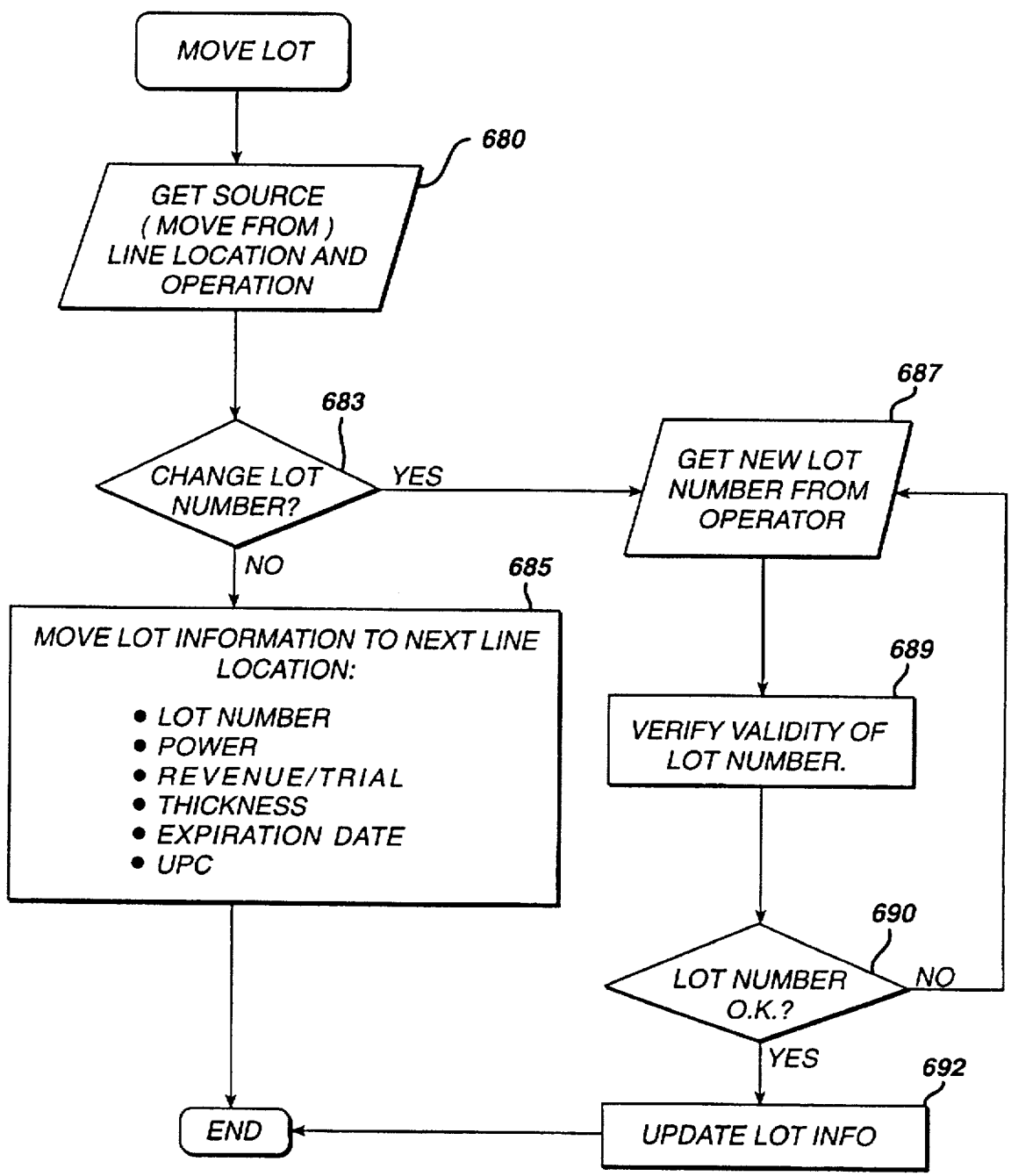
FIG. 27 illustrates the moveLot algorithm 680 for tracking lens lot movement throughout the production line.

FIG. 27 illustrates the moveLot algorithm 680 for tracking lens lot movement throughout the production line. As shown as step 680 in FIG. 27, the source location of the lens lot on the production line is retrieved. Next, at step 683, a determination is made as to whether the lot number is to be changed, for instance, when a lot is to be split prior to entry in the sterilizer 15 as a preventative measure to eliminate defective batches rather than a whole lens lot when there exists a problem in the line. If the lot number is not to be changed, then, at step 685, the lens lot and lot information data such as: lot number, product code, power, lens center thickness, expiration date, and whether the product is for revenue or trial, is moved to the next line location and tagged with a "P","L","S" or "C" indicator depending at which point on the line the lens lot has moved to. If the lot number is to be changed, then, at step 687, the lens lot number is retrieved from the operator and the format of the lens lot number is verified at steps 689 and 690. If the entered lot number is not valid, the operator is prompted to enter a new power factor for validation (step 687). If the lot number entered is valid, the algorithm will proceed to update the above-identified lot information at step 692.

Lot Reconciliation

Due to the fact that product may be lost during manufacture, or, may be removed for quality assurance purposes, it is necessary to account for this product and the reasons for their loss or removal prior to secondary packaging. Lot reconciliation is the process whereby each lens of a particular lot that leaves primary packaging, hereinafter indicated as Zone 1, and enters sterilization (sterilization tray loading), hereinafter indicated as Zone 2, is accounted for at the time that the lot is available for secondary packaging, (i.e., sterilization tray unloading, cartoning, check weighing, and labelling), hereinafter indicated as Zone 3. Particularly, a lot reconciliation sheet 890, illustrated in FIG. 32, is generated that will indicate the number of lenses input to the sterilizer (line 891) and number of lenses available for secondary packaging (lines 899) as well as verify the difference that is equal to the number of lenses that have been lost or removed at each particular zone (lines 892,893,894 and 895). The lot tracking and reconciliation algorithm 90 in the existing supervisor control system 100 supports data entry and calculations for Lot Reconciliation.

Figure 28:
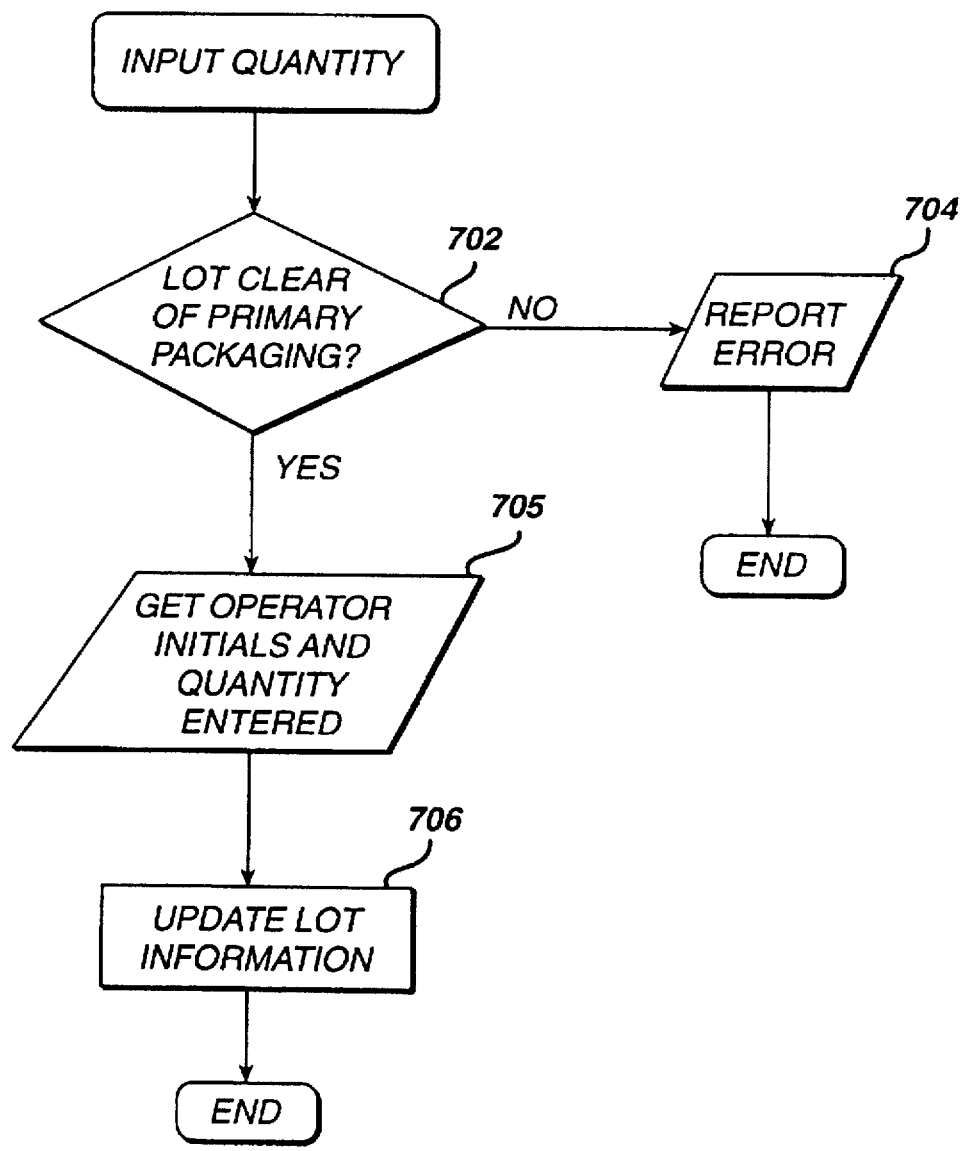
FIG. 28 illustrates the start of the lot reconciliation process which entails the reporting of the quantity of lenses input to the sterilizer.

FIG. 28 illustrates the start of the lot reconciliation process which entails the reporting of the quantity of lenses input to the sterilizer 15 after primary packaging. Before this quantity could be entered at the operator terminals 230 or the DynaTerm Operating consoles 29a,b (FIG. 2b), a determination is made at step 702 to determine whether the lot has cleared from primary packaging, i.e., have been packaged in blister packs and readied for sterilization. If not, then an error message will be displayed at step 704 that an input quantity can not be entered until the lot has cleared primary packaging (Zone 1). If the lot has cleared primary packaging, then the operator is prompted to enter his/her initials and the actual quantity of lenses ready for sterilization at step 705. Next, at step 706, the lot information is updated to reflect the new variable, quantity input, with the lot number.

Figure 29A:
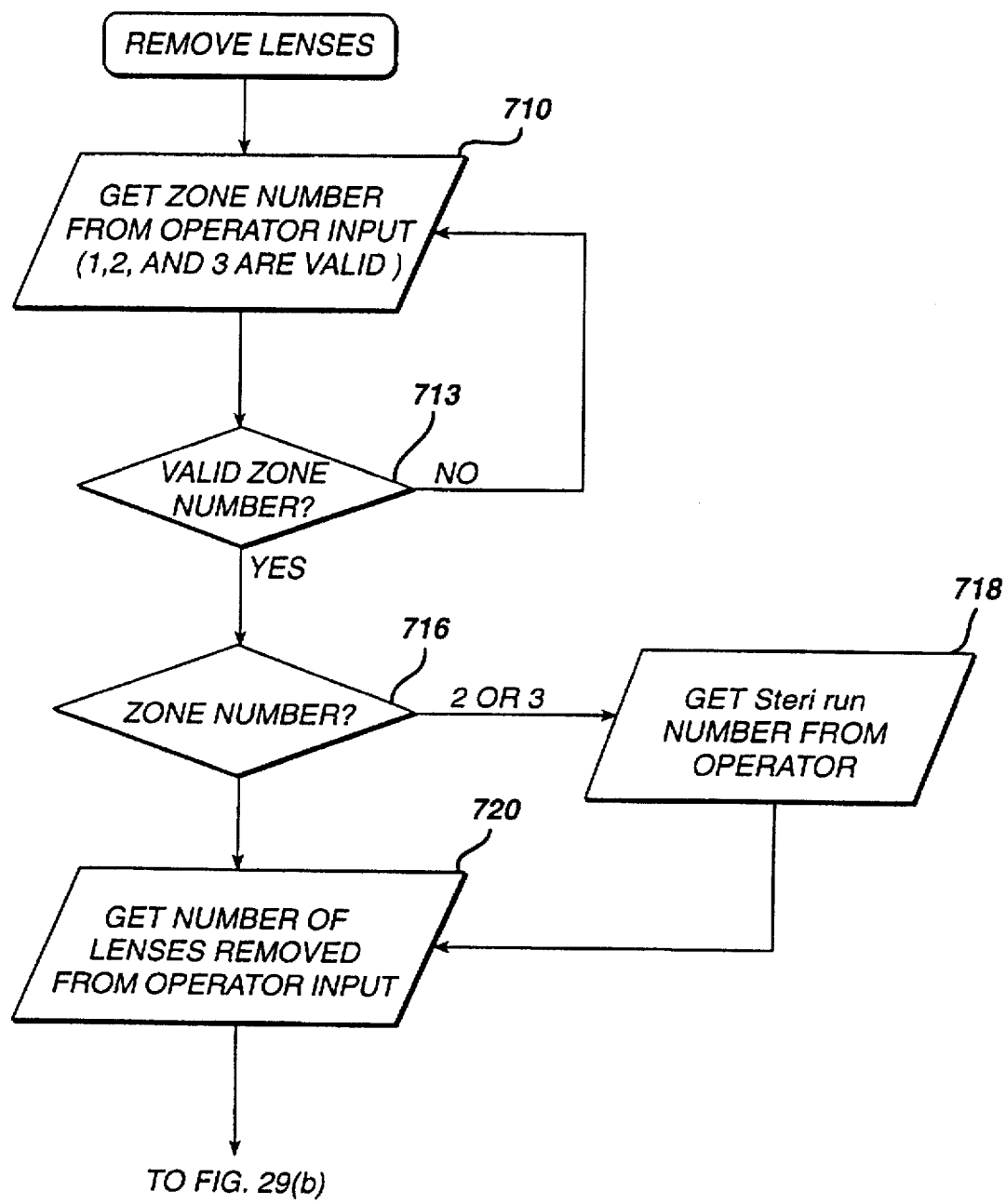
FIGS. 29(a) and 29(b) illustrate the procedure for entering the number of lenses removed from the secondary packaging process.

Just as a number representing the quantity of lenses entering sterilization is entered, the number of lenses removed from the sterilization (Zone 2) and secondary packaging (Zone 3) areas must be recorded and entered. As shown in FIG. 29(a), at steps 710 and 720, an operator may enter the number of product lost, the particular zone where the product was lost, the reasons why the product was lost or removed, and, the sterilization run number, all at the operator terminals or the DynaTerm Operating consoles. This information is all referenced with a particular lot number that is input from the sterilization server. This process may be repeated several times while a lot is in one zone, for e.g., when there are multiple incidents of lost lenses while in the zone.

Specifically, at step 710, the zone number for the current lot location is retrieved and a verification is made at step 713 as to whether the zone number is valid. If not, then the operator will be prompted to enter the a correct zone number. If the lot number is valid, then a determination is made at step 716 as to which zone number was entered. If the current lot is in Zone 2 or 3, then the operator is prompted to enter the Sterilization run number at step 718 before entering the number of lenses removed at step 720. If the current lot is in Zone 1, then the operator is prompted to enter the number of lenses removed at step 720. In response to entering the number of quantity removed, at step 723, the operator station or Dynaterm displays a reason selection list for the operator to enter the particular reason(s) why the lens packages were removed from production at step 725. As there may be multiple sterilization runs per lot, product may be lost for a number of reasons per sterilization run. Look-up tables (not shown) having reason codes and their definitions are available on each of the operator stations or DynaTerm consoles. Table 3 below details some of the reasons for lens removal:

TABLE 3

| REASON CODE | DEFINITION |
| --- | --- |
| 01 | Removed_by_QA |
| 02 | Lenses_to_Distribution |
| 03 | Foil_Tear_Mechanical |
| 04 | Foil_Tear_Foil_Size |
| 05 | Incorrect_Power_on_Foil |
| 06 | Incorrect_Expiration_Date_on_Foil |
| 07 | Illegible_Print_on_Foil |
| 08 | Misaligned_Print |
| 09 | Misaligned_Foil |
| 10 | Misaligned_Perforation |
| 11 | No_Solution |
| 12 | Low_Solution |
| 13 | Incorrect_Lot_Number_on_Foil |
| 14 | Incomplete_Seal |
| 15 | Perforation_Tear |
| 16 | Blown_Seal/Package |
| 17 | Barcode_Not_Printed_In_Proper_Place |
| 18 | Lot_Number_Not_In_Brackets |
| 19 | Incorrect_#_Digits_in_Lot#_Barcode |
| 20 | Incorrect_#_Digits_in_UPC_Barcode |
| 21 | Invalid_Barcode#_(Lot Number) |
| 22 | Invalid_Barcode#_(UPC) |
| 23 | Incorrect_Check_Digit |
| 24 | Spots_On-Barcode |
| 25 | Void(s)_On_Barcode |
| 26 | Low_Grade_Barcode_Scan_Verification |
| 27 | Excess_Glue |
| 28 | Tabs_Unsealed |
| 29 | Tabs_Unparallel |
| 30 | Ink_Smears_Carton |
| 31 | Damage_To_Carton |
| 32 | Foreign_Matter |
| 33 | Cartoner_Rejected_at_Checkweigher |
| 34 | Misaligned_Label |
| 35 | Print Out_of_Shaded_Area_Carton |
| 36 | Incorrect_Case_Label_Info |
| 37 | Jam_Array_Destroyed |
| 38 | Cartoner_Jam_Carton_Destroyed |
| 39 | Conveyor_Transfer_Jam_Carton_Destroyed |

TABLE 3-continued

| REASON CODE | DEFINITION |
| --- | --- |
| 40 | Jam_into_Belt_Array_destroyed |
| 41 | Jam_out_of_Belt_Array_Destroyed |
| 42 | No_Print_Foil |
| 43 | No_Perf_Foil |
| 44 | Extra_Lens |
| 60 | Supply_Your_Own_Reason |

Figure 29B:
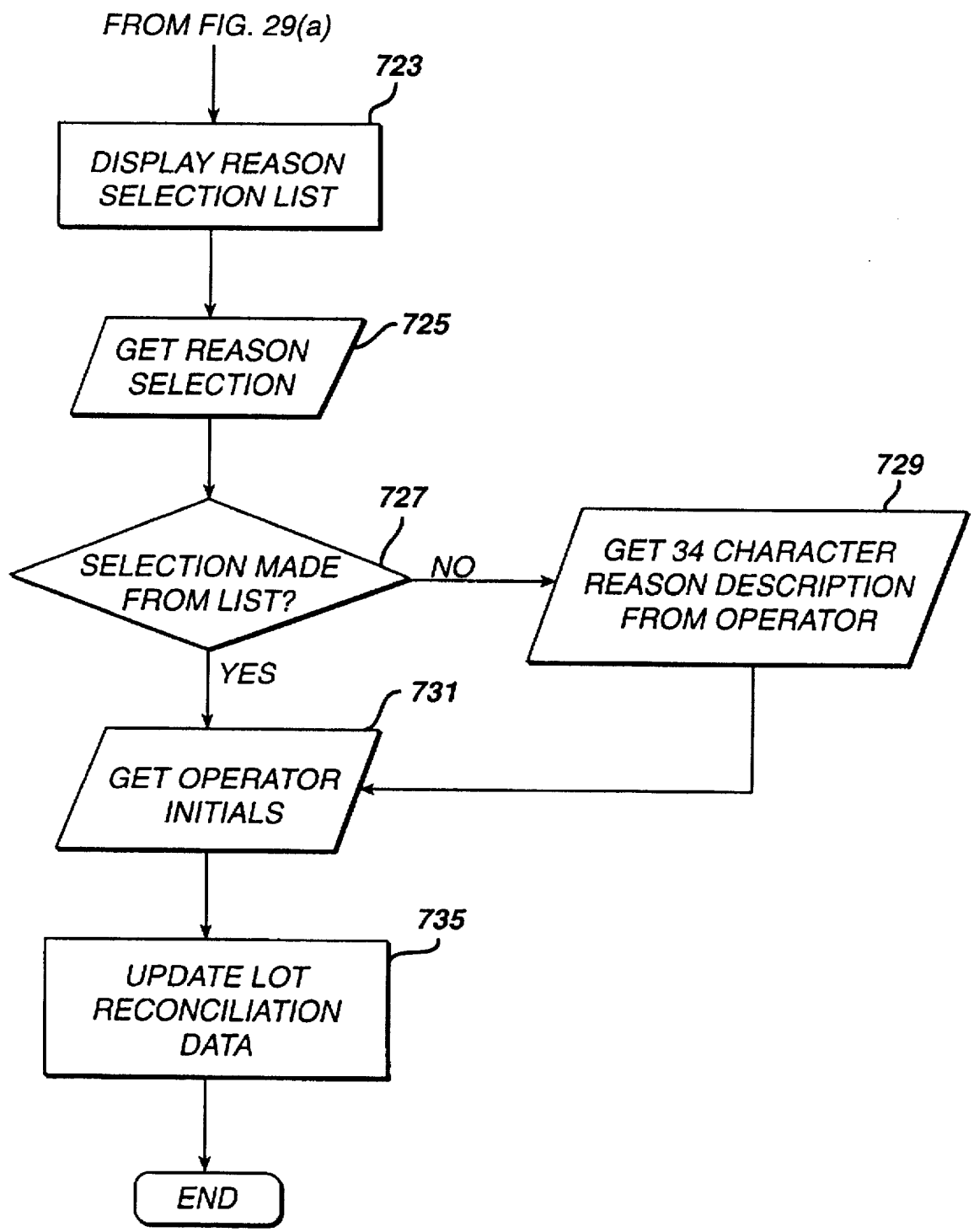

At step 727 in FIG. 29(b), a determination is made as to whether the selection is made from the list displayed on the operator station, or, whether the operator entered a new reason for lens package removal. If the selection is made from the displayed list, then the operator is prompted to enter his/her initials at step 731. If the operator entered a new reason for lens package removal, the description entered by the operator, which may be up to 34 characters, is retrieved at step 729 prior to operator initials entry at step 731. The next step 735 updates the lot reconciliation data which has the data structure depicted as shown in FIG. 25(b) explained above.

Figure 30A:
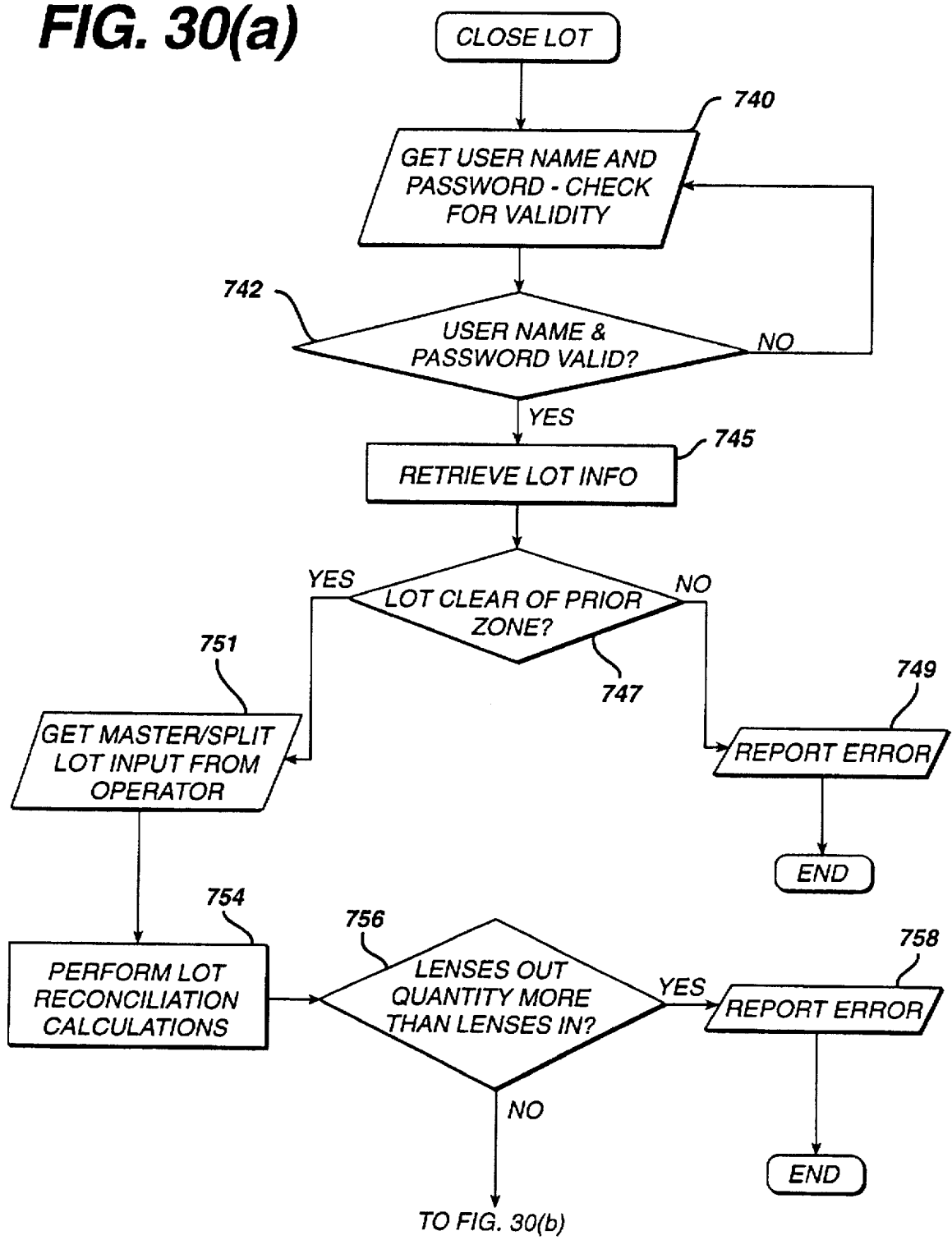
FIGS. 30(a) and 30(b) illustrate the lot close out flow diagram.
Figure 30B:
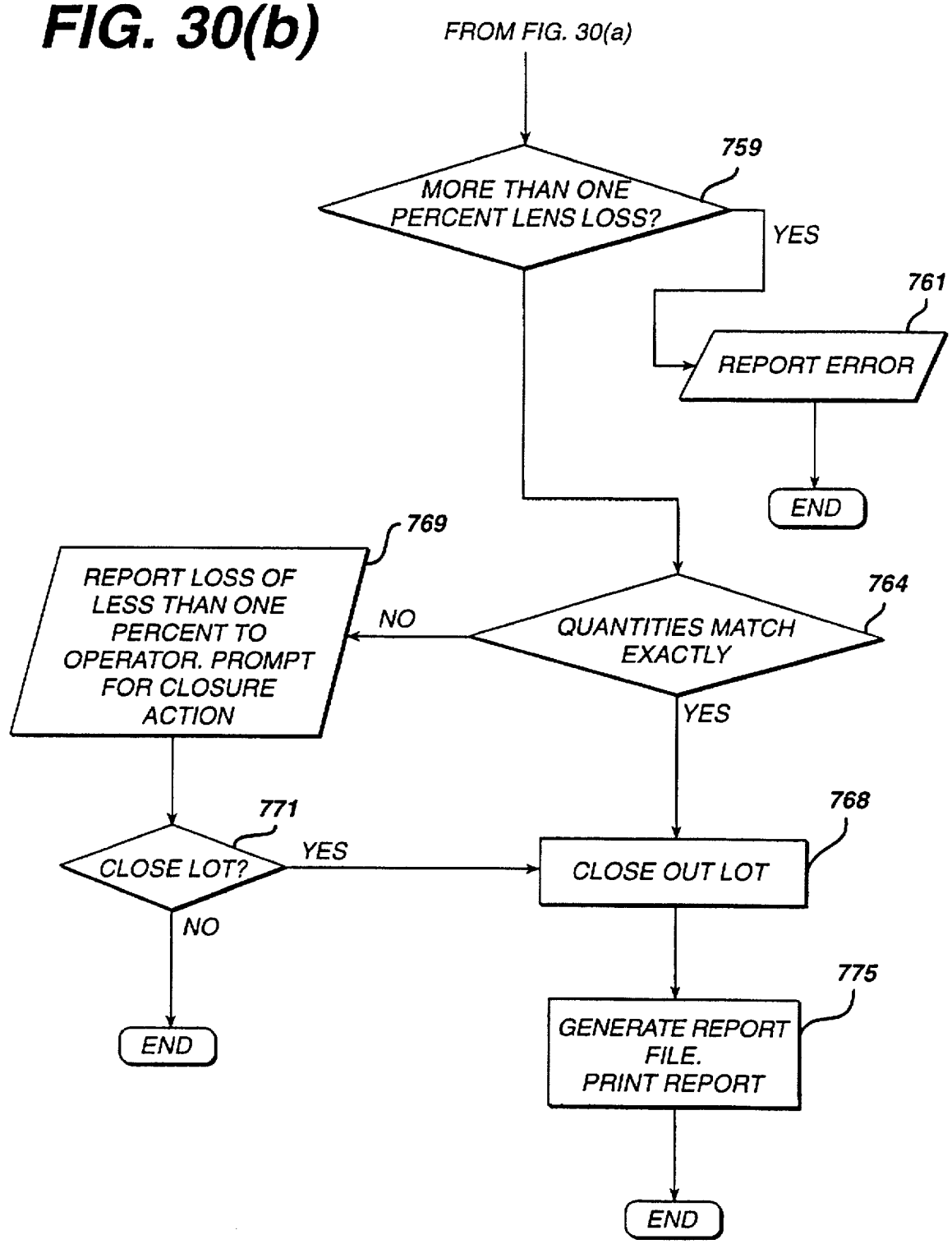

After secondary packaging is complete, the last action to be performed during lot reconciliation is to close out the lot as shown in the process flow diagram of FIGS. 30(a) and 30(b). As shown in FIG. 30(a), an operator will first be queried to enter his/her name and password as shown as step 740 which are then verified at step 742 by the password files. The updated lot information data is retrieved at step 745 and a determination as to if the lot has cleared the prior zone is made at step 747. If the lot has not cleared the prior zone, then an error is reported at step 749 and the lot will not be closed out. If the lot has cleared the prior zone, then the master lot (or split lot) information is obtained by operator entry at step 751. Then, at step 754, lot reconciliation calculations are performed to total number of lenses lost or removed. Next, at step 756, a determination is made if the total number of lens packages lost or removed is greater than the total number of lens packages input. If the total number of lens packages lost or removed is greater than the total number of lens packages input then an error message is reported at step 758. If the total number of lens packages lost or removed is greater than the total number of lens packages input then a determination is made at step 759 whether the total lost or removed is more than one percent (1%) of the total number input. If the total number of lens packages lost or removed is greater than one percent, then an error message is reported at step 761. If the total number of lens packages lost or removed is less than one percent, then a determination is made at step 764 whether the total lost or removed is equal to or less than one percent of the number of lenses input. If the lens package quantity input equals the quantity output, then the lot is closed out at step 768. If the total number of lens packages lost or removed is less than one percent of the quantity input, then the total loss of less than one percent is reported to the operator at step 769, and the operator is prompted for closure action at step 771. If the operator elects to close the master lot (or split lot) at step 771, then the master lot (or split lot) is closed at step 768. Then, a lot reconciliation report is created for storage and printing as indicated at step 775.

While the invention has been particularly shown and described with respect to the preferred embodiments thereof, it will be understood by those skilled in the art that the foregoing and other changes in form and details may be made therein without departing from the spirit and scope of the invention, which should be limited only by the scope of the appended claims.

We claim:

1. A quality control system for an automated production line producing contact lenses, said production line having a plurality of contact lens process stations, including an automated sterilization station for sterilizing a plurality of contact lenses after their manufacture, and a packaging station for packaging said lenses after sterilization, wherein the system comprises:
   (a) a first means for receiving contact lens data including an associated lot number and lens power for a lens lot prior to their manufacture; said lens lot defining at least one batch of contact lenses;
   (b) a plurality of process controllers for controlling one or more process stations, each of said controllers regulating a plurality of process control devices at said process stations for manufacturing said contact lenses;
   (c) means for tracking movement of said plurality of lenses defined by said lens lot from a said plurality of processing stations to said automated sterilization station and said packaging station;
   (d) means for receiving data representing the number of lenses that are input to said packaging station together with reason codes for contact lenses lost at said sterilization station;
   (e) means for generating a summary report of the total number of lenses input to said sterilization station for a predetermined lens lot and the actual number of lenses sterilized and packaged from said lot, said summary report including lot number and lens power data for each batch of contact lenses.

2. The quality control system as claimed in claim 1, wherein a lens lot comprises a plurality of batches of lenses, said sterilization station sterilizing said one batch of contact lenses at a time and generating a sterilization cycle run number for each batch sterilized.

3. The quality control system as claimed in claim 2, wherein said summary report reconciles the number of lenses input to said sterilization station with the number of lenses packaged from said batch for each sterilization cycle run number.

4. The quality control system as claimed in claim 2, wherein each lens lost or removed has associated therewith a reason code, said summary report generating means including the lens package removal code with a sterilization cycle run number.

5. The quality control system as claimed in claim 2, further including means for automatically calculating a thickness specification and product code for a given lens power.

6. The quality control system as claimed in claim 2, wherein the means for calculating a thickness specification and product code includes a look-up table.

7. The quality control system as claimed in claim 2, further including means for automatically calculating an expiration date for a given lens lot.

8. The quality control system as claimed in claim 2, wherein said tracking means includes means for displaying the location of a particular lot on said production line.

9. A sterilizer data processing system for an automated contact lens manufacturing line for manufacturing a plurality of contact lenses defined by a lens lot, said contact lens manufacturing line including an automated sterilization station for sterilizing said lens lot after their manufacture, said automated sterilization station including a sterilizer process controller for controlling one or more operating phases of a sterilization process, said process controller periodically generating sterilization process data during each said sterilization phase, said system including:

(a) means for receiving said sterilization data from said sterilizer process controller; and, (b) means for automatically parsing said sterilization data into text information and sterilizer parameter information, said means further processing said text information and sterilizer parameter information to automatically generate a sterilization run report associated with a lot number for said sterilized lens lot.

10. The sterilizer data processing system for an automated contact lens manufacturing line as claimed in claim 9, wherein said processing means further conveys said sterilizer parameter information to data acquisition devices in said automated contact lens manufacturing line for display and storage thereof.

11. The sterilizer data processing system for an automated contact lens manufacturing line as claimed in claim 9, wherein said process controller generates alarm condition information, said processing means further conveying said alarm condition information to data acquisition devices in said automated contact lens manufacturing line for display thereof.

12. The sterilizer data processing system for an automated contact lens manufacturing line as claimed in claim 9, wherein said processing means further includes means for evaluating the success or failure of a sterilization run based on said text information and sterilizer control parameter information for indication on said sterilization run report.

13. The sterilizer data processing system for an automated contact lens manufacturing line as claimed in claim 9, wherein said processing means further includes means for evaluating whether a complete set of data has been obtained for the current sterilizer run.

14. The sterilizer data processing system for an automated contact lens manufacturing line as claimed in claim 9, wherein said text information includes the current operating phase of said sterilization process.

15. The sterilizer data processing system for an automated contact lens manufacturing line as claimed in claim 9, wherein said sterilizer parameter information includes a plurality of isolated process values generated by said sterilization process controller during each operating phase of said sterilization process.

16. The sterilizer data processing system for an automated contact lens manufacturing line as claimed in claim 9, wherein said processing means further includes means for determining a phase duration time for each said operating phase of said sterilization run, wherein said phase duration time is included in said sterilization run report.

17. The sterilizer data processing system for an automated contact lens manufacturing line as claimed in claim 9, wherein said processing means further includes means for determining a minimum value and maximum value of isolated process values for each said sterilization phase, wherein said minimum and maximum of said isolated process values are included in said sterilization run report.

18. The sterilizer data processing system for an automated contact lens manufacturing line as claimed in claim 15, wherein said processing means further includes means for generating phase files for storing phase file information for each of said sterilizer operating phases.

19. The sterilizer data processing system for an automated contact lens manufacturing line as claimed in claim 9 wherein said sterilizer process controller generates sterilizer data at a first prespecified time interval, said sterilizer data processing system further including means for determining whether said receiving means receives said sterilization data from said sterilizer process controller within said time interval.

20. The sterilizer data processing system for an automated contact lens manufacturing line as claimed in claim 19 wherein said means for determining whether said receiving means receives said sterilization data from said sterilizer process controller within said time interval includes a time server for generating a wakeup message during each said first time interval.

21. The sterilizer data processing system for an automated contact lens manufacturing line as claimed in claim 20, wherein said processing means generates a communication timeout alarm message in the event that said sterilization data is not received during each said first time interval.

22. The sterilizer data processing system for an automated contact lens manufacturing line as claimed in claim 9 wherein said receiving means is a communication server.

23. The sterilizer data processing system for an automated contact lens manufacturing line as claimed in claim 9 wherein said processing means is a sterilization server.

24. The sterilizer data processing system for an automated contact lens manufacturing line as claimed in claim 11 wherein said sterilizer process controller generates alarm condition information at a second prespecified time interval.

25. A method for processing data generated in an automated contact lens manufacturing line for manufacturing a plurality of contact lenses defined by a lens lot, said contact lens manufacturing line including an automated sterilization station for sterilizing said lens lot after their manufacture, said automated sterilization station including a sterilizer process controller for controlling one or more phases of a sterilization process, said process controller periodically generating sterilization process data during each said sterilization phase, said method including the steps of:

(a) receiving said sterilization data from said sterilizer process controller; and, (b) automatically parsing said sterilization data into text information and sterilizer parameter information; and, (c) further processing said text information and sterilizer parameter information to automatically generate a sterilization run report associated with a lot number for said sterilized lens lot.

* * * * *